US011965184B2

(12) United States Patent
Chen

(10) Patent No.: US 11,965,184 B2
(45) Date of Patent: *Apr. 23, 2024

(54) CRISPR/CAS FUSION PROTEINS AND SYSTEMS

(71) Applicant: Sigma-Aldrich Co. LLC, St. Louis, MO (US)

(72) Inventor: Fuqiang Chen, St. Louis, MO (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/172,734

(22) Filed: Feb. 10, 2021

(65) Prior Publication Data

US 2021/0163910 A1 Jun. 3, 2021

Related U.S. Application Data

(62) Division of application No. 16/790,399, filed on Feb. 13, 2020, now Pat. No. 10,947,517.

(60) Provisional application No. 62/806,708, filed on Feb. 15, 2019.

(51) Int. Cl.
  *C12N 9/22* (2006.01)
  *C07K 14/205* (2006.01)
  *C07K 14/31* (2006.01)
  *C07K 14/315* (2006.01)
  *C12N 15/113* (2010.01)

(52) U.S. Cl.
  CPC .............. *C12N 9/22* (2013.01); *C07K 14/205* (2013.01); *C07K 14/31* (2013.01); *C07K 14/315* (2013.01); *C12N 15/113* (2013.01); *C07K 2319/09* (2013.01)

(58) Field of Classification Search
  CPC ........ C12N 9/22; C07K 14/31; C07K 14/205; C07K 14/315
  See application file for complete search history.

(56) References Cited

U.S. PATENT DOCUMENTS

| 10,808,245 | B2 * | 10/2020 | Chong | C12N 15/11 |
| 11,071,791 | B2 * | 7/2021 | Millette | A61K 48/0058 |
| 2014/0068797 | A1 | 3/2014 | Doudna et al. | |
| 2016/0136293 | A1 | 5/2016 | Littman et al. | |
| 2017/0314015 | A1 | 11/2017 | Friedland et al. | |
| 2019/0231899 | A1 * | 8/2019 | Millette | A61K 48/0091 |
| 2019/0249200 | A1 | 8/2019 | Seebeck et al. | |
| 2020/0063126 | A1 * | 2/2020 | Cheng | C12N 15/102 |
| 2020/0263155 | A1 | 8/2020 | Chen | |

FOREIGN PATENT DOCUMENTS

| CN | 108913676 A | 11/2018 |
| JP | 2017-506886 A | 3/2017 |
| JP | 2017-532001 A | 11/2017 |
| JP | 2018-518969 A | 7/2018 |
| JP | 2022-520104 A | 3/2022 |
| WO | 03/046141 A2 | 6/2003 |
| WO | 2013/176772 A1 | 11/2013 |
| WO | 2014/089290 A1 | 6/2014 |
| WO | 2014/186686 A2 | 11/2014 |
| WO | 2015/089486 A2 | 6/2015 |
| WO | 2015/126729 A1 | 8/2015 |
| WO | 2016/054326 A1 | 4/2016 |
| WO | 2016/210271 A1 | 12/2016 |
| WO | 2017/131150 A1 | 8/2017 |
| WO | 2017/173004 A1 | 10/2017 |
| WO | 2017/180694 A1 | 10/2017 |
| WO | 2018/027078 A1 | 2/2018 |
| WO | 2018-031683 A1 | 2/2018 |
| WO | 2018/071868 A1 | 4/2018 |
| WO | 2018/108339 A9 | 9/2018 |
| WO | 2018/165504 A1 | 9/2018 |
| WO | 2019/008335 A1 | 1/2019 |
| WO | 2019/025984 A1 | 2/2019 |

OTHER PUBLICATIONS

Airenne, "Recombinant Avidin and Avidin-Fusion Proteins", Biomolecular Engineering, vol. 16, Issues 1-4, Dec. 31, 1999, pp. 87-92.
Anders et al., "Structural Basis of PAM-dependent Target DNA Recognition by the Cas9 Endonuclease", Nature, vol. 513, Sep. 25, 2014, pp. 569-573.
Brouns, "A Swiss Army Knife of Immunity", Science, vol. 337, No. 6096, Aug. 2012, pp. 808-809.
Carroll, Dana, "A CRISPR Approach to Gene Targeting", Molecular Therapy, vol. 20, No. 9, Sep. 2012, pp. 1658-1660.
Chung et al., "Human Embryonic Stem Cell Lines Generated without Embryo Destruction", Cell Stem Cell, vol. 2, Issue 2, Feb. 7, 2008, pp. 113-117.
Cong et al., "Multiplex Genome Engineering Using CRISPR/Cas Systems", Science, vol. 339, No. 6121, Feb. 15, 2013, pp. 819-823.
Crasto et al., "Linker: A Program to Generate Linker Sequences for Fusion Proteins", Protein Engineering, vol. 13, No. 5, 2000, pp. 309-312.
Cull et al., "Biotinylation of Proteins in Vivo and in Vitro using Small Peptide Tags", Methods in Enzymology, vol. 326, 2000, pp. 430-440.
Dayhoff, Margaret O., "Atlas of Protein Sequence and Structure", National Biomedical Research Foundation, vol. 5, 1978, pp. 345-358.
Deltcheva et al., "CRISPR RNA Maturation by Trans-Encoded Small RNA and Host Factor RNase III", Nature, vol. 471, Mar. 2011, pp. 602-607.
Edraki et al., "A Compact, High-Accuracy Cas9 with a Dinucleotide PAM for In Vivo Genome Editing", Molecular Cell, vol. 73, No. 4, Dec. 20, 2018, 14 pages.
Genbank, "Type II CRISPR RNA-guided endonuclease Cas9 [Bacillus smithii]", GenBank Accession No. WP_003354196.1, Oct. 2015, 01 page.
Gribskov et al., "Sigma factors from *E. coli*, *B. subtilis*, Phage SP01, and Phage T4 are Homologous Proteins", Nucleic Acids Research, vol. 14, No. 16, 1986, pp. 6745-6763.

(Continued)

*Primary Examiner* — Maryam Monshipouri
(74) *Attorney, Agent, or Firm* — Sigma-Aldrich Co. LLC

(57) ABSTRACT

Engineered Cas9 systems are disclosed herein.

10 Claims, 3 Drawing Sheets

Specification includes a Sequence Listing.

(56) References Cited

OTHER PUBLICATIONS

Jinek et al., "A Programmable Dual-RNA-Guided DNA Endonuclease in Adaptive Bacterial Immunity", Science, vol. 337, Aug. 2012, pp. 816-821.

Jinek et al., "RNA-programmed Genome Editing in Human Cells", eLIFE, vol. 2, e00471, 2013, pp. 1-9.

Jinek et al., "Supplementary Materials for—A Programmable Dual-RNA-Guided DNA Endonuclease in Adaptive Bacterial Immunity", Science, Jun. 2012, 37 pages.

Karvelis et al., "Methods for Decoding Cas9 Protospacer Adjacent Motif (PAM) Sequences: A Brief Overview", Methods, vol. 121-122, 2017, pp. 3-8.

Kipriyanov et al., "Single-Chain Antibody Streptavidin Fusions: Tetrameric Bifunctional scFv-complexes with Biotin Binding Activity and Enhanced Affinity to Antigen", Human Antibodies and Hybridomas, vol. 6, No. 3, Feb. 1995, pp. 93-101.

Kleinstiver, et al., "Engineered CRISPR-Cas9 Nucleases with Altered PAM Specificities", Nature, vol. 523, No. 7561, Jul. 23, 2015, pp. 481-485.

Konermann et al., "Genome-scale Transcriptional Activation by an Engineered CRISPR-Cas9 Complex", Nature, vol. 517, No. 7536, Jan. 29, 2015, pp. 583-588.

Koonin et al., "Diversity, Classification and Evolution of CRISPR-Cas Systems", Current Opinion in Microbiology, vol. 37, Jun. 2017, pp. 67-78.

Laitinen, et al., "Rational Design of an Active Avidin Monomer", The Journal of Biological Chemistry, vol. 278, No. 6, Feb. 7, 2003, pp. 4010-4014.

Leenay et al., "Identifying and Visualizing Functional PAM Diversity across CRISPR-Cas Systems", Molecular Cell, vol. 62, 2016, pp. 137-147.

Liu et al., "Efficient Gene Targeting in Zebrafish Mediated by a Zebrafish-Codon-Optimized Cas9 and Evaluation of Off-Targeting Effect", Journal of Genetics and Genomics, vol. 41,, 2014, pp. 43-46.

Lombardo et al., "Gene Editing in Human Stem Cells using Zinc Finger Nucleases and Integrase-Defective Lentiviral Vector Delivery", Nature Biotechnology, vol. 25, No. 11, 2007, pp. 1298-1306.

Makarova et al., "An Updated Evolutionary Classification of CRISPR-Cas Systems", Nature Reviews/Microbiology, vol. 13, No. 11, Nov. 2015, pp. 722-736.

Mali et al., "Cas9 as a Versatile Tool for Engineering Biology", Nature Methods, vol. 10, No. 10, Oct. 1, 2013, pp. 957-963.

Moehle et al., "Targeted Gene Addition into a Specified Location in the Human Genome using Designed Zinc Finger Nucleases", PNAS, vol. 104, No. 9, Feb. 27, 2007, pp. 3055-3060.

Mougiakos, et al., "Characterizing a Thermostable Cas9 for Bacterial Genome Editing and Silencing", Nature Communications, vol. 8, Article 1647, 2017, pp. 1-11.

Palermo et al., "Protospacer Adjacent Motif-Induced Allostery Activates CRISPR-Cas9", Journal of the American Chemical Society, vol. 139, Aug. 2017, pp. 16028-16031.

International Search Report and Written Opinion received for PCT Application No. PCT/US2019/018335, dated Jul. 8, 2019, 22 pages.

Ran et al., "Double Nicking by RNA-Guided CRISPR Cas9 for Enhanced Genome Editing Specificity", Cell, vol. 154, 2013, pp. 1380-1389.

Ran et al., "Genome Engineering using the CRISPR-Cas9 System", Nature Protocols, vol. 8, No. 11, 2013, pp. 2281-2308.

Ran et al., "In Vivo Genome Editing using *Staphylococcus aureus* Cas9", Nature, vol. 520, Apr. 2015, pp. 186-191.

Santiago et al., "Targeted Gene Knockout in Mammalian Cells by using Engineered Zinc-Finger Nucleases", PNAS, vol. 105, No. 15, Apr. 15, 2008, pp. 5809-5814.

Smith et al., "Comparison of Biosequences", Advances in Applied Mathematics, vol. 2, No. 4, 1981, pp. 482-489.

Urnov et al., "Highly Efficient Endogenous Human Gene Correction using Designed Zinc-Finger Nucleases", Nature, vol. 435, Jun. 2, 2005, pp. 646-651.

Yoshioka et al., "Efficient Generation of Human iPSCs by a Synthetic Self-Replicative RNA", Cell Stem Cell, vol. 13, Issue 2, Aug. 1, 2013, pp. 246-254.

Zalatan et al., "Engineering Complex Synthetic Transcriptional Programs with CRISPR RNA Scaffolds", Cell, vol. 160, Issue 1, Jan. 15, 2015, pp. 339-350.

Lange et al., Classical Nuclear Localization Signals: Definition, Function, and Interaction with Importin α, Journal of Biological Chemistry, Feb. 23, 2007, vol. 282, No. 8, pp. 5101-5105.

Makarova et al., "An Updated Evolutionary Classification of CRISPR-Cas Systems" Nature Reviews Microbiology, vol. 13, Nov. 2015, pp. 722-750.

Smith et al., "The Nuclear Localization Signal," Proc. R. Soc. Lond.,1985, B 226, pp. 43-58.

GenBank, "Synthetic Construct mScarlet Gene, Partial cds", GenBank Accession No. KY021423.1, Nov. 28, 2016, 01 page.

International Search Report and Written Opinion received for PCT Application No. PCT/US2020/018145, dated May 28, 2020, pp. 1-12.

Chen et al., "Dynamic Imaging of Genomic Loci in Living Human Cells by an Optimized CRISPR/Cas System", Cell, Dec. 1, 2013, vol. 155, Issue 7, pp. 1479-1491.

Database Geneseq, "Fusion protein constructing linker peptide, SEQ ID 385", retrieved from EBI accession No. GSP:BFR18056; Database accession No. BFR18056, Nov. 1, 2018.

Database Geneseq, "Fusion protein preparation related rigid linker, SEQ 55", retrieved from EBI accession No. GSP:BFZ61813 Database accession No. BFZ61813, Mar. 7, 2019.

Office Action received for Japanese Patent Application No. 2021-547390, dated Oct. 25, 2022, 11 Pages (5 Pages of English translation & 6 Pages of Official copy).

Office Action received for Canadian Patent Application No. 3,129,835 dated Sep. 23, 2022, 5 Pages.

Genbank, "mScarlet-I, partial [synthetic construct]", Genbank Accession No. APD076536.1 Retrieved from Internet URL: https://www.ncbi.nlm.nih.gov/protein/APD76536.1?report=genbank&log$=prottop&blast_rank=3&RID=MYU082US013>, Nov. 28, 2016, 1 Page.

Bindels et al., "mScarlet: A bright monomeric red fluorescent protein for cellular imaging", Nature methods, vol. 14, No. 1, Nov. 21, 2016, pp. 53-56.

Office Action received for Australian Patent Application No. 2020221274, dated Jan. 27, 2023, 5 Pages.

Office Action received for Japanese Patent Application No. 2021-547390 mailing date Mar. 28, 2023, 5 Pages (1 Page of English translation and 4 pages of official copy).

Chen X., et al., "Fusion Protein Linkers: Property, Design and Functionality", Advanced Drug Delivery Reviews, vol. 65, No. 10, Sep. 29, 2012, pp 1357-1369.

Invitation to Respond to Written Opinion received for Singapore Application No. 11202108812S, mailing date May 12, 2023, 11 Pages.

Office Action received for Canadian Patent Application No. 3,129,835 mailing date Nov. 20, 202, 3 Pages.

Office Action received for Chinese Patent Application No. 202080029346.8 mailing date Jan. 11, 2024, 16 Pages (10 Pages of English translation and 6 Pages of official copy).

Examination report received for Australian Patent Application No. 2020221274 mailing date Dec. 21, 2023, 3 Pages.

\* cited by examiner

CRISPR/CAS FUSION PROTEINS AND SYSTEMS

RELATED APPLICATIONS

The present application is a Divisional Application of U.S. application Ser. No. 16/790,399, filed Feb. 13, 2020, which claims the benefit of priority of U.S. Provisional Application No. 62/806,708, filed Feb. 15, 2019, the entirety of each of which is incorporated herein by reference.

FIELD

The present disclosure relates to engineered Cas9 systems, nucleic acids encoding said systems, and methods of using said systems for genome modification.

BACKGROUND

Many different types of peptide linkers have been tested to fuse GFP to Cas9, but typically result in lower activity of the underlying Cas9.

SUMMARY OF THE DISCLOSURE

Among the various aspects of the present disclosure include engineered Cas9 systems.

Other aspects and features of the disclosure are detailed bellow.

SEQUENCE LISTING

Figure 1:
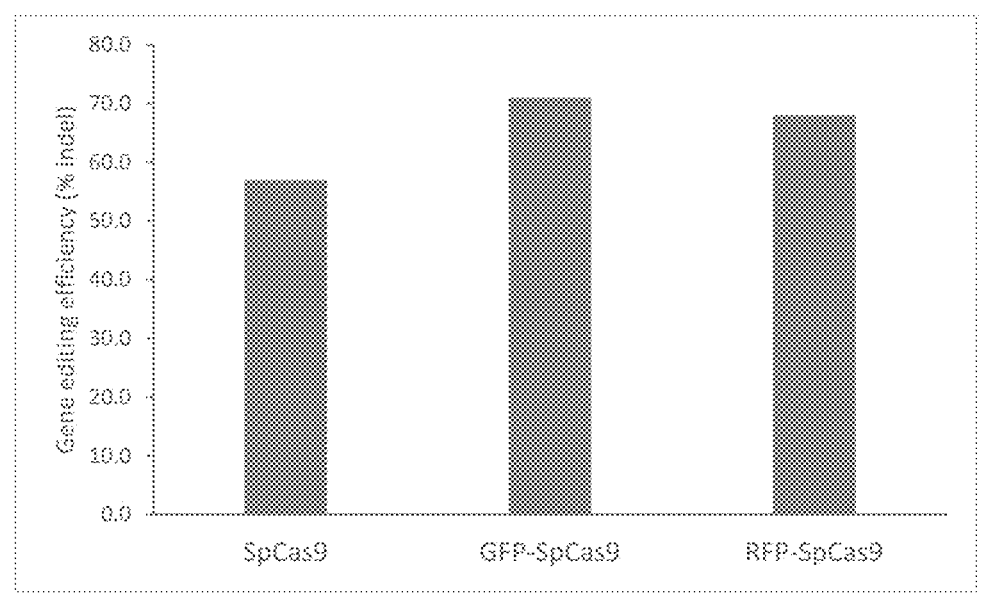
FIG. 1 shows that the Cas9 fusion proteins disclosed herein each retain the editing activity parallel to the level of SpCas9 protein.

The instant application contains a Sequence Listing which has been submitted electronically in ASCII format and is hereby incorporated by reference in its entirety. Said ASCII copy, created on Feb. 9, 2021, is named P19-027_US-DIV1_SL.txt and is 86,319 bytes in size.

DETAILED DESCRIPTION

Fusion of accessory proteins to CRISPR proteins creates a wide range of opportunities to localize various protein functionalities to defined locations within cells. Among other things, peptide linkers which enable fusion of heterologous proteins to CRISPR proteins in ways that preserve CRISPR functionality are disclosed.

(I) Engineered Cas9 Systems

One aspect of the present disclosure provides engineered Cas9 proteins and systems. For example, Cas9-marker fusion proteins are disclosed. In some aspects, systems include engineered Cas9 proteins and engineered guide RNAs, wherein each engineered guide RNA is designed to complex with a specific engineered Cas9 protein. These engineered Cas9 systems do not occur naturally.

(a) Engineered Cas9 Proteins

Cas9 protein is the single effector protein in Type II CRISPR systems, which are present in various bacteria. The engineered Cas9 protein disclosed herein can be from Acaryochloris sp., Acetohalobium sp., Acidaminococcus sp., Acidithiobacillus sp., Acidothermus sp., Akkermansia sp., Alicyclobacillus sp., Allochromatium sp., Ammonifex sp., Anabaena sp., Arthrospira sp., Bacillus sp., Bifidobacterium sp., Burkholderiales sp., Caldicelulosiruptor sp., Campylobacter sp., Candidatus sp., Clostridium sp., Corynebacterium sp., Crocosphaera sp., Cyanothece sp., Exiguobacterium sp., Fibrobacter sp., Finegoldia sp., Francisella sp., Ktedonobacter sp., Lachnospiraceae sp., Lactobacillus sp., Listeria sp., Lyngbya sp., Marinobacter sp., Methanohalobium sp., Microscilla sp., Microcoleus sp., Microcystis sp., Mycoplasma sp., Natranaerobius sp., Neisseria sp., Nitratifractor sp., Nitrosococcus sp., Nocardiopsis sp., Nodularia sp., Nostoc sp., Oenococcus sp., Oscillatoria sp., Parasutterella sp., Pasteurella sp., Parvibaculum sp., Pelotomaculum sp., Petrotoga sp., Polaromonas sp., Prevotella sp., Pseudoalteromonas sp., Ralstonia sp., Rhodospirillum sp., Staphylococcus sp., Streptococcus sp., Streptomyces sp., Streptosporangium sp., Synechococcus sp., Thermosipho sp., Treponema sp., Verrucomicrobia sp., and Wolinella sp.

Exemplary species that the Cas9 protein or other components may be from or derived from include Acaryochloris ssp. (e.g., Acaryochloris marina), Acetohalobium ssp. (e.g., Acetohalobium arabaticum), Acidaminococcus ssp., Acidithiobacillus ssp. (e.g., Acidithiobacillus caldus, Acidithiobacillus ferrooxidans), Acidothermus ssp., Akkermansia ssp., Alicyclobacillus ssp. (e.g., Alicyclobacillus acidocaldarius), Allochromatium ssp. (e.g., Allochromatium vinosum), Ammonifex ssp. (e.g., Ammonifex degensii), Anabaena ssp. (e.g., Anabaena variabilis), Arthrospira ssp. (e.g., Arthrospira maxima, Arthrospira platensis), Bacillus ssp. (e.g., Bacillus pseudomycoides, Bacillus selenitireducens), Bifidobacterium ssp., Burkholderiales ssp. (e.g., Burkholderiales bacterium), Caldicelulosiruptor ssp. (e.g., Caldicelulosiruptor becscii), Campylobacter ssp. (e.g., Campylobacter jejuni, Campylobacter lari), Candidatus ssp., (e.g., Candidatus Desulforudis), Clostridium ssp. (e.g., Clostridium botulinum, Clostridium difficile), Corynebacterium ssp. (e.g., Corynebacterium diphtheria), Crocosphaera ssp. (e.g., Crocosphaera watsonii), Cyanothece ssp., Deltaproteobacterium ssp., Exiguobacterium ssp. (e.g., Exiguobacterium sibiricum), (Fibrobacter ssp. (e.g., Fibrobacter succinogene), Finegoldia ssp. (e.g., Finegoldia magna), Francisella ssp. (e.g., Francisella novicida), Gammaproteobacterium, Ktedonobacter ssp. (e.g., Ktedonobacter racemifer), Lachnospiraceae ssp., Lactobacillus ssp. (e.g., Lactobacillus buchneri, Lactobacillus delbrueckii, Lactobacillus gasseri, Lactobacillus salivarius), Listeria ssp. (e.g., Listeria innocua), Leptotrichia ssp., Lyngbya ssp., Marinobacter ssp., Methanohalobium ssp. (e.g., Methanohalobium evestigatum), Microcoleus ssp. (e.g., Microcoleus chthonoplastes), Microscilla ssp. (e.g., Microscilla marina), Microcystis ssp. (e.g., Microcystis aeruginosa), Mycoplasma spp., Natranaerobius ssp. (e.g., Natranaerobius thermophilus), Neisseria ssp. (e.g., Neisseria cinerea, Neisseria meningitidis), Nitratifractor ssp., Nitrosococcus ssp. (e.g., Nitrosococcus halophilus, Nitrosococcus watsoni), Nocardiopsis ssp. (e.g., Nocardiopsis dassonvillei), Nodularia ssp. (e.g., Nodularia spumigena), Nostoc ssp., Oenococcus ssp., Oscillatoria ssp., Parasutterella ssp., Parvibaculum ssp. (e.g., Parvibaculum lavamentivorans), Pasteurella ssp. (e.g., Pasteurella multocida), Pelotomaculum ssp., (e.g., Pelotomaculum thermopropionicum), Petrotoga ssp. (e.g., Petrotoga mobilis), Planctomyces ssp., Polaromonas ssp. (e.g., Polaromonas naphthalenivorans), Prevotella ssp., Pseudoalteromonas ssp. (e.g., Pseudoalteromonas haloplanktis), Ralstonia ssp., Ruminococcus ssp., Rhodospirillum spp. (e.g., *Rhodospirillum rubrum*), *Staphylococcus* ssp. (e.g., *Staphylococcus aureus*), *Streptococcus* ssp. (e.g., *Streptococcus pasteurianus, Streptococcus pyogenes, Streptococcus thermophilus*), *Sutterella* ssp. (e.g., *Sutterella wadsworthensis*), *Streptomyces* ssp. (e.g., *Streptomyces pristinaespiralis, Streptomyces viridochromogenes, Streptomyces viridochromogenes*), *Streptosporangium* ssp. (e.g., *Streptosporangium roseum, Streptosporangium roseum*), *Synechococcus* ssp., *Thermosipho* ssp. (e.g., *Thermosipho africanus*), *Treponema* ssp. (e.g., *Treponema denticola*), and *Verrucomicrobia* ssp., *Wolinella* ssp. (e.g., *Wolinella succinogenes*), and/or species delineated in bioinformatic surveys of genomic databases such as those disclosed in Makarova, Kira S., et al. "An updated evolutionary classification of CRISPR-Cas systems." Nature Reviews Microbiology 13.11 (2015): 722 and Koonin, Eugene V., Kira S. Makarova, and Feng Zhang. "Diversity, classification and evolution of CRISPR-Cas systems." Current opinion in microbiology 37 (2017): 67-78, each of which is hereby incorporated by reference herein in their entirety.

In some embodiments, the engineered Cas9 protein may be from *Streptococcus pyogenes*. In some embodiments, the engineered Cas9 protein may be from *Streptococcus thermophilus*. In some embodiments, the engineered Cas9 protein may be from *Neisseria meningitidis*. In some embodiments, the engineered Cas9 protein may be from *Staphylococcus aureus*. In some embodiments, the engineered Cas9 protein may be from *Campylobacter jejuni*.

Wild-type Cas9 proteins comprise two nuclease domains, i.e., RuvC and HNH domains, each of which cleaves one strand of a double-stranded sequence. Cas9 proteins also comprise REC domains that interact with the guide RNA (e.g., REC1, REC2) or the RNA/DNA heteroduplex (e.g., REC3), and a domain that interacts with the protospacer-adjacent motif (PAM) (i.e., PAM-interacting domain).

The Cas9 protein can be engineered to comprise one or more modifications (i.e., a substitution of at least one amino acid, a deletion of at least one amino acid, an insertion of at least one amino acid) such that the Cas9 protein has altered activity, specificity, and/or stability.

For example, Cas9 protein can be engineered by one or more mutations and/or deletions to inactivate one or both of the nuclease domains. Inactivation of one nuclease domain generates a Cas9 protein that cleaves one strand of a double-stranded sequence (i.e., a Cas9 nickase). The RuvC domain can be inactivated by mutations such as D10A, D8A, E762A, and/or D986A, and the HNH domain can be inactivated by mutations such as H840A, H559A, N854A, N856A, and/or N863A (with reference to the numbering system of *Streptococcus pyogenes* Cas9, SpyCas9). Inactivation of both nuclease domains generates a Cas9 protein having no cleavage activity (i.e., a catalytically inactive or dead Cas9).

The Cas9 protein can also be engineered by one or more amino acid substitutions, deletions, and/or insertions to have improved targeting specificity, improved fidelity, altered PAM specificity, decreased off-target effects, and/or increased stability. Non-limiting examples of one or more mutations that improve targeting specificity, improve fidelity, and/or decrease off-target effects include N497A, R661A, Q695A, K810A, K848A, K855A, Q926A, K1003A, R1060A, and/or D1135E (with reference to the numbering system of SpyCas9).

In alternative embodiments, the Cas protein may be from a Type I CRISPR/Cas system. In some embodiments, the Cas protein may be a component of the Cascade complex of a Type-I CRISPR/Cas system. For example, the Cas protein may be a Cas3 protein. In some embodiments, the Cas protein may be from a Type III CRISPR/Cas system. In some embodiments, the Cas protein may be from a Type IV CRISPR/Cas system. In some embodiments, the Cas protein may be from a Type V CRISPR/Cas system. In some embodiments, the Cas protein may be from a Type VI CRISPR/Cas system. In some embodiments, the Cas protein may have an RNA cleavage activity. In various embodiments, the Cas protein may be classified as Cas9, Cas12a (a.k.a. Cpf1), Cas12b, Cas12c, Cas12d, Cas12e (a.k.a. CasX), Cas13a, or Cas13b.

(i) Heterologous Domains

The Cas9 protein can be engineered to comprise at least one heterologous domain, i.e., Cas9 is fused to one or more heterologous domains. In situations in which two or more heterologous domains are fused with Cas9, the two or more heterologous domains can be the same or they can be different. The one or more heterologous domains can be fused to the N terminal end, the C terminal end, an internal location, or combination thereof. The fusion can be direct via a chemical bond, or the linkage can be indirect via one or more linkers.

In certain preferred embodiments, the engineered Cas9 proteins described herein include one or more nuclear localization signals (NLS). Non-limiting examples of nuclear localization signals include PKKKRKV (SEQ ID NO:1), PKKKRRV (SEQ ID NO:2), KRPAATKKAGQAKKKK (SEQ ID NO:3), YGRKKRRQRRR (SEQ ID NO:4), RKKRRQRRR (SEQ ID NO:5), PAAKRVKLD (SEQ ID NO:6), RQRRNELKRSP (SEQ ID NO:7), VSRKRPRP (SEQ ID NO:8), PPKKARED (SEQ ID NO:9), PQPKKKPL (SEQ ID NO:10), SALIKKKKKMAP (SEQ ID NO:11), PKQKKRK (SEQ ID NO:12), RKLKKKIKKL (SEQ ID NO:13), REKKKFLKRR (SEQ ID NO:14), KRKGDEVDGVDEVAKKKSKK (SEQ ID NO:15), RKCLQAGMNLEARKTKK (SEQ ID NO:16), NQSSNFGPMKGGNFGGRSSGPYGGGGQYFAK-PRNQGGY (SEQ ID NO:17), and RMRIZFKNKGKD-TAELRRRRVEVSVELRKAKKDEQILKRRNV (SEQ ID NO:18).

In one particular embodiment, the nuclear localization signal is selected from PKKKRKV (SEQ ID NO:1) and PAAKRVKLD (SEQ ID NO:6). In another particular embodiment, the engineered Cas9 protein includes both of PKKKRKV (SEQ ID NO:1) and PAAKRVKLD (SEQ ID NO:6). In another particular embodiment, the engineered Cas9 protein includes at least two of PKKKRKV (SEQ ID NO:1) and at least one of PAAKRVKLD (SEQ ID NO:6). In another particular embodiment, the engineered Cas9 protein includes two of PKKKRKV (SEQ ID NO:1) and one of PAAKRVKLD (SEQ ID NO:6).

In these and other preferred embodiments, the engineered Cas9 proteins include one or more marker domains. Marker domains include fluorescent proteins and purification or epitope tags. Suitable fluorescent proteins include, without limit, green fluorescent proteins (e.g., GFP, eGFP, GFP-2, tagGFP, turboGFP, Emerald, Azami Green, Monomeric Azami Green, CopGFP, AceGFP, ZsGreen1), yellow fluorescent proteins (e.g., YFP, EYFP, Citrine, Venus, YPet, PhiYFP, ZsYellow1), blue fluorescent proteins (e.g., BFP, EBFP, EBFP2, Azurite, mKalama1, GFPuv, Sapphire, T-sapphire), cyan fluorescent proteins (e.g., ECFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), orange fluorescent proteins (e.g., mOrange, mKO, Kusabira-Orange, Monomeric Kusabira-Orange, mTangerine, tdTomato), or combinations thereof. The marker domain can comprise tandem repeats of one or more fluorescent proteins (e.g., Suntag).

In one embodiment, the marker protein is selected from the following:

Marker Protein Sequence

MVSKGEELFTGVVPILVELDGDVNGHKFSVSGEGEGDATYGKLTLKFICT
TGKLPVPWPTLVTTLTYGVQCFSRYPDHMKQHDFFKSAMPEGYVQERTIF
FKDDGNYKTRAEVKFEGDTLVNRIELKGIDFKEDGNILGHKLEYNYNSHN
VYIMADKQKNGIKVNFKIRHNIEDGSVQLADHYQQNTPIGDPVLLPDNH
YLSTQSKLSKDPNEKRDHMVLLEFVTAAGITLGMDELYK (SEQ ID
NO: 19)

MVSKGEAVIKEFMRFKVHMEGSMNGHEFEIEGEGEGRPYEGTQTAKLKVT
KGGPLPFSWDILSPQFMYGSRAFTKHPADIPDYYKQSFPEGFKWERVMNF
EDGGAVTVTQDTSLEDGTLIYKVKLRGTNFPPDGPVMQKKTMGWEASTER
LYPEDGVLKGDIKMALRLKDGGRYLADFKTTYKAKKPVQMPGAYNVDRKL
DITSHNEDYTVVEQYERSEGRHSTGGMDELYK (SEQ ID NO: 20)

Non-limiting examples of suitable purification or epitope tags include 6xHis (SEQ ID NO:22), FLAG® (e.g., SEQ ID NO:21), HA, GST, Myc, SAM, and the like. Non-limiting examples of heterologous fusions which facilitate detection or enrichment of CRISPR complexes include streptavidin (Kipriyanov et al., Human Antibodies, 1995, 6(3):93-101), avidin (Airenne et al., Biomolecular Engineering, 1999, 16(1-4):87-92), monomeric forms of avidin (Laitinen et al., Journal of Biological Chemistry, 2003, 278(6):4010-4014), peptide tags which facilitate biotinylation during recombinant production (Cull et al., Methods in Enzymology, 2000, 326:430-440).

In addition to a nuclear localization signal(s) and a marker protein(s), in various embodiments the engineered Cas9 protein may also include one or more heterologous domains such as a cell-penetrating domain, a marker domain, a chromatin disrupting domain, an epigenetic modification domain (e.g., a cytidine deaminase domain, a histone acetyltransferase domain, and the like), a transcriptional regulation domain, an RNA aptamer binding domain, or a non-Cas9 nuclease domain.

In some embodiments, the one or more heterologous domains can be a cell-penetrating domain. Examples of suitable cell-penetrating domains include, without limit, GRKKRRQRRRPPQPKKKRKV (SEQ ID NO:23), PLSSIFSRIGDPPKKKRKV (SEQ ID NO:24), GALFLGWLGAAGSTMGAPKKKRKV (SEQ ID NO:25), GALFLGFLGAAGSTMGAWSQPKKKRKV (SEQ ID NO:26), KETWWETWWTEWSQPKKKRKV (SEQ ID NO:27), YARAAARQARA (SEQ ID NO:28), THRLPRRRRRR (SEQ ID NO:29), GGRRARRRRRR (SEQ ID NO:30), RRQRRTSKLMKR (SEQ ID NO:31), GWTLNSAGYLLGKINLKALAALAKKIL (SEQ ID NO:32), KALAWEAKLAKALAKALAKHLAKALAKALKCEA (SEQ ID NO:33), and RQIKIWFQNRRMKWKK (SEQ ID NO:34).

In still other embodiments, the one or more heterologous domain can be a chromatin modulating motif (CMM). Non-limiting examples of CMMs include nucleosome interacting peptides derived from high mobility group (HMG) proteins (e.g., HMGB1, HMGB2, HMGB3, HMGN1, HMGN2, HMGN3a, HMGN3b, HMGN4, and HMGN5 proteins), the central globular domain of histone H1 variants (e.g., histone H1.0, H1.1, H1.2, H1.3, H1.4, H1.5, H1.6, H1.7, H1.8, H1.9, and H.1.10), or DNA binding domains of chromatin remodeling complexes (e.g., SWI/SNF (SWItch/Sucrose Non-Fermentable), ISWI (Imitation SWItch), CHD (Chromodomain-Helicase-DNA binding), Mi-2/NuRD (Nucleosome Remodeling and Deacetylase), INO80, SWR1, and RSC complexes. In other embodiments, CMMs also can be derived from topoisomerases, helicases, or viral proteins. The source of the CMM can and will vary. CMMs can be from humans, animals (i.e., vertebrates and invertebrates), plants, algae, or yeast. Non-limiting examples of specific CMMs are listed in the table below. Persons of skill in the art can readily identify homologs in other species and/or the relevant fusion motif therein.

| Protein | Accession No. | Fusion Motif |
|---|---|---|
| Human HMGN1 | P05114 | Full length |
| Human HMGN2 | P05204 | Full length |
| Human HMGN3a | Q15651 | Full length |
| Human HMGN3b | Q15651-2 | Full length |
| Human HMGN4 | O00479 | Full length |
| Human HMGN5 | P82970 | Nucleosome binding motif |
| Human HMGB1 | P09429 | Box A |
| Human histone H1.0 | P07305 | Globular motif |
| Human histone H1.2 | P16403 | Globular motif |
| Human CHD1 | O14646 | DNA binding motif |
| Yeast CHD1 | P32657 | DNA binding motif |
| Yeast ISWI | P38144 | DNA binding motif |
| Human TOP1 | P11387 | DNA binding motif |
| Human herpesvirus 8 LANA | J9QSF0 | Nucleosome binding motif |
| Human CMV IE1 | P13202 | Chromatin tethering motif |
| *M. leprae* DNA helicase | P40832 | HhH binding motif |

In yet other embodiments, the one or more heterologous domains can be an epigenetic modification domain. Non-limiting examples of suitable epigenetic modification domains include those with DNA deamination (e.g., cytidine deaminase, adenosine deaminase, guanine deaminase), DNA methyltransferase activity (e.g., cytosine methyltransferase), DNA demethylase activity, DNA amination, DNA oxidation activity, DNA helicase activity, histone acetyltransferase (HAT) activity (e.g., HAT domain derived from E1A binding protein p300), histone deacetylase activity, histone methyltransferase activity, histone demethylase activity, histone kinase activity, histone phosphatase activity, histone ubiquitin ligase activity, histone deubiquitinating activity, histone adenylation activity, histone deadenylation activity, histone SUMOylating activity, histone deSUMOylating activity, histone ribosylation activity, histone deribosylation activity, histone myristoylation activity, histone demyristoylation activity, histone citrullination activity, histone alkylation activity, histone dealkylation activity, or histone oxidation activity. In specific embodiments, the epigenetic modification domain can comprise cytidine deaminase activity, adenosine deaminase activity, histone acetyltransferase activity, or DNA methyltransferase activity.

In other embodiments, the one or more heterologous domains can be a transcriptional regulation domain (i.e., a transcriptional activation domain or transcriptional repressor domain). Suitable transcriptional activation domains include, without limit, herpes simplex virus VP16 domain, VP64 (i.e., four tandem copies of VP16), VP160 (i.e., ten tandem copies of VP16), NFκB p65 activation domain (p65), Epstein-Barr virus R transactivator (Rta) domain, VPR (i.e., VP64+p65+Rta), p300-dependent transcriptional activation domains, p53 activation domains 1 and 2, heat-shock factor 1 (HSF1) activation domains, Smad4 activation domains (SAD), cAMP response element binding protein (CREB) activation domains, E2A activation domains, nuclear factor of activated T-cells (NFAT) activation domains, or combinations thereof. Non-limiting examples of suitable transcriptional repressor domains include Kruppel-associated box (KRAB) repressor domains, Mxi repressor domains, inducible cAMP early repressor (ICER) domains, YY1 glycine rich repressor domains, Sp1-like repressors, E(spl) repressors, IκB repressors, Sin3 repressors, methyl-CpG binding protein 2 (MeCP2) repressors, or combinations thereof. Transcriptional activation or transcriptional repressor domains can be genetically fused to the Cas9 protein or bound via noncovalent protein-protein, protein-RNA, or protein-DNA interactions.

In further embodiments, the one or more heterologous domains can be an RNA aptamer binding domain (Konermann et al., Nature, 2015, 517(7536):583-588; Zalatan et al., Cell, 2015, 160(1-2):339-50). Examples of suitable RNA aptamer protein domains include MS2 coat protein (MCP), PP7 bacteriophage coat protein (PCP), Mu bacteriophage Com protein, lambda bacteriophage N22 protein, stem-loop binding protein (SLBP), Fragile X mental retardation syndrome-related protein 1 (FXR1), proteins derived from bacteriophage such as AP205, BZ13, f1, f2, fd, fr, ID2, JP34/GA, JP501, JP34, JP500, KU1, M11, M12, MX1, NL95, PP7, φCb5, φCb8r, φCb12r, φCb23r, Qβ, R17, SP-β, TW18, TW19, and VK, fragments thereof, or derivatives thereof.

In yet other embodiments, the one or more heterologous domains can be a non-Cas9 nuclease domain. Suitable nuclease domains can be obtained from any endonuclease or exonuclease. Non-limiting examples of endonucleases from which a nuclease domain can be derived include, but are not limited to, restriction endonucleases and homing endonucleases. In some embodiments, the nuclease domain can be derived from a type II-S restriction endonuclease. Type II-S endonucleases cleave DNA at sites that are typically several base pairs away from the recognition/binding site and, as such, have separable binding and cleavage domains. These enzymes generally are monomers that transiently associate to form dimers to cleave each strand of DNA at staggered locations. Non-limiting examples of suitable type II-S endonucleases include BfiI, BpmI, BsaI, BsgI, BsmBI, BsmI, BspMI, FokI, MboII, and SapI. In some embodiments, the nuclease domain can be a FokI nuclease domain or a derivative thereof. The type II-S nuclease domain can be modified to facilitate dimerization of two different nuclease domains. For example, the cleavage domain of FokI can be modified by mutating certain amino acid residues. By way of non-limiting example, amino acid residues at positions 446, 447, 479, 483, 484, 486, 487, 490, 491, 496, 498, 499, 500, 531, 534, 537, and 538 of FokI nuclease domains are targets for modification. In specific embodiments, the FokI nuclease domain can comprise a first FokI half-domain comprising Q486E, I499L, and/or N496D mutations, and a second FokI half-domain comprising E490K, I538K, and/or H537R mutations.

The one or more heterologous domains can be linked directly to the Cas9 protein via one or more chemical bonds (e.g., covalent bonds), or the one or more heterologous domains can be linked indirectly to the Cas9 protein via one or more linkers.

A linker is a chemical group that connects one or more other chemical groups via at least one covalent bond. Suitable linkers include amino acids, peptides, nucleotides, nucleic acids, organic linker molecules (e.g., maleimide derivatives, N-ethoxybenzylimidazole, biphenyl-3,4',5-tricarboxylic acid, p-aminobenzyloxycarbonyl, and the like), disulfide linkers, and polymer linkers (e.g., PEG). The linker can include one or more spacing groups including, but not limited to alkylene, alkenylene, alkynylene, alkyl, alkenyl, alkynyl, alkoxy, aryl, heteroaryl, aralkyl, aralkenyl, aralkynyl and the like. The linker can be neutral, or carry a positive or negative charge. Additionally, the linker can be cleavable such that the linker's covalent bond that connects the linker to another chemical group can be broken or cleaved under certain conditions, including pH, temperature, salt concentration, light, a catalyst, or an enzyme. In some embodiments, the linker can be a peptide linker. The peptide linker can be a flexible amino acid linker (e.g., comprising small, non-polar or polar amino acids).

In one particular embodiment, the linker is selected from the following:

| Linker Protein Sequence |
|---|
| AEAAAKEAAAKEAAAKEAAAKALEAEAAAKEAAAKEAAAKEAAAKA (SEQ ID NO: 35) |
| SGGSSGGSSGSETPGTSESATPESSGGSSGGS (SEQ ID NO: 36) |

Other non-limiting examples of flexible linkers include LEGGGS (SEQ ID NO:37), TGSG (SEQ ID NO:38), GGSGGGSG (SEQ ID NO:39), (GGGGS)$_{1-4}$ (SEQ ID NO:40), and (Gly)$_{6-8}$ (SEQ ID NO:41). Alternatively, the peptide linker can be a rigid amino acid linker. Such linkers include (EAAAK)$_{1-4}$ (SEQ ID NO:42), A(EAAAK)$_{2-5}$A (SEQ ID NO:43), PAPAP (SEQ ID NO:44), and (AP)$_{6-8}$ (SEQ ID NO:45). Additional examples of suitable linkers are well known in the art and programs to design linkers are readily available (Crasto et al., Protein Eng., 2000, 13(5): 309-312).

In some embodiments, the engineered Cas9 proteins can be produced recombinantly in cell-free systems, bacterial cells, or eukaryotic cells and purified using standard purification means. In other embodiments, the engineered Cas9 proteins are produced in vivo in eukaryotic cells of interest from nucleic acids encoding the engineered Cas9 proteins (see section (II) below).

In embodiments in which the engineered Cas9 protein comprises nuclease or nickase activity, the engineered Cas9 protein can further comprise at least cell-penetrating domain, as well as at least one chromatin disrupting domain. In embodiments in which the engineered Cas9 protein is linked to an epigenetic modification domain, the engineered Cas9 protein can further comprise at least one cell-penetrating domain, as well as at least one chromatin disrupting domain. Furthermore, in embodiments in which the engineered Cas9 protein is linked to a transcriptional regulation domain, the engineered Cas9 protein can further comprise at least one cell-penetrating domain, as well as at least one chromatin disrupting domain and/or at least one RNA aptamer binding domain.

The various fusion protein components can be combined, from N-terminus to C-terminus, in any order. For example, wherein A represents the marker protein, B represents a nuclear localization signal, and C represents the Cas9 protein, the fusion protein can be arranged, from N-terminus to C-terminus, in the following manner: A-B-C; A-C-B; B-A-C; B-C-A; C-A-B; or C-B-A, wherein a linker ("-L-") may be disposed between any two items (e.g., A-L-B-C; A-B-L-C; A-L-B-L-C; and so on).

(b) Engineered Guide RNAs

The engineered guide RNAs is designed to complex with a specific engineered Cas9 protein. A guide RNA comprises (i) a CRISPR RNA (crRNA) that contains a guide sequence at the 5' end that hybridizes with a target sequence and (ii) a transacting crRNA (tracrRNA) sequence that recruits the Cas9 protein. The crRNA guide sequence of each guide RNA is different (i.e., is sequence specific). The tracrRNA sequence is generally the same in guide RNAs designed to complex with a Cas9 protein from a particular bacterial species.

The crRNA guide sequence is designed to hybridize with a target sequence (i.e., protospacer) in a double-stranded sequence. In general, the complementarity between the crRNA and the target sequence is at least 80%, at least 85%, at least 90%, at least 95%, or at least 99%. In specific embodiments, the complementarity is complete (i.e., 100%). In various embodiments, the length of the crRNA guide sequence can range from about 15 nucleotides to about 25 nucleotides. For example, the crRNA guide sequence can be about 15, 16, 17, 18, 19, 20, 21, 22, 23, 24, or 25 nucleotides in length. In specific embodiments, the crRNA is about 19, 20, or 21 nucleotides in length. In one embodiment, the crRNA guide sequence has a length of 20 nucleotides.

The guide RNA comprises repeat sequence that forms at least one stem loop structure, which interacts with the Cas9 protein, and 3' sequence that remains single-stranded. The length of each loop and stem can vary. For example, the loop can range from about 3 to about 10 nucleotides in length, and the stem can range from about 6 to about 20 base pairs in length. The stem can comprise one or more bulges of 1 to about 10 nucleotides. The length of the single-stranded 3' region can vary. The tracrRNA sequence in the engineered guide RNA generally is based upon the coding sequence of wild type tracrRNA in the bacterial species of interest. The wild-type sequence can be modified to facilitate secondary structure formation, increased secondary structure stability, facilitate expression in eukaryotic cells, and so forth. For example, one or more nucleotide changes can be introduced into the guide RNA coding sequence (see Example 3, below). The tracrRNA sequence can range in length from about 50 nucleotides to about 300 nucleotides. In various embodiments, the tracrRNA can range in length from about 50 to about 90 nucleotides, from about 90 to about 110 nucleotides, from about 110 to about 130 nucleotides, from about 130 to about 150 nucleotides, from about 150 to about 170 nucleotides, from about 170 to about 200 nucleotides, from about 200 to about 250 nucleotides, or from about 250 to about 300 nucleotides.

In general, the engineered guide RNA is a single molecule (i.e., a single guide RNA or sgRNA), wherein the crRNA sequence is linked to the tracrRNA sequence. In some embodiments, however, the engineered guide RNA can be two separate molecules. A first molecule comprising the crRNA that contains 3' sequence (comprising from about 6 to about 20 nucleotides) that is capable of base pairing with the 5' end of a second molecule, wherein the second molecule comprises the tracrRNA that contains 5' sequence (comprising from about 6 to about 20 nucleotides) that is capable of base pairing with the 3' end of the first molecule.

In some embodiments, the tracrRNA sequence of the engineered guide RNA can be modified to comprise one or more aptamer sequences (Konermann et al., Nature, 2015, 517(7536):583-588; Zalatan et al., Cell, 2015, 160(1-2):339-50). Suitable aptamer sequences include those that bind adaptor proteins chosen from MCP, PCP, Com, SLBP, FXR1, AP205, BZ13, f1, f2, fd, fr, ID2, JP34/GA, JP501, JP34, JP500, KU1, M11, M12, MX1, NL95, PP7, φCb5, φCb8r, φCb12r, φCb23r, Qβ, R17, SP-β, TW18, TW19, VK, fragments thereof, or derivatives thereof. Those of skill in the art appreciate that the length of the aptamer sequence can vary.

In other embodiments, the guide RNA can further comprise at least one detectable label. The detectable label can be a fluorophore (e.g., FAM, TMR, Cy3, Cy5, Texas Red, Oregon Green, Alexa Fluors, Halo tags, or suitable fluorescent dye), a detection tag (e.g., biotin, digoxigenin, and the like), quantum dots, or gold particles.

The guide RNA can comprise standard ribonucleotides and/or modified ribonucleotides. In some embodiment, the guide RNA can comprise standard or modified deoxyribonucleotides. In embodiments in which the guide RNA is enzymatically synthesized (i.e., in vivo or in vitro), the guide RNA generally comprises standard ribonucleotides. In embodiments in which the guide RNA is chemically synthesized, the guide RNA can comprise standard or modified ribonucleotides and/or deoxyribonucleotides. Modified ribonucleotides and/or deoxyribonucleotides include base modifications (e.g., pseudouridine, 2-thiouridine, N6-methyladenosine, and the like) and/or sugar modifications (e.g., 2'-O-methy, 2'-fluoro, 2'-amino, locked nucleic acid (LNA), and so forth). The backbone of the guide RNA can also be modified to comprise phosphorothioate linkages, boranophosphate linkages, or peptide nucleic acids.

(c) PAM Sequence

In some embodiments, the target sequence may be adjacent to a protospacer adjacent motif (PAM), a short sequence recognized by a CRISPR/Cas9 complex. In some embodiments, the PAM may be adjacent to or within 1, 2, 3, or 4, nucleotides of the 3' end of the target sequence. The length and the sequence of the PAM may depend on the Cas9 protein used. For example, the PAM may be selected from a consensus or a particular PAM sequence for a specific Cas9 protein or Cas9 ortholog, including those disclosed in FIG. 1 of Ran et al., Nature, 520: 186-191 (2015), which is incorporated herein by reference. In some embodiments, the PAM may comprise 2, 3, 4, 5, 6, 7, 8, 9, or 10 nucleotides in length. Non-limiting exemplary PAM sequences include NGG, NGGNG, NG, NAAAAN, NNAAAAW, NNNNACA, GNNNCNNA, and NNNNGATT (wherein N is defined as any nucleotide, and W is defined as either A or T). In some embodiments, the PAM sequence may be NGG. In some embodiments, the PAM sequence may be NGGNG. In some embodiments, the PAM sequence may be NNAAAAW.

It will be understood that different CRISPR proteins recognize different PAM sequences. For example, PAM sequences for Cas9 proteins include 5'-NGG, 5'-NGGNG, 5'-NNAGAAW, 5'-NNNNGATT, 5-NNNNRYAC, 5'-NNNNCAAA, 5'-NGAAA, 5'-NNAAT, 5'-NNNRTA, 5'-NNGG, 5'-NNNRTA, 5'-MMACCA, 5'-NNNNGRY, 5'-NRGNK, 5'-GGGRG, 5'-NNAMMMC, and 5'-NNG, and PAM sequences for Cas12a proteins include 5'-TTN and 5'-TTTV, wherein N is defined as any nucleotide, R is defined as either G or A, W is defined as either A or T, Y is defined an either C or T, and V is defined as A, C, or G. In general, Cas9 PAMs are located 3' of the target sequence, and Cas12a PAMs are located 5' of the target sequence. Various PAM sequences and the CRISPR proteins that recognize them are known in the art, e.g., U.S. Patent Application Publication 2019/0249200; Leenay, Ryan T., et al. "Identifying and visualizing functional PAM diversity across CRISPR-Cas systems." Molecular cell 62.1 (2016): 137-147; and Kleinstiver, Benjamin P., et al. "Engineered CRISPR-Cas9 nucleases with altered PAM specificities."

Nature 523.7561 (2015): 481, each of which are incorporated by reference herein in their entirety.

Additionally or alternatively, the PAM for each of the engineered Cas9 systems disclosed herein is presented below.

| PAM Sequences | |
|---|---|
| Engineered Cas9system | PAM (5'-3')* |
| *Bacillus smithii* Cas9 (BsmCas9) | NNNNCAAA |
| *Lactobacillus rhamnosus* Cas9 (LrhCas9) | NGAAA |
| *Parasutterella excrementihominis* Cas9 (PexCas9) | NGG |
| *Mycoplasma canis* Cas9 (McaCas9) | NNGG |
| *Mycoplasma gallisepticum* Cas9 (MgaCas9) | NNAAT |
| *Akkermansia glycaniphila* Cas9 (AglCas9) | NNNRTA |
| *Akkermansia muciniphila* Cas9 (AmuCas9) | MMACCA |
| *Oenococcus kitaharae* Cas9 (OkiCas9) | NNG |
| *Bifidobacterium bombi* Cas9 (BboCas9) | NNNNGRY |
| *Acidothermus cellulolyticus* Cas9 (AceCas9) | NGG |
| *Alicyclobacillus hesperidum* Cas9 (AheCas9) | NGG |
| *Wolinella succinogenes* Cas9 (WsuCas9) | NGG |
| *Nitratifractor salsuginis* Cas9 (NsaCas9) | NRGNK |
| *Ralstonia syzygi* Cas9 (RsyCas9) | GGGRG |
| *Corynebacterium diphtheria* Cas9 (CdiCas9) | NNAMMMC |

*K is G or T; M is A or C; R is A or G; Y is C or T; and N is A, C, G, or T.

See, e.g., U.S. Patent Application Publication No. 2019/0249200 (hereby incorporated by reference herein in its entirety.

(II) Nucleic Acids

A further aspect of the present disclosure provides nucleic acids encoding the engineered Cas9 systems described above in section (I). The systems can be encoded by single nucleic acids or multiple nucleic acids. The nucleic acids can be DNA or RNA, linear or circular, single-stranded or double-stranded. The RNA or DNA can be codon optimized for efficient translation into protein in the eukaryotic cell of interest. Codon optimization programs are available as freeware or from commercial sources.

In some embodiments, nucleic acid encodes a protein having at least about 75%, at least about 80%, at least about 85%, at least about 90%, at least about 95%, or at least about 99% sequence identity to the amino acid sequence of SEQ ID NO:48, 49, or 50. In certain embodiments, the nucleic acid encoding the engineered Cas9 protein can have at least about 75%, at least about 80%, at least about 85%, at least about 90%, at least about 95%, or at least about 99% sequence identity to the DNA sequence of SEQ ID NO:48, 49, or 50. In certain embodiments, the DNA encoding the engineered Cas9 protein has the DNA sequence of SEQ ID NO:48, 49, or 50. In additional embodiments, the nucleic acid encodes a protein having at least about 75%, at least about 80%, at least about 85%, at least about 90%, at least about 95%, or at least about 99% sequence identity to the amino acid sequence of SEQ ID NO:48, 49, or 50.

In some embodiments, the nucleic acid encoding the engineered Cas9 protein can be RNA. The RNA can be enzymatically synthesized in vitro. For this, DNA encoding the engineered Cas9 protein can be operably linked to a promoter sequence that is recognized by a phage RNA polymerase for in vitro RNA synthesis. For example, the promoter sequence can be a T7, T3, or SP6 promoter sequence or a variation of a T7, T3, or SP6 promoter sequence. The DNA encoding the engineered protein can be part of a vector, as detailed below. In such embodiments, the in vitro-transcribed RNA can be purified, capped, and/or polyadenylated. In other embodiments, the RNA encoding the engineered Cas9 protein can be part of a self-replicating RNA (Yoshioka et al., Cell Stem Cell, 2013, 13:246-254). The self-replicating RNA can be derived from a noninfectious, self-replicating Venezuelan equine encephalitis (VEE) virus RNA replicon, which is a positive-sense, single-stranded RNA that is capable of self-replicating for a limited number of cell divisions, and which can be modified to code proteins of interest (Yoshioka et al., Cell Stem Cell, 2013, 13:246-254).

In other embodiments, the nucleic acid encoding the engineered Cas9 protein can be DNA. The DNA coding sequence can be operably linked to at least one promoter control sequence for expression in the cell of interest. In certain embodiments, the DNA coding sequence can be operably linked to a promoter sequence for expression of the engineered Cas9 protein in bacterial (e.g., *E. coli*) cells or eukaryotic (e.g., yeast, insect, or mammalian) cells. Suitable bacterial promoters include, without limit, T7 promoters, lac operon promoters, trp promoters, tac promoters (which are hybrids of trp and lac promoters), variations of any of the foregoing, and combinations of any of the foregoing. Non-limiting examples of suitable eukaryotic promoters include constitutive, regulated, or cell- or tissue-specific promoters. Suitable eukaryotic constitutive promoter control sequences include, but are not limited to, cytomegalovirus immediate early promoter (CMV), simian virus (SV40) promoter, adenovirus major late promoter, Rous sarcoma virus (RSV) promoter, mouse mammary tumor virus (MMTV) promoter, phosphoglycerate kinase (PGK) promoter, elongation factor (ED1)-alpha promoter, ubiquitin promoters, actin promoters, tubulin promoters, immunoglobulin promoters, fragments thereof, or combinations of any of the foregoing. Examples of suitable eukaryotic regulated promoter control sequences include without limit those regulated by heat shock, metals, steroids, antibiotics, or alcohol. Non-limiting examples of tissue-specific promoters include B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, GPIIb promoter, ICAM-2 promoter, INF-β promoter, Mb promoter, NphsI promoter, OG-2 promoter, SP-B promoter, SYN1 promoter, and WASP promoter. The promoter sequence can be wild type or it can be modified for more efficient or efficacious expression. In some embodiments, the DNA coding sequence also can be linked to a polyadenylation signal (e.g., SV40 polyA signal, bovine growth hormone (BGH) polyA signal, etc.) and/or at least one transcriptional termination sequence. In some situations, the engineered Cas9 protein can be purified from the bacterial or eukaryotic cells.

In still other embodiments, the engineered guide RNA can be encoded by DNA. In some instances, the DNA encoding the engineered guide RNA can be operably linked to a promoter sequence that is recognized by a phage RNA polymerase for in vitro RNA synthesis. For example, the promoter sequence can be a T7, T3, or SP6 promoter sequence or a variation of a T7, T3, or SP6 promoter sequence. In other instances, the DNA encoding the engineered guide RNA can be operably linked to a promoter sequence that is recognized by RNA polymerase III (Pol III) for expression in eukaryotic cells of interest. Examples of suitable Pol III promoters include, but are not limited to, mammalian U6, U3, H1, and 7SL RNA promoters.

In various embodiments, the nucleic acid encoding the engineered Cas9 protein can be present in a vector. In some embodiments, the vector can further comprise nucleic acid encoding the engineered guide RNA. Suitable vectors include plasmid vectors, viral vectors, and self-replicating RNA (Yoshioka et al., Cell Stem Cell, 2013, 13:246-254). In some embodiments, the nucleic acid encoding the complex or fusion protein can be present in a plasmid vector. Non-limiting examples of suitable plasmid vectors include pUC, pBR322, pET, pBluescript, and variants thereof. In other embodiments, the nucleic acid encoding the complex or fusion protein can be part of a viral vector (e.g., lentiviral vectors, adeno-associated viral vectors, adenoviral vectors, and so forth). The plasmid or viral vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. Additional information about vectors and use thereof can be found in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., 3$^{rd}$ edition, 2001.

(III) Eukaryotic Cells

Another aspect of the present disclosure comprises eukaryotic cells comprising at least one engineered Cas9 system as detailed above in section (I) and/or at least one nucleic acid encoding and engineered Cas9 protein and/or engineered guide RNA as detailed above in section (II).

The eukaryotic cell can be a human cell, a non-human mammalian cell, a non-mammalian vertebrate cell, an invertebrate cell, a plant cell, or a single cell eukaryotic organism. Examples of suitable eukaryotic cells are detailed below in section (IV)(c). The eukaryotic cell can be in vitro, ex vivo, or in vivo.

By way of example, in some embodiments, the eukaryotic cell, or a population of eukaryotic cells, is a T-cell, a $CD8^+$ T-cell, a $CD8^+$ naive T cell, a central memory T cell, an effector memory T-cell, a $CD4^+$ T-cell, a stem cell memory T-cell, a helper T-cell, a regulatory T-cell, a cytotoxic T-cell, a natural killer T-cell, a hematopoietic stem cell, a long term hematopoietic stem cell, a short term hematopoietic stem cell, a multipotent progenitor cell, a lineage restricted progenitor cell, a lymphoid progenitor cell, a pancreatic progenitor cell, an endocrine progenitor cell, an exocrine progenitor cell, a myeloid progenitor cell, a common myeloid progenitor cell, an erythroid progenitor cell, a megakaryocyte erythroid progenitor cell, a monocytic precursor cell, an endocrine precursor cell, an exocrine cell, a fibroblast, a hepatoblast, a myoblast, a macrophage, an islet beta-cell, a cardiomyocyte, a blood cell, a ductal cell, an acinar cell, an alpha cell, a beta cell, a delta cell, a PP cell, a cholangiocyte, a retinal cell, a photoreceptor cell, a rod cell, a cone cell, a retinal pigmented epithelium cell, a trabecular meshwork cell, a cochlear hair cell, an outer hair cell, an inner hair cell, a pulmonary epithelial cell, a bronchial epithelial cell, an alveolar epithelial cell, a pulmonary epithelial progenitor cell, a striated muscle cell, a cardiac muscle cell, a muscle satellite cell, a myocyte, a neuron, a neuronal stem cell, a mesenchymal stem cell, an induced pluripotent stem (iPS) cell, an embryonic stem cell, a monocyte, a megakaryocyte, a neutrophil, an eosinophil, a basophil, a mast cell, a reticulocyte, a B cell, e.g. a progenitor B cell, a Pre B cell, a Pro B cell, a memory B cell, a plasma B cell, a gastrointestinal epithelial cell, a biliary epithelial cell, a pancreatic ductal epithelial cell, an intestinal stem cell, a hepatocyte, a liver stellate cell, a Kupffer cell, an osteoblast, an osteoclast, an adipocyte (e.g., a brown adipocyte, or a white adipocyte), a preadipocyte, a pancreatic precursor cell, a pancreatic islet cell, a pancreatic beta cell, a pancreatic alpha cell, a pancreatic delta cell, a pancreatic exocrine cell, a Schwann cell, or an oligodendrocyte, or a population of such cells.

(IV) Methods for Modifying Chromosomal Sequences

A further aspect of the present disclosure encompasses methods for modifying a chromosomal sequence in eukaryotic cells. In general, the methods comprise introducing into the eukaryotic cell of interest at least one engineered Cas9 system as detailed above in section (I) and/or at least one nucleic acid encoding said engineered Cas9 system as detailed above in section (II).

In embodiments in which the engineered Cas9 protein comprises nuclease or nickase activity, the chromosomal sequence modification can comprise a substitution of at least one nucleotide, a deletion of at least one nucleotide, an insertion of at least one nucleotide. In some iterations, the method comprises introducing into the eukaryotic cell one engineered Cas9 system comprising nuclease activity or two engineered Cas9 systems comprising nickase activity and no donor polynucleotide, such that the engineered Cas9 system or systems introduce a double-stranded break in the target site in the chromosomal sequence and repair of the double-stranded break by cellular DNA repair processes introduces at least one nucleotide change (i.e., indel), thereby inactivating the chromosomal sequence (i.e., gene knock-out). In other iterations, the method comprises introducing into the eukaryotic cell one engineered Cas9 system comprising nuclease activity or two engineered Cas9 systems comprising nickase activity, as well as the donor polynucleotide, such that the engineered Cas9 system or systems introduce a double-stranded break in the target site in the chromosomal sequence and repair of the double-stranded break by cellular DNA repair processes leads to insertion or exchange of sequence in the donor polynucleotide into the target site in the chromosomal sequence (i.e., gene correction or gene knock-in).

In embodiments, in which the engineered Cas9 protein comprises epigenetic modification activity or transcriptional regulation activity, the chromosomal sequence modification can comprise a conversion of at least one nucleotide in or near the target site, a modification of at least one nucleotide in or near the target site, a modification of at least one histone protein in or near the target site, and/or a change in transcription in or near the target site in the chromosomal sequence.

(a) Introduction into the Cell

As mentioned above, the method comprises introducing into the eukaryotic cell at least one engineered Cas9 system and/or nucleic acid encoding said system (and optional donor polynucleotide). The at least one system and/or nucleic acid/donor polynucleotide can be introduced into the cell of interest by a variety of means.

In some embodiments, the cell can be transfected with the appropriate molecules (i.e., protein, DNA, and/or RNA). Suitable transfection methods include nucleofection (or electroporation), calcium phosphate-mediated transfection, cationic polymer transfection (e.g., DEAE-dextran or polyethylenimine), viral transduction, virosome transfection, virion transfection, liposome transfection, cationic liposome transfection, immunoliposome transfection, nonliposomal lipid transfection, dendrimer transfection, heat shock transfection, magnetofection, lipofection, gene gun delivery, impalefection, sonoporation, optical transfection, and proprietary agent-enhanced uptake of nucleic acids. Transfection methods are well known in the art (see, e.g., "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., 3rd edition, 2001). In other embodiments, the molecules can be introduced into the cell by microinjection. For example, the molecules can be injected into the cytoplasm or nuclei of the cells of interest. The amount of each molecule introduced into the cell can vary, but those skilled in the art are familiar with means for determining the appropriate amount.

The various molecules can be introduced into the cell simultaneously or sequentially. For example, the engineered Cas9 system (or its encoding nucleic acid) and the donor polynucleotide can be introduced at the same time. Alternatively, one can be introduced first and then the other can be introduced later into the cell.

In general, the cell is maintained under conditions appropriate for cell growth and/or maintenance. Suitable cell culture conditions are well known in the art and are described, for example, in Santiago et al., Proc. Natl. Acad. Sci. USA, 2008, 105:5809-5814; Moehle et al. Proc. Natl. Acad. Sci. USA, 2007, 104:3055-3060; Urnov et al., Nature, 2005, 435:646-651; and Lombardo et al., Nat. Biotechnol., 2007, 25:1298-1306. Those of skill in the art appreciate that methods for culturing cells are known in the art and can and will vary depending on the cell type. Routine optimization may be used, in all cases, to determine the best techniques for a particular cell type.

(b) Optional Donor Polynucleotide

In embodiments in which the engineered Cas9 protein comprises nuclease or nickase activity, the method can further comprise introducing at least one donor polynucleotide into the cell. The donor polynucleotide can be single-stranded or double-stranded, linear or circular, and/or RNA or DNA. In some embodiments, the donor polynucleotide can be a vector, e.g., a plasmid vector.

The donor polynucleotide comprises at least one donor sequence. In some aspects, the donor sequence of the donor polynucleotide can be a modified version of an endogenous or native chromosomal sequence. For example, the donor sequence can be essentially identical to a portion of the chromosomal sequence at or near the sequence targeted by the engineered Cas9 system, but which comprises at least one nucleotide change. Thus, upon integration or exchange with the native sequence, the sequence at the targeted chromosomal location comprises at least one nucleotide change. For example, the change can be an insertion of one or more nucleotides, a deletion of one or more nucleotides, a substitution of one or more nucleotides, or combinations thereof. As a consequence of the "gene correction" integration of the modified sequence, the cell can produce a modified gene product from the targeted chromosomal sequence.

In other aspects, the donor sequence of the donor polynucleotide can be an exogenous sequence. As used herein, an "exogenous" sequence refers to a sequence that is not native to the cell, or a sequence whose native location is in a different location in the genome of the cell. For example, the exogenous sequence can comprise protein coding sequence, which can be operably linked to an exogenous promoter control sequence such that, upon integration into the genome, the cell is able to express the protein coded by the integrated sequence. Alternatively, the exogenous sequence can be integrated into the chromosomal sequence such that its expression is regulated by an endogenous promoter control sequence. In other iterations, the exogenous sequence can be a transcriptional control sequence, another expression control sequence, an RNA coding sequence, and so forth. As noted above, integration of an exogenous sequence into a chromosomal sequence is termed a "knock in."

As can be appreciated by those skilled in the art, the length of the donor sequence can and will vary. For example, the donor sequence can vary in length from several nucleotides to hundreds of nucleotides to hundreds of thousands of nucleotides.

Typically, the donor sequence in the donor polynucleotide is flanked by an upstream sequence and a downstream sequence, which have substantial sequence identity to sequences located upstream and downstream, respectively, of the sequence targeted by the engineered Cas9 system. Because of these sequence similarities, the upstream and downstream sequences of the donor polynucleotide permit homologous recombination between the donor polynucleotide and the targeted chromosomal sequence such that the donor sequence can be integrated into (or exchanged with) the chromosomal sequence.

The upstream sequence, as used herein, refers to a nucleic acid sequence that shares substantial sequence identity with a chromosomal sequence upstream of the sequence targeted by the engineered Cas9 system. Similarly, the downstream sequence refers to a nucleic acid sequence that shares substantial sequence identity with a chromosomal sequence downstream of the sequence targeted by the engineered Cas9 system. As used herein, the phrase "substantial sequence identity" refers to sequences having at least about 75% sequence identity. Thus, the upstream and downstream sequences in the donor polynucleotide can have about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% A sequence identity with sequence upstream or downstream to the target sequence. In an exemplary embodiment, the upstream and downstream sequences in the donor polynucleotide can have about 95% or 100% sequence identity with chromosomal sequences upstream or downstream to the sequence targeted by the engineered Cas9 system.

In some embodiments, the upstream sequence shares substantial sequence identity with a chromosomal sequence located immediately upstream of the sequence targeted by the engineered Cas9 system. In other embodiments, the upstream sequence shares substantial sequence identity with a chromosomal sequence that is located within about one hundred (100) nucleotides upstream from the target sequence. Thus, for example, the upstream sequence can share substantial sequence identity with a chromosomal sequence that is located about 1 to about 20, about 21 to about 40, about 41 to about 60, about 61 to about 80, or about 81 to about 100 nucleotides upstream from the target sequence. In some embodiments, the downstream sequence shares substantial sequence identity with a chromosomal sequence located immediately downstream of the sequence targeted by the engineered Cas9 system. In other embodiments, the downstream sequence shares substantial sequence identity with a chromosomal sequence that is located within about one hundred (100) nucleotides downstream from the target sequence. Thus, for example, the downstream sequence can share substantial sequence identity with a chromosomal sequence that is located about 1 to about 20, about 21 to about 40, about 41 to about 60, about 61 to about 80, or about 81 to about 100 nucleotides downstream from the target sequence.

Each upstream or downstream sequence can range in length from about 20 nucleotides to about 5000 nucleotides. In some embodiments, upstream and downstream sequences can comprise about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2800, 3000, 3200, 3400, 3600, 3800, 4000, 4200, 4400, 4600, 4800, or 5000 nucleotides. In specific embodiments, upstream and downstream sequences can range in length from about 50 to about 1500 nucleotides.

(c) Cell Types

A variety of eukaryotic cells are suitable for use in the methods disclosed herein. For example, the cell can be a human cell, a non-human mammalian cell, a non-mammalian vertebrate cell, an invertebrate cell, an insect cell, a plant cell, a yeast cell, or a single cell eukaryotic organism. In some embodiments, the cell can be a one cell embryo. For example, a non-human mammalian embryo including rat, hamster, rodent, rabbit, feline, canine, ovine, porcine, bovine, equine, and primate embryos. In still other embodiments, the cell can be a stem cell such as embryonic stem cells, ES-like stem cells, fetal stem cells, adult stem cells, and the like. In one embodiment, the stem cell is not a human embryonic stem cell. Furthermore, the stem cells may include those made by the techniques disclosed in WO2003/046141, which is incorporated herein in its entirety, or Chung et al. (Cell Stem Cell, 2008, 2:113-117). The cell can be in vitro (i.e., in culture), ex vivo (i.e., within tissue isolated from an organism), or in vivo (i.e., within an organism). In exemplary embodiments, the cell is a mammalian cell or mammalian cell line. In particular embodiments, the cell is a human cell or human cell line.

By way of example, in some embodiments, the eukaryotic cell, or a population of eukaryotic cells, is a T-cell, a $CD8^+$ T-cell, a $CD8^+$ naive T cell, a central memory T cell, an effector memory T-cell, a $CD4^+$ T-cell, a stem cell memory T-cell, a helper T-cell, a regulatory T-cell, a cytotoxic T-cell, a natural killer T-cell, a hematopoietic stem cell, a long term hematopoietic stem cell, a short term hematopoietic stem cell, a multipotent progenitor cell, a lineage restricted progenitor cell, a lymphoid progenitor cell, a pancreatic progenitor cell, an endocrine progenitor cell, an exocrine progenitor cell, a myeloid progenitor cell, a common myeloid progenitor cell, an erythroid progenitor cell, a megakaryocyte erythroid progenitor cell, a monocytic precursor cell, an endocrine precursor cell, an exocrine cell, a fibroblast, a hepatoblast, a myoblast, a macrophage, an islet beta-cell, a cardiomyocyte, a blood cell, a ductal cell, an acinar cell, an alpha cell, a beta cell, a delta cell, a PP cell, a cholangiocyte, a retinal cell, a photoreceptor cell, a rod cell, a cone cell, a retinal pigmented epithelium cell, a trabecular meshwork cell, a cochlear hair cell, an outer hair cell, an inner hair cell, a pulmonary epithelial cell, a bronchial epithelial cell, an alveolar epithelial cell, a pulmonary epithelial progenitor cell, a striated muscle cell, a cardiac muscle cell, a muscle satellite cell, a myocyte, a neuron, a neuronal stem cell, a mesenchymal stem cell, an induced pluripotent stem (iPS) cell, an embryonic stem cell, a monocyte, a megakaryocyte, a neutrophil, an eosinophil, a basophil, a mast cell, a reticulocyte, a B cell, e.g. a progenitor B cell, a Pre B cell, a Pro B cell, a memory B cell, a plasma B cell, a gastrointestinal epithelial cell, a biliary epithelial cell, a pancreatic ductal epithelial cell, an intestinal stem cell, a hepatocyte, a liver stellate cell, a Kupffer cell, an osteoblast, an osteoclast, an adipocyte (e.g., a brown adipocyte, or a white adipocyte), a preadipocyte, a pancreatic precursor cell, a pancreatic islet cell, a pancreatic beta cell, a pancreatic alpha cell, a pancreatic delta cell, a pancreatic exocrine cell, a Schwann cell, or an oligodendrocyte, or a population of such cells.

Non-limiting examples of suitable mammalian cells or cell lines include human embryonic kidney cells (HEK293, HEK293T); human cervical carcinoma cells (HELA); human lung cells (W138); human liver cells (Hep G2); human U2-OS osteosarcoma cells, human A549 cells, human A-431 cells, and human K562 cells; Chinese hamster ovary (CHO) cells, baby hamster kidney (BHK) cells; mouse myeloma NS0 cells, mouse embryonic fibroblast 3T3 cells (NIH3T3), mouse B lymphoma A20 cells; mouse melanoma B16 cells; mouse myoblast C2C12 cells; mouse myeloma SP2/0 cells; mouse embryonic mesenchymal C3H-10T1/2 cells; mouse carcinoma CT26 cells, mouse prostate DuCuP cells; mouse breast EMT6 cells; mouse hepatoma Hepa1c1c7 cells; mouse myeloma J5582 cells; mouse epithelial MTD-1A cells; mouse myocardial MyEnd cells; mouse renal RenCa cells; mouse pancreatic RIN-5F cells; mouse melanoma X64 cells; mouse lymphoma YAC-1 cells; rat glioblastoma 9L cells; rat B lymphoma RBL cells; rat neuroblastoma B35 cells; rat hepatoma cells (HTC); buffalo rat liver BRL 3A cells; canine kidney cells (MDCK); canine mammary (CMT) cells; rat osteosarcoma D17 cells; rat monocyte/macrophage DH82 cells; monkey kidney SV-40 transformed fibroblast (COS7) cells; monkey kidney CVI-76 cells; African green monkey kidney (VERO-76)

cells. An extensive list of mammalian cell lines may be found in the American Type Culture Collection catalog (ATCC, Manassas, Va.).

(V) Applications

The compositions and methods disclosed herein can be used in a variety of therapeutic, diagnostic, industrial, and research applications. In some embodiments, the present disclosure can be used to modify any chromosomal sequence of interest in a cell, animal, or plant in order to model and/or study the function of genes, study genetic or epigenetic conditions of interest, or study biochemical pathways involved in various diseases or disorders. For example, transgenic organisms can be created that model diseases or disorders, wherein the expression of one or more nucleic acid sequences associated with a disease or disorder is altered. The disease model can be used to study the effects of mutations on the organism, study the development and/or progression of the disease, study the effect of a pharmaceutically active compound on the disease, and/or assess the efficacy of a potential gene therapy strategy.

In other embodiments, the compositions and methods can be used to perform efficient and cost effective functional genomic screens, which can be used to study the function of genes involved in a particular biological process and how any alteration in gene expression can affect the biological process, or to perform saturating or deep scanning mutagenesis of genomic loci in conjunction with a cellular phenotype. Saturating or deep scanning mutagenesis can be used to determine critical minimal features and discrete vulnerabilities of functional elements required for gene expression, drug resistance, and reversal of disease, for example.

In further embodiments, the compositions and methods disclosed herein can be used for diagnostic tests to establish the presence of a disease or disorder and/or for use in determining treatment options. Examples of suitable diagnostic tests include detection of specific mutations in cancer cells (e.g., specific mutation in EGFR, HER2, and the like), detection of specific mutations associated with particular diseases (e.g., trinucleotide repeats, mutations in β-globin associated with sickle cell disease, specific SNPs, etc.), detection of hepatitis, detection of viruses (e.g., Zika), and so forth.

In additional embodiments, the compositions and methods disclosed herein can be used to correct genetic mutations associated with a particular disease or disorder such as, e.g., correct globin gene mutations associated with sickle cell disease or thalassemia, correct mutations in the adenosine deaminase gene associated with severe combined immune deficiency (SCID), reduce the expression of HTT, the disease-causing gene of Huntington's disease, or correct mutations in the rhodopsin gene for the treatment of retinitis pigmentosa. Such modifications may be made in cells ex vivo.

In still other embodiments, the compositions and methods disclosed herein can be used to generate crop plants with improved traits or increased resistance to environmental stresses. The present disclosure can also be used to generate farm animal with improved traits or production animals. For example, pigs have many features that make them attractive as biomedical models, especially in regenerative medicine or xenotransplantation.

In still other embodiments, the compositions and methods disclosed herein can be used to determine chromosome identity and location within a living cell or chemically fixed cell (such as formalin fixation used in formalin-fixed paraffin embedded clinical samples). For example, a CRIPSR complex linked via a peptide sequence disclosed herein to a fluorescent protein maybe targeted in single or multiple copies to a genetic locus, and such complexes detected by microscopy to determine chromosomal locus copy number and/or location. Example genetic loci for tracking might include centromeric regions, telomeric regions, or other repetitive regions of the genome to which multiple copies of a single identical CRISPR complex may bind.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd Ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The term "about" when used in relation to a numerical value, x, for example means x±5%.

As used herein, the terms "complementary" or "complementarity" refer to the association of double-stranded nucleic acids by base pairing through specific hydrogen bonds. The base paring may be standard Watson-Crick base pairing (e.g., 5'-A G T C-3' pairs with the complementary sequence 3'-T C A G-5'). The base pairing also may be Hoogsteen or reversed Hoogsteen hydrogen bonding. Complementarity is typically measured with respect to a duplex region and thus, excludes overhangs, for example. Complementarity between two strands of the duplex region may be partial and expressed as a percentage (e.g., 70%), if only some (e.g., 70%) of the bases are complementary. The bases that are not complementary are "mismatched." Complementarity may also be complete (i.e., 100%), if all the bases in the duplex region are complementary.

As used herein, the term "CRISPR/Cas system" or "Cas9 system" refers to a complex comprising a Cas9 protein (i.e., nuclease, nickase, or catalytically dead protein) and a guide RNA.

The term "endogenous sequence," as used herein, refers to a chromosomal sequence that is native to the cell.

As used herein, the term "exogenous" refers to a sequence that is not native to the cell, or a chromosomal sequence whose native location in the genome of the cell is in a different chromosomal location.

A "gene," as used herein, refers to a DNA region (including exons and introns) encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

The term "heterologous" refers to an entity that is not endogenous or native to the cell of interest. For example, a heterologous protein refers to a protein that is derived from or was originally derived from an exogenous source, such as an exogenously introduced nucleic acid sequence. In some instances, the heterologous protein is not normally produced by the cell of interest.

The term "nickase" refers to an enzyme that cleaves one strand of a double-stranded nucleic acid sequence (i.e., nicks a double-stranded sequence). For example, a nuclease with double strand cleavage activity can be modified by mutation and/or deletion to function as a nickase and cleave only one strand of a double-stranded sequence.

The term "nuclease," as used herein, refers to an enzyme that cleaves both strands of a double-stranded nucleic acid sequence.

The terms "nucleic acid" and "polynucleotide" refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The term "nucleotide" refers to deoxyribonucleotides or ribonucleotides. The nucleotides may be standard nucleotides (i.e., adenosine, guanosine, cytidine, thymidine, and uridine), nucleotide isomers, or nucleotide analogs. A nucleotide analog refers to a nucleotide having a modified purine or pyrimidine base or a modified ribose moiety. A nucleotide analog may be a naturally occurring nucleotide (e.g., inosine, pseudouridine, etc.) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

The terms "polypeptide" and "protein" are used interchangeably to refer to a polymer of amino acid residues.

The terms "target sequence," "target chromosomal sequence," and "target site" are used interchangeably to refer to the specific sequence in chromosomal DNA to which the engineered Cas9 system is targeted, and the site at which the engineered Cas9 system modifies the DNA or protein(s) associated with the DNA.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the GenBank website.

As various changes could be made in the above-described cells and methods without departing from the scope of the invention, it is intended that all matter contained in the above description and in the examples given below, shall be interpreted as illustrative and not in a limiting sense.

EXAMPLES

The following examples illustrate certain aspects of the disclosure.

Example 1

Human Cell Gene Editing Using GFP-SpCas9 and RFP-SpCas9 Fusion Proteins

Human K562 cells (0.35×10$^6$) were transfected with 60 pmol of SpCas9, GFP-SpCas9, or RFP-SpCas9 recombinant protein and 180 pmol of an in vitro transcribed single guide RNA (sgRNA) targeting the human EMX1 locus with the guide sequence 5'-GCUCCCAUCACAUCAACCGG-3' (SEQ ID NO: 65). Transfection was carried out using Nucleofection Solution V and an Amaxa instrument. Cells were maintained at 37° C. and 5% $CO_2$ for three days before harvested for gene editing analysis. Genomic DNA was prepared using QuickExtract DNA extraction solution. Targeted EMX1 region was PCR amplified using primers consisting of target-specific sequences and next generation sequencing (NGS) adaptors. The forward primer is

```
                                      (SEQ ID NO: 46)
5'-TCGTCGGCAGCGTCAGATGTGTATAAGAGACAGNNNNNNAGTCTTCC
CATCAGGCTCTCA-3'
``` and the reverse primer is

```
                                      (SEQ ID NO: 47)
GTCTCGTGGGCTCGGAGATGTGTATAAGAGACAGNNNNNNAGAGTCCAGC
TTGGGCC-3',
``` where the target-specific sequences are underlined, and N represents A, T, G, or C. PCR amplicons were analyzed by NGS using the Illumina MiSeq to determine the editing efficiency of each Cas9 protein. The results displayed in FIG. 1 show that the GFP-SpCas9 and RFP-SpCas9 fusing proteins each retain the editing activity parallel to the level by SpCas9 protein.

Table 1 presents the human codon optimized DNA and protein sequences of engineered Cas9/NLS proteins, wherein the NLS sequences are presented in bold text and the linker between the marker protein and Cas9 is presented in underlined text.

TABLE 1

Engineered Cas9 Systems

Amino acid sequence of GFP-SpCas9 fusion protein
MVSKGEELFTGVVPILVELDGDVNGHKFSVSGEGEGDATYGKLTLKFICT
TGKLPVPWPTLVTTLTYGVQCFSRYPDHMKQHDFFKSAMPEGYVQERTIF
FKDDGNYKTRAEVKFEGDTLVNRIELKGIDFKEDGNILGHKLEYNYNSHN
VYIMADKQKNGIKVNFKIRHNIEDGSVQLADHYQQNTPIGDGPVLLPDNH
YLSTQSKLSKDPNEKRDHMVLLEFVTAAGITLGMDELYKVDAEAAAKEAA
AKEAAAKEAAAKALEAEAAAKEAAAKEAAAKEAAAKAPAAKRVKLDGGGG
STGMDKKYSIGLDIGTNSVGWAVITDEYKVPSKKFKVLGNTDRHSIKKNL
IGALLFDSGETAEATRLKRTARRRYTRRKNRICYLQEIFSNEMAKVDDSF
FHRLEESFLVEEDKKHERHPIFGNIVDEVAYHEKYPTIYHLRKKLVDSTD
KADLRLIYLALAHMIKFRGHFLIEGDLNPDNSDVDKLFIQLVQTYNQLFE
ENPINASGVDAKAILSARLSKSRRLENLIAQLPGEKKNGLFGNLIALSLG
LTPNFKSNFDLAEDAKLQLSKDTYDDDLDNLLAQIGDQYADLFLAAKNLS
DAILLSDILRVNTEITKAPLSASMIKRYDEHHQDLTLLKALVRQQLPEKY
KEIFFDQSKNGYAGYIDGGASQEEFYKFIKPILEKMDGTEELLVKLNRED
LLRKQRTFDNGSIPHQIHLGELHAILRRQEDFYPFLKDNREKIEKILTFR
IPYYVGPLARGNSRFAVVMTRKSEETITPWNFEEVVDKGASAQSFIERMT
NFDKNLPNEKVLPKHSLLYEYFTVYNELTKVKYVTEGMRKPAFLSGEQKK
AIVDLLFKTNRKVTVKQLKEDYFKKIECFDSVEISGVEDRFNASLGTYHD
LLKIIKDKDFLDNEENEDILEDIVLTLTLFEDREMIEERLKTYAHLFDDK
VMKQLKRRRYTGWGRLSRKLINGIRDKQSGKTILDFLKSDGFANRNFMQL
IHDDSLTFKEDIQKAQVSGQGDSLHEHIANLAGSPAIKKGILQTVKVVDE
LVKVMGRHKPENIVIEMARENQTTQKGQKNSRERMKRIEEGIKELGSQIL
KEHPVENTQLQNEKLYLYYLQNGRDMYVDQELDINRLSDYDVDHIVPQSF
LKDDSIDNKVLTRSDKNRGKSDNVPSEEVVKKMKNYWRQLLNAKLITQRK
FDNLTKAERGGLSELDKAGFIKRQLVETRQITKHVAQILDSRMNTKYDEN
DKLIREVKVITLKSKLVSDFRKDFQFYKVREINNYHHANDAYLNAVVGTA
LIKKYPKLESEFVYGDYKVYDVRKMIAKSEQEIGKATAKYFFYSNIMNFF
KTEITLANGEIRKRPLIETNGETGEIVWDKGRDFATVRKVLSMPQVNIVK
KTEVQTGGFSKESILPKRNSDKLIARKKDWDPKKYGGFDSPTVAYSVLVV
AKVEKGKSKKLKSVKELLGITIMERSSFEKNPIDFLEAKGYKEVKKDLII
KLPKYSLFELENGRKRMLASAGELQKGNELALPSKYVNFLYLASHYEKLK
GSPEDNEQKQLFVEQHKHYLDEIIEQISEFSKRVILADANLDKVLSAYNK
HRDKPIREQAENIIHLFTLTNLGAPAAFKYFDTTIDRKRYTSTKEVLDAT
LIHQSITGLYETRIDLSQLGGDEFPKKKRKVGGGGSPKKKRKV
(SEQ ID NO: 48)
Underlined: Linker between GFP and SpCas9
Bold: Nuclear localization signals Amino acid sequence of RFP-SpCas9 fusion protein
MVSKGEAVIKEFMRFKVHMEGSMNGHEFEIEGEGEGRPYEGTQTAKLKVT
KGGPLPFSWDILSPQFMYGSRAFTKHPADIPDYYKQSFPEGFKWERVMNF
EDGGAVTVTQDTSLEDGTLIYKVKLRGTNFPPDGPVMQKKTMGWEASTER
LYPEDGVLKGDIKMALRLKDGGRYLADFKTTYKAKKPVQMPGAYNVDRKL
DITSHNEDYTVVEQYERSEGRHSTGGMDELYKVDSGGSSGGSSGGSETPGT
SESATPESSGGSSGGSPAAKRVKLDGGGGSTGMDKKYSIGLDIGTNSVGW
AVITDEYKVPSKKFKVLGNTDRHSIKKNLIGALLFDSGETAEATRLKRTA
RRRYTRRKNRICYLQEIFSNEMAKVDDSFFHRLEESFLVEEDKKHERHPI
FGNIVDEVAYHEKYPTIYHLRKKLVDSTDKADLRLIYLALAHMIKFRGHF
LIEGDLNPDNSDVDKLFIQLVQTYNQLFEENPINASGVDAKAILSARLSK
SRRLENLIAQLPGEKKNGLFGNLIALSLGLTPNFKSNFDLAEDAKLQLSK
DTYDDDLDNLLAQIGDQYADLFLAAKNLSDAILLSDILRVNTEITKAPLS
ASMIKRYDEHHQDLTLLKALVRQQLPEKYKEIFFDQSKNGYAGYIDGGAS
QEEFYKFIKPILEKMDGTEELLVKLNREDLLRKQRTFDNGSIPHQIHLGE
LHAILRRQEDFYPFLKDNREKIEKILTFRIPYYVGPLARGNSRFAWMTRK
SEETITPWNFEEVVDKGASAQSFIERMTNFDKNLPNEKVLPKHSLLYEYF
TVYNELTKVKYVTEGMRKPAFLSGEQKKAIVDLLFKTNRKVTVKQLKEDY
FKKIECFDSVEISGVEDRFNASLGTYHDLLKIIKDKDFLDNEENEDILED
IVLTLTLFEDREMIEERLKTYAHLFDDKVMKQLKRRRYTGWGRLSRKLIN
GIRDKQSGKTILDFLKSDGFANRNFMQLIHDDSLTFKEDIQKAQVSGQGD
SLHEHIANLAGSPAIKKGILQTVKVVDELVKVMGRHKPENIVIEMARENQ
TTQKGQKNSRERMKRIEEGIKELGSQILKEHPVENTQLQNEKLYLYYLQN
GRDMYVDQELDINRLSDYDVDHIVPQSFLKDDSIDNKVLTRSDKNRGKSD
NVPSEEVVKKMKNYWRQLLNAKLITQRKFDNLTKAERGGLSELDKAGFIK
RQLVETRQITKHVAQILDSRMNTKYDENDKLIREVKVITLKSKLVSDFRK
DFQFYKVREINNYHHANDAYLNAVVGTALIKKYPKLESEFVYGDYKVYDV
RKMIAKSEQEIGKATAKYFFYSNIMNFFKTEITLANGEIRKRPLIETNGE TGEIVWDKGRDFATVRKVLSMPQVNIVKKTEVQTGGFSKESILPKRNSDK
LIARKKDWDPKKYGGFDSPTVAYSVLVVAKVEKGKSKKLKSVKELLGITI
MERSSFEKNPIDFLEAKGYKEVKKDLIIKLPKYSLFELENGRKRMLASAG
ELQKGNELALPSKYVNFLYLASHYEKLKGSPEDNEQKQLFVEQHKHYLDE
IIEQISEFSKRVILADANLDKVLSAYNKHRDKPIREQAENIIHLFTLTNL
GAPAAFKYFDTTIDRKRYTSTKEVLDATLIHQSITGLYETRIDLSQLGGD
EFPKKKRKVGGGGSPKKKRKV (SEQ ID NO: 49)
Underlined: Linker between RFP and SpCas9
Bold: Nuclear localization signals Amino acid sequence of GFP-eSpCas9 fusion protein
MVSKGEELFTGVVPILVELDGDVNGHKFSVSGEGEGDATYGKLTLKFICT
TGKLPVPWPTLVTTLTYGVQCFSRYPDHMKQHDFFKSAMPEGYVQERTIF
FKDDGNYKTRAEVKFEGDTLVNRIELKGIDFKEDGNILGHKLEYNYNSHN
VYIMADKQKNGIKVNFKIRHNIEDGSVQLADHYQQNTPIGDGPVLLPDNH
YLSTQSKLSKDPNEKRDHMVLLEFVTAAGITLGMDELYKVDSGGSSGGSS
GSETPGTSESATPESSGGSSGGSPAAKRVKLDGGGGSTGMDKKYSIGLDI
GTNSVGWAVITDEYKVPSKKFKVLGNTDRHSIKKNLIGALLFDSGETAEA
TRLKRTARRRYTRRKNRICYLQEIFSNEMAKVDDSFFHRLEESFLVEEDK
KHERHPIFGNIVDEVAYHEKYPTIYHLRKKLVDSTDKADLRLIYLALAHM
IKFRGHFLIEGDLNPDNSDVDKLFIQLVQTYNQLFEENPINASGVDAKAI
LSARLSKSRRLENLIAQLPGEKKNGLFGNLIALSLGLTPNFKSNFDLAED
AKLQLSKDTYDDDLDNLLAQIGDQYADLFLAAKNLSDAILLSDILRVNTE
ITKAPLSASMIKRYDEHHQDLTLLKALVRQQLPEKYKEIFFDQSKNGYAG
YIDGGASQEEFYKFIKPILEKMDGTEELLVKLNREDLLRKQRTFDNGSIP
HQIHLGELHAILRRQEDFYPFLKDNREKIEKILTFRIPYYVGPLARGNSR
FAWMTRKSEETITPWNFEEVVDKGASAQSFIERMTNFDKNLPNEKVLPKH
SLLYEYFTVYNELTKVKYVTEGMRKPAFLSGEQKKAIVDLLFKTNRKVTV
KQLKEDYFKKIECFDSVEISGVEDRFNASLGTYHDLLKIIKDKDFLDNEE
NEDILEDIVLTLTLFEDREMIEERLKTYAHLFDDKVMKQLKRRRYTGWGR
LSRKLINGIRDKQSGKTILDFLKSDGFANRNFMQLIHDDSLTFKEDIQKA
QVSGQGDSLHEHIANLAGSPAIKKGILQTVKVVDELVKVMGRHKPENIVI
EMARENQTTQKGQKNSRERMKRIEEGIKELGSQILKEHPVENTQLQNEKL
YLYYLQNGRDMYVDQELDINRLSDYDVDHIVPQSFLADDSIDNKVLTRSD
KNRGKSDNVPSEEVVKKMKNYWRQLLNAKLITQRKFDNLTKAERGGLSEL
DKAGFIKRQLVETRQITKHVAQILDSRMNTKYDENDKLIREVKVITLKSK
LVSDFRKDFQFYKVREINNYHHANDAYLNAVVGTALIKKYPALESEFVYG
DYKVYDVRKMIAKSEQEIGKATAKYFFYSNIMNFFKTEITLANGEIRKAP
LIETNGETGEIVWDKGRDFATVRKVLSMPQVNIVKKTEVQTGGFSKESIL
PKRNSDKLIARKKDWDPKKYGGFDSPTVAYSVLVVAKVEKGKSKKLKSVK
ELLGITIMERSSFEKNPIDFLEAKGYKEVKKDLIIKLPKYSLFELENGRK
RMLASAGELQKGNELALPSKYVNFLYLASHYEKLKGSPEDNEQKQLFVEQ
HKHYLDEIIEQISEFSKRVILADANLDKVLSAYNKHRDKPIREQAENIIH
LFTLTNLGAPAAFKYFDTTIDRKRYTSTKEVLDATLIHQSITGLYETRID
LSQLGGDEFPKKKRKVGGGGSPKKKRKV (SEQ ID NO: 50)
Underlined: Linker between GFP and eSpCas9
Bold: Nuclear localization signals Human codon optimized DNA sequences used to produce the three proteins are as follows:

Human codon optimized GFP-SpCas9 DNA sequence

ATGGTTAGCAAAGGTGAAGAACTGTTTACAGGTGTTGTTCCGATTCTGGT
TGAACTGGATGGTGATGTTAATGGCCACAAATTTTCAGTTAGCGGTGAAG
GCGAAGGTGATGCAACCTATGGTAAACTGACCCTGAAATTTATCTGTACC
ACCGGCAAACTGCCGGTTCCGTGGCCGACACTGGTTACCACACTGACCTA
TGGTGTTCAGTGTTTTAGCCGTTATCCGGATCACATGAAACAGCACGATT
TTTTCAAAAGCGCAATGCCGGAAGGTTATGTTCAAGAACGTACCATCTTC
TTCAAAGATGACGGCAACTATAAAACCCGTGCCGAAGTTAAATTTGAAGG
TGATACCCTGGTGAATCGCATTGAACTGAAAGGCATCGATTTTAAAGAGG
ATGGTAATATCCTGGGCCACAAACTGGAATATAATTATAATAGCCACAAC
GTGTACATCATGGCCGACAAACAGAAAAATGGCATCAAAGTGAACTTCAA
GATCCGCCATAATATTGAAGATGGTTCAGTTCAGCTGGCCGATCATTATC
AGCAGAATACCCCGATTGGTGATGGTCCGGTTCTGCTGCCGGATAATCAT
TATCTGAGCACCCAGAGCAAACTGAGCAAAGATCCGAATGAAAAACGTGA
TCACATGGTGCTGCTGGAATTTGTTACCGCAGCAGGTATTACCTTAGGTA
TGGATGAACTGTATAAAGTCGACGCAGAAGCAGCAGCAAAAGAAGCCGCT
GCCAAAGAAGCGGCAGCGAAAGAGGCAGCCGCAAAAGCACTGGAAGCCGA
GGCTGCGGCTAAAGAGGCTGCTGCAAAAGAAGCAGCCGCTAAAGAAGCTG
CGGCTAAGGCACCGGCAGCAAAACGTGTTAAACTGGACGGTGGTGGTGGT
AGCACCGGTATGGACAAGAATATCAGCATCGGTTTGGATATTGGCACGAA
TAGCGTGGGTTGGGCCGTTATTACCGACGAGTACAAAGTGCCGTCCAAGA
AATTCAAAGTGCTGGGCAATACCGATCGCCATAGCATCAAGAAAAATCTG
ATTGGCGCACTGCTGTTCGACAGCGGTGAGACTGCCGAAGCTACGCGTCT

```
GAAGCGTACGGCGCGTCGTCGCTACACCCGCCGTAAGAACCGTATTTGCT
ATCTGCAAGAAATCTTCAGCAACGAAATGGCCAAAGTTGATGATAGCTTT
TTTCACCGCCTGGAAGAGAGCTTTCTGGTGGAAGAGGATAAGAAACACGA
GCGCCATCCGATTTTTGGTAACATTGTCGATGAAGTGGCATACCATGAGA
AGTACCCGACCATCTACCACCTTCGTAAGAAACTGGTGGACAGCACCGAT
AAAGCTGATCTGCGTCTGATTTACCTGGCGCTGGCCCACATGATTAAGTT
TCGCGGTCATTTTCTGATCGAGGGCGATCTGAATCCGGACAATTCTGATG
TTGACAAGCTGTTTATTCAACTTGTACAGACCTACAACCAGTTGTTCGAA
GAGAACCCGATCAATGCGAGCGGTGTTGATGCCAAAGCAATTCTGAGCGC
ACGCCTGAGCAAATCTCGCCGTTTGGAGAACCTGATTGCACAGCTGCCGG
GTGAGAAGAAAAACGGTCTGTTCGGCAATCTGATTGCACTGTCCCTGGGC
TTGACCCCGAATTTTAAGAGCAACTTCGACCTGGCCGAAGATGCGAAGCT
CCAATTGAGCAAAGCACACCTACGACGATGACCTGGACAATCTGCTGGCCC
AGATTGGCGACCAGTACGCAGATCTGTTCTTGGCTGCGAAAAACCTGAGC
GATGCAATTCTGCTGTCGGACATCCTGCGCGTGAATACGGAAATCACGAA
AGCGCCTCTGAGCGCGTCTATGATCAAGCGCTATGACGAGCACCACCAAG
ATCTGACCCTGCTGAAAGCTCTGGTGAGACAACAATTGCCAGAGAAGTAT
AAAGAAATTTTCTTTGACCAGCAGAAAAACGGCTATGCGGGTTACATTGA
CGGTGGCGCAGCCAAGAAGAGTTCTACAAATTCATTAAGCCTATCCTGG
AGAAAATGGATGGCACCGAAGAACTGCTGGTAAAGCTGAATCGTGAAGAT
CTGCTGCGCAAACAGCGCACTTTTGATAACGGTAGCATTCCGCACCAGAT
CCATCTGGGTGAGTTGCACGCGATTTTGCGTCGCCAGGAAGATTTTTATC
CGTTCTTGAAAGACAACCGTGAGAAAATCGAGAAAATTCTGACGTTCCGT
ATCCCGTATTATGTCGGCCCGCTGGCGCGTGGTAATAGCCGCTTCGCGTG
GATGACCCGCAAATCAGAGGAAACGATTACCCCGTGGAATTTTGAGGAAG
TTGTTGATAAGGGTGCAAGCGCCAGTCGTTCATTGAGCGTATGACCAAC
TTTGACAAGAATTTGCCGAATGAAAAAGTCTTGCCGAAGCACTCTCTGCT
GTACGAGTATTTTACCGTTTACAACGAATTGACCAAGGTTAAATACGTCA
CCGAAGGCATGCGCAAACCGGCCTTCCTGAGCGGCGAGCAGAAAAAAGCA
ATCGTTGACCTCTTGTTTAAGACCAACCGCAAGGTTACGGTCAAACTACT
GAAAGAGGACTATTTCAAGAAAATTGAATGTTTTGACTCCGTAGAGATCT
CCGGTGTTGAGGACCGTTTCAACGCGAGCCTGGGCACCTACCATGATCTG
CTGAAAATTATTAAAGACAAAGATTTTCTGGACAACGAAGAGAACGAAGA
TATTCTGGAAGATATCGTTCTGACCCTGACGCTGTTCGAAGATCGTGAGA
TGATTGAGGAACGTCTGAAAACCTACGCACACTTGTTCGATGACAAAGTT
ATGAAACAGCTGAAGCGTCGTCGTTACACAGGTTGGGGCCGTCTGAGCCG
TAAGCTTATCAATGGTATCCGTGACAAACAGAGCGGTAAGACGATTCTGG
ACTTTCTGAAGTCAGATGGCTTCGCCAATCGCAACTTTATGCAACTGATT
CATGACGACTCTCTGACGTTCAAGGAAGATATCCAAAAGGCACAGGTGAG
CGGTCAGGGTGATAGCCTGCATGAGCATATCGCGAACCTGGCCGGTAGCC
CGGCTATCAAAAAGGGTATCTTACAGACTGTGAAAGTTGTGGATGAATTG
GTTAAGGTTATGGGTCGTCACAAACCGGAAAATATTGTGATCGAGATGGC
ACGTGAAAATCAGACGACGCAAAAGGGTCAAAAAAATTCTCGTGAGCGCA
TGAAACGTATTGAAGAGGGTATCAAGAATTGGGCAGCCAAATTCTGAAA
GAACACCCGGTCGAGAACACCCAGCTGCAAAACGAAAACTGTATTTATA
CTATCTGCAGAACGGTCGTGACATGTACGTGGATCAAGAACTGGACATCA
ATCGTTGAGCGATTACGATGTTGATCATATTGTGCCTCAGAGCTTTCTG
AAAGACGATTCGATCGACAACAAAGTGCTGACCCGTAGCGACAAGAATCG
TGGTAAGAGCGATAACGTGCCGAGCGAAGAAGTCGTTAAGAAAATGAAAA
ACTACTGGCGTCAGCTGCTGAACGCCAAGCTGATTACCCAGCGTAAGTTC
GATAACCTGACGAAAGCCGAGCGTGGAGGCCTGAGCGAGCTGGACAAGGC
CGGCTTTATCAAGCGTCAACTGGTGGAAACCCGTCAGATCACTAAACATG
TGGCACAGATCCTGGACTCCCGCATGAATACGAAATATGACGAGAATGAC
AAGTTGATCCGTGAAGTCAAAGTTATTACGCTGAAAAGCAAACTGGTGTC
CGATTTCCGTAAAGACTTCCAGTTCTATAAAGTCCGTGAAATCAACAACT
ATCATCACGCCCACGATGCGTACTTGAACGCTGTTGTGGCACCGCACTG
ATCAAGAAATACCCTAAGCTCGAAAGCGAGTTTGTCTATGGTGACTATAA
AGTTTACGACGTGCGTAAGATGATCGCCAAGAGCGAGCAAGAAATTGTA
AGGCTACCGCAAAGTACTTTTTCTACAGCAACATCATGAACTTCTTCAAA
ACCGAGATTACCCTGGCGAACGGTGAGATCCGTAAACGGCCGCTGATTGA
GACTAATGGCGAAACGGGCGAGATTGTGTGGGACAAAGGTCGCGATTTCG
CTACGGTTCGTAAGGTCCTGAGCATGCCGCAAGTTAACATTGTCAAGAAA
ACTGAAGTGCAGACGGGTGGCTTTAGCAAAGAATCCATCCTGCCGAAGCG
TAATAGCGATAAACTTATCGCGCGTAAAAAAGACTGGGACCCAAAGAAAT
ATGGCGGCTTTGATAGCCCGACCGTCGCGTATAGCGTGTTAGTGGTCGCG
AAAGTTGAAAAGGGCAAGAGCAAGAAACTGAAGTCCGTCAAAGAACTTCT
GGGTATCACCATCATGGAACGTAGCTCCTTTGAGAAGAACCCGATTGCT
TCTTAGAGGCGAAGGGTTATAAAGAAGTCAAAAAAGACCTGATTATCAAG
CTGCCGAAGTACAGCCTGTTTGAGTTGGAGAATGGTCGTAAGCGCATGCT
GGCGAGCGCGGGTGAGCTGCAAAAGGGCAACGAACTGGCGCTGCCGTCGA
AATACGTGAATTTCCTGTACCTGGCCAGCCACTACGAAAAGCTGAAGGGT
TCTCCGGAAGATAATGAACAAAAACAACTGTTCGTTGAGCAACATAAACA
CTACTTGGACGAAATCATCGAGCAAATTAGCGAATTTAGCAAACGTGTCA
TCCTGGCGGACGCGAATCTGGACAAGGTCCTGTCTGCATACAATAAGCAT
CGCGACAAACCAATTCGTGAGCAAGCGGAGAATATCATCCACCTGTTTAC
GCTGACCAACCTAGGTGCGCCGGCGGCATTCAAGTATTTCGATACGACCA
TCGACCGCAAGCGCTATACCAGCACCAAAGAGGTCCTGGACGCGACCCTG
ATCCACCAGAGCATTACCGGCTTATACGAAACCCGTATTGATTTGAGCCA
ACTGGGTGGCGATGAATTCCCGAAAAAAAAGCGCAAAGTTGGTGGCGGTG
GTAGCCCGAAAAAGAAACGTAAAGTG (SEQ ID NO: 62)
```

Human codon optimized RFP-SpCas9 DNA sequence

```
ATGGTTAGCAAAGGTGAAGCCGTGATTAAAGAATTTATGCGCTTTAAGGT
TCACATGGAAGGTAGCATGAATGGCCATGAATTTGAAATTGAAGGTGAAG
GCGAAGGTCGTCCGTATGAAGGCACCCAGACCGCAAAACTGAAAGTTACC
AAAGGTGGTCCGCTGCCGTTTAGCTGGGATATTCTGAGTCCGCAGTTTAT
GTATGGTAGCCGTGCATTTACCAAACATCCGGCAGATATTCCGGATTATT
ACAAACAGAGCTTTCCGGAAGGTTTTAAATGGGAACGTGTGATGAATTTT
GAAGATGGTGGTCAGTTACCGTTACACAGGATACCAGCCTGGAAGATGG
CACCCTGATCTATAAAGTTAAACTGCGTGGCACCAATTTTCCGCCTGATG
GTCCGGTTATGCAGAAAAAAACAATGGGTTGGGAAGCAAGCACCGAACGT
CTGTATCCTGAAGATGGCGTTCTGAAAGGTGATATCAAAATGGCACTGCG
TCTGAAAGATGGCGGTCGTTATCTGGCAGATTTCAAAACCACCTATAAAG
CCAAAAAACCTGTTCAGATGCCTGGTGCCTATATAGTTGATCGTAAACTG
GATATTACCAGCCACAACGAAGATTATACCGTTGTGGAACAGTATGAACG
TAGCGAAGGCCGTCATAGCACAGGTGGTATGGATGAACTGTATAAAGTCG
ACAGCGGTGGTAGCAGCGGTGGTTCAAGCGGTAGCGAAACACCGGGTACA
AGCGAAAGCGCAACACCGGAAAGCAGTGGTGGTAGTTCAGGTGGTAGTCC
GGCAGCAAAACGTGTGAAACTGGATGGCGGTGGCGTAGCACCGGTATGG
ACAAGAAATACAGCATCGGTTTGGATATTGGCACGAATAGCGTGGGTTGG
GCCGTTATTACCGACGAGTACAAAGTGCCGTCCAAGAAATTCAAAGTGCT
GGGCAATACCGATCGCCATAGCATCAAGAAAAATCTGATTGGCGCACTGC
TGTTCGACAGCGGTGAGACTGCCGAAGCTACGCGTCTGAAGCGTACGGCG
CGTCGTCGCTACACCCGCCGTAAGAACCGTATTTGCTATCTGCAAGAAAT
CTTCAGCAACGAAATGGCCAAAGTTGATGATAGCTTTTTTCACCGCCTGG
AAGAGAGCTTTCTGGTGGAAGAGGATAAGAAACACGAGCGCCATCCGATC
TTTGGTAACATTGTCGATGAAGTGGCATACCATGAGAAGTACCCGACCAT
CTACCACCTTCGTAAGAAACTGGTGGACAGCACCGATAAAGCTGATCTGC
GTCTGATTTACCTGGCGCTGGCCCACATGATTAAGTTTCGCGGTCATTTT
CTGATCGAGGGCGATCTGAATCCGGACAATTCTGATGTTGACAAGCTGTT
TATTCAACTTGTACAGACCTACAACCAGTTGTTCGAAGAACCCGATCA
ATGCGAGCGGTGTTGATGCCAAAGCAATTCTGAGCGCACGCCTGAGCAAA
TCTCGCCGTTTGGAGAACCTGATTGCACAGCTGCCGGGTGAGAAGAAAAA
CGGTCTGTTCGGCAATCTGATTGCACTGTCCCTGGGCTTGACCCCGAATT
TTAAGAGCAACTTCGACCTGGCCGAAGATGCGAAGCTCCAATTGAGCAAA
GACACCTACGACGATGACCTGGACAATCTGCTGGCCCAGATTGGCGACCA
GTACGCAGATCTGTTCTTGGCTGCGAAAAACCTGAGCGATGCAATTCTGC
TGTCGGACATCCTGCGCGTGAATACGGAAATCACGAAAGCGCCTCTGAGC
GCGTCTATGATCAAGCGCTATGACGAGCACCACCAAGATCTGACCCTGCT
GAAAGCTCTGGTGAGACAACAATTGCCAGAGAAGTATAAAGAAATTTTCT
TTGACCAGAGCAAAAACGGCTATGCGGGTTACATTGACGGTGGCGCAGC
CAAGAAGAGTTCTACAAATTCATTAAGCCTATCCTGGAGAAAATGGATGG
CACCGAAGAACTGCTGGTAAAGCTGAATCGTGAAGATCTGCTGCGCAAAC
AGCGCACTTTTGATAACGGTAGCATTCCGCACCAGATCCATCTGGGTGAG
TTGCACGCGATTTTGCGTCGCCAGGAAGATTTTTATCCGTTCTTGAAAGA
CAACCGTGAGAAAATCGAGAAAATTCTGACGTTCCGTATCCCGTATTATG
TCGGCCCGCTGGCGCGTGGTAATAGCCGCTTCGCGTGGATGACCCGCAAA
TCAGAGGAAACGATTACCCCGTGGAATTTTGAGGAAGTTGTTGATAAGGG
TGCAAGCGCGCAGTCGTTCATTGAGCGTATGACCAACTTTGACAAGAATT
TGCCGAATGAAAAAGTCTTGCCGAAGCACTCTCTGCTGTACGAGTATTTT
ACCGTTTACAACGAATTGACCAAGGTTAAATACGTCACCGAAGGCATGCG
CAAACCGGCCTTCCTGAGCGGCGAGCAGAAAAAAGCAATCGTTGACCTCT
TGTTTAAGACCAACCGCAAGGTTACGGTCAAACAACTGAAAGAGGACTAT
TTCAAGAAAATTGAATGTTTTGACTCCGTAGAGATCTCCGGTGTTGAGGA
CCGTTTCAACGCGAGCCTGGGCACCTACCATGATCTGCTGAAAATTATTA
AAGACAAAGATTTTCTGGACAACGAAGAGAACGAAGATATTCTGGAAGAT
ATCGTTCTGACCCTGACGCTGTTCGAAGATCGTGAGATGATTGAGGAACG
TCTGAAAACCTACGCACACTTGTTCGATGACAAAGTTATGAAACAGCTGA
AGCGTCGTCGTTACACAGGTTGGGGCCGTCTGAGCCGTAAGCTTATCAAT
GGTATCCGTGACAAACAGAGCGGTAAGACGATTCTGGACTTTCTGAAGTC
AGATGGCTTCGCCAATCGCAACTTTATGCAACTGATTCATGACGACTCTC
TGACGTTCAAGGAAGATATCCAAAAGGCACAGGTGAGCGGTCAGGGTGAT
AGCCTGCATGAGCATATCGCGAACCTGGCGGTAGCCCGGCTATCAAAAA
GGGTATCTTACAGACTGTGAAAGTTGTGGATGAATTGGTTAAGGTTATGG
GTCGTCACAAACCGGAAAATATTGTGATCGAGATGGCACGTGAAAATCAG
ACGACGCAAAAGGGTCAAAAAAATTCTCGTGAGCGCATGAAACGTATTGA
AGAGGGTATCAAGAATTGGGCAGCCAAATTCTGAAAGAACACCCGGTCG
AGAACACCCAGCTGCAAAACGAAAACTGTATTTATACTATCTGCAGAAC
GGTCGTGACATGTACGTGGATCAAGAACTGGACATCAATCGTTTGAGCGA
TTACGATGTTGATCATATTGTGCCTCAGAGCTTTCTGAAAGACGATTCGA
TCGACAACAAAGTGCTGACCCGTAGCGACAAGAATCGTGGTAAGAGCGAT
AACGTGCCGAGCGAAGAAGTCGTTAAGAAAATGAAAAACTACTGGCGTCA
GCTGCTGAACGCCAAGCTGATTACCCAGCGTAAGTTCGATAACCTGACGA
AAGCCGAGCGTGGAGGCCTGAGCGAGCTGGACAAGGCCGGCTTTATCAAG
CGTCAACTGGTGGAAACCCGTCAGATCACTAAACATGTGGCACAGATCCT
```

```
GGACTCCCGCATGAATACGAAATATGACGAGAATGACAAGTTGATCCGTG
AAGTCAAAGTTATTACGCTGAAAAGCAAACTGGTGTCCGATTTCCGTAAA
GACTTCCAGTTCTATAAAGTCCGTGAAATCAACAACTATCATCACGCCCA
CGATGCGTACTTGAACGCTGTTGTGGGCACCGCACTGATCAAGAAATACC
CTAAGCTCGAAAGCGAGTTTGTCTATGGTGACTATAAAGTTTACGACGTG
CGTAAGATGATCGCCAAGAGCGAGCAAGAAATTGGTAAGGCTACCGCAAA
GTACTTTTTCTACAGCAACATCATGAACTTCTTCAAAACCGAGATTACCC
TGGCGAACGGTGAGATCCGTAAACGGCCGCTGATTGAGACTAATGGCGAA
ACGGGCGAGATTGTGTGGGACAAGGGTCGCGATTTCGCTACGGTTCGTAA
GGTCCTGAGCATGCCGCAAGTTAACATTGTCAAGAAAACTGAAGTGCAGA
CGGGTGGCTTTAGCAAAGAATCCATCCTGCCGAAGCGTAATAGCGATAAA
CTTATCGCGCGTAAAAAAGACTGGGACCCAAAGAAATATGGCGGCTTTGA
TAGCCCGACCGTCGCGTATAGCGTGTTAGTGGTCGCGAAAGTTGAAAAGG
GCAAGAGCAAGAAACTGAAGTCCGTCAAAGAACTTCTGGGTATCACCATC
ATGGAACGTAGCTCCTTTGAGAAGAACCCGATTGACTTCTTAGAGGCGAA
GGGTTATAAAGAAGTCAAAAAAGACCTGATTATCAAGCTGCCGAAGTACA
GCCTGTTTGAGTTGGAGAATGGTCGTAAGCGCATGCTGGCGAGCGCGGGT
GAGCTGCAAAAGGGCAACGAACTGGCGCTGCCGTCGAAATACGTCAATTT
TCTGTACCTGGCCAGCCACTACGAAAAGCTGAAGGGTTCTCCGGAAGATA
ACGAACAAAAGCAACTGTTCGTTGAGCAACATAAACACTACTTGGACGAA
ATCATCGAGCAAATTAGCGAATTTAGCAAACGTGTCATCCTGGCGGACGC
GAATCTGGACAAGGTCCTGTCTGCATACAATAAGCATCGCGACAAACCAA
TTCGTGAGCAAGCGGAGAATATCATCCACCTGTTTACGCTGACCAACCTA
GGTGCGCCGGCGGCATTCAAGTATTTCGATACGACCATCGACCGCAAGCG
CTATACCAGCACCAAAGAGGTCCTGGACGCGACCCTGATCCACCAGAGCA
TTACCGGCTTATACGAAACCCGTATTGATTTGAGCCAACTGGGTGGCGAT
GAATTCCCGAAAAAAAAGCGCAAAGTTGGTGGCGGTGGTAGCCCGAAAAA
GAAACGTAAAGTG (SEQ ID NO: 63)

Human codon optimized GFP-eSpCas9 DNA sequence

ATGGTTAGCAAAGGTGAAGAACTGTTTACAGGTGTTGTTCCGATTCTGGT
TGAACTGGATGGTGATGTTAATGGCCACAAATTTTCAGTTAGCGGTGAAG
GCGAAGGTGATGCAACCTATGGTAAACTGACCCTGAAATTTATCTGTACC
ACCGGCAAACTGCCGGTTCCGTGGCCGACACTGGTTACCACACTGACCTA
TGGTGTTCAGTGTTTTAGCCGTTATCCGGATCACATGAAACAGCACGATT
TTTTCAAAAGCGCAATGCCGGAAGGTTATGTTCAAGAACGTACCATCTTC
TTCAAAGATGACGGCAACTATAAAACCCGTGCCGAAGTTAAATTTGAAGG
TGATACCCTGGTGAATCGCATTGAACTGAAAGGCATCGATTTTAAAGAGG
ATGGTAATATCCTGGGCCACAAACTGGAATATAATTATAATAGCCACAAC
GTGTACATCATGGCCGACAAACAGAAAAATGGCATCAAAGTGAACTTCAA
GATCCGCCATAATATTGAAGATGGTTCAGTTCAGCTGGCCGATCATTATC
AGCAGAATACCCCGATTGGTGATGGTCCGGTTCTGCTGCCGGATAATCAT
TATCTGAGCACCCAGAGCAAACTGAGCAAAGATCCGAATGAAAAACGTGA
TCACATGGTGCTGCTGGAATTTGTTACCGCAGCAGGTATTACCTTAGGTA
TGGATGAACTGTATAAAGTCGACAGCGGTGGTAGCAGCGGTGGTTCAAGC
GGTAGCGAAACACCGGGTACAAGCGAAAGCGCAACACCGGAAGACAGTGG
TGGTAGCTCAGGTGGTAGTCCGGCAGCAAAACGTGTTAAACTGGACGGTG
GTGGTGGTAGCACCGGTATGGACAAGAAATACAGCATCGGTTTGGATATT
GGCACGAATAGCGTGGGTTGGGCCGTTATTACCGACGAGTACAAAGTGCC
GTCCAAGAAATTCAAAGTGCTGGGCAATACCGATCGCCATAGCATCAAGA
AAAATCTGATTGGCGCACTGCTGTTCGACAGCGGTGAGACTGCCGAAGCT
ACGCGTCTGAAGCGTACGGCGCGTCGTCGCTACACCCGCCGTAAGAACCG
TATTTGCTATCTGCAAGAAATCTTCAGCAACGAAATGGCCAAAGTTGATG
ATAGCTTTTTTCACCGCCTGGAAGAGAGCTTTCTGGTGGAAGAGGATAAG
AAACACGAGCGCCATCCGATTTTTGGTAACATTGTCGATGAAGTGGCATA
CCATGAGAAGTACCCGACCATCTACCACCTTCGTAAGAAACTGGTGGACA
GCACCGATAAGCTGATCTGCGTCTGATTTACCTGGCGCTGGCCCACATG
ATTAAGTTTCGCGGTCATTTTCTGATCGAGGGCGATCTGAATCCGGACAA
TTCTGATGTTGACAAGCTGTTTATTCAACTTGTACAGACCTACAACCAGT
TGTTCGAAGAGAACCCGATCAATGCGAGCGGTGTTGATGCCAAAGCAATT
CTGAGCGCACGCCTGAGCAAATCTCGCCGTTTGGAGAACCTGATTGCACA
GCTGCCGGGTGAGAAGAAAAACGGTCTGTTCGGCAATCTGATTGCACTGT
CCCTGGGCTTGACCCCGAATTTTAAGAGCAACTTCGACCTGGCCGAAGAT
GCGAAGCTCCAATTGAGCAAAGACACCTACGACGATGACCTGGACAATCT
GCTGGCCCAGATTGGCGACCAGTACGCAGATCTGTTCTTGGCTGCGAAAA
ACCTGAGCGATGCAATTCTGCTGTCGGACATCCTGCGCGTGAATACGGAA
ATCACGAAAGCGCCTCTGAGCGCGTCTATGATCAAGCGCTATGACGAGCA
CCACCAAGATCTGACCCTGCTGAAAGCTCTGGTGAGACAACAATTGCCAG
AGAAGTATAAAGAAATTTTCTTTGACCAGAGCAAAAACGGCTATGCGGGT
TACATTGACGGTGGCGCCAGCCAAGAGAGTTCTACAAATTCATTAAGCC
TATCCTGGAGAAAATGGATGGCACCGAAGAACTGCTGGTAAAGCTGAATC
GTGAAGATCTGCTGCGCAAACAGCGCACTTTTGATAACGGTAGCATTCCG
CACCAGATCCATCTGGGTGAGTTGCACGCGATTTTGCGTCGCCAGGAAGA
TTTTTATCCGTTCTTGAAAGACAACCGTGAGAAAATCGAGAAATTCTGA
CGTTCCGTATCCCGTATTATGTCGGCCCGCTGGCGCGTGGTAATAGCCGC
TTCGCGTGGATGACCCGCAAATCAGAGGAAACGATTACCCGTGGAATTT
TGAGGAAGTTGTTGATAAGGGTGCAAGCGCGCAGTCGTTCATTGAGCGTA
TGACCAACTTTGACAAGAATTTGCCGAATGAAAAAGTCTTGCCGAAGCAC
```

```
TCTCTGCTGTACGAGTATTTTACCGTTTACAACGAATTGACCAAGGTTAA
ATACGTCACCGAAGGCATGCGCAAACCGGCCTTCCTGAGCGGCGAGCAGA
AAAAAGCAATCGTTGACCTCTTGTTTAAGACCAACCGCAAGGTTACGGTC
AAACAACTGAAAGAGGACTATTTCAAGAAAATTGAATGTTTTGACTCCGT
AGAGATCTCCGGTGTTGAGGACCGTTTCAACGCGAGCCTGGGCACCTACC
ATGATCTGCTGAAAATTATTAAAGACAAAGATTTTCTGGACAACGAAGAG
AACGAAGATATTCTGGAAGATATCGTTCTGACCCTGACGCTGTTCGAAGA
TCGTGAGATGATTGAGGAACGTCTGAAAACCTACGCACACTTGTTCGATG
ACAAAGTTATGAAACAGCTGAAGCGTCGTCGTTACACAGGTTGGGGCCGT
CTGAGCCGTAAGCTTATCAATGGTATCCGTGACAAACAGAGCGGTAAGAC
GATTCTGGACTTTCTGAAGTCAGATGGCTTCGCCAATCGCAACTTTATGC
AACTGATTCATGACGACTCTCTGACGTTCAAGGAAGATATCCAAAAGGCA
CAGGTGAGCGGTCAGGGTGATAGCCTGCATGAGCATATCGCGAACCTGGC
GGGTAGCCCGGCTATCAAAAAGGGTATCTTACAGACTGTGAAAGTTGTGG
ATGAATTGGTTAAGGTTATGGGTCGTCACAAACCGGAAAATATTGTGATC
GAGATGGCACGTGAAAATCAGACGACGCAAAAGGGTCAAAAAAATTCTCG
TGAGCGCATGAAACGTATTGAAGAGGGTATCAAAGAATTGGGCAGCCAAA
TTCTGAAAGAACACCCGGTCGAGAACACCCAGCTGCAAAACGAAAAACTG
TATTTATACTATCTGCAGAACGGTCGTGACATGTACGTGGATCAAGAACT
GGACATCAATCGTTTGAGCGATTACGATGTTGATCATATTGTGCCTCAGA
GCTTTCTGGCCGACGATTCGATCGACAACAAAGTGCTGACCCGTAGCGAC
AAGAATCGTGGTAAGAGCGATAACGTGCCGAGCGAAGAAGTCGTTAAGAA
AATGAAAAACTACTGGCGTCAGCTGCTGAACGCCAAGCTGATTACCCAGC
GTAAGTTCGATAACCTGACGAAAGCCGAGCGTGGAGGCCTGAGCGAGCTG
GACAAGGCCGGCTTTATCAAGCGTCAACTGGTGGAAACCCGTCAGATCAC
TAAACATGTGGCACAGATCCTGGACTCCCGCATGAATACGAAATATGATC
AGAATGACAAGTTGATCCGTGAAGTCAAAGTTATTACGCTGAAAAGCAAA
CTGGTGTCCGATTTCCGTAAAGACTTCCAGTTCTATAAAGTCCGTGAAAT
CAACAACTATCATCACGCCCACGATGCGTACTTGAACGCTGTTGTGGGCA
CCGCACTGATCAAGAAATACCCTGCACTCGAAAGCGAGTTTGTCTATGGT
GACTATAAAGTTTACGACGTGCGTAAGATGATCGCCAAGAGCGAGCAAGA
AATTGGTAAGGCTACCGCAAAGTACTTTTTCTACAGCAACATCATGAACT
TCTTCAAAACCGAGATTACCCTGGCGAACGGTGAGATCCGTAAAGCGCCG
CTGATTGAGACTAATGGCGAAACGGGCGAGATTGTGTGGGACAAGGGTCG
CGATTTCGCTACGGTTCGTAAGGTCCTGAGCATGCCGCAAGTTAACATTG
TCAAGAAAACTGAAGTGCAGACGGGTGGCTTTAGCAAAGAATCCATCCTG
CCGAAGCGTAATAGCGATAAACTTATCGCGCGTAAAAAAGACTGGGACCC
AAAGAAATATGGCGGCTTTGATAGCCCGACCGTCGCGTATAGCGTGTTAG
TGGTCGCGAAAGTTGAAAAGGGCAAGAGCAAGAAACTGAAGTCCGTCAAA
GAACTTCTGGGTATCACCATCATGGAACGTAGCTCCTTTGAGAAGAACCC
GATTGACTTCTTAGAGGCGAAGGGTTATAAAGAAGTCAAAAAAGACCTGA
TTATCAAGCTGCCGAAGTACAGCCTGTTTGAGTTGGAGAATGGTCGTAAG
CGCATGCTGGCGAGCGCGGGTGAGCTGCAAAAGGGCAACGAACTGGCGCT
GCCGTCGAAATACGTCAATTTTCTGTACCTGGCCAGCCACTACGAAAAGC
TGAAGGGTTCTCCGGAAGATAACGAACAAAAGCAACTGTTCGTTGAGCAA
CATAAACACTACTTGGACGAAATCATCGAGCAAATTAGCGAATTTAGCAA
ACGTGTCATCCTGGCGGACGCGAATCTGGACAAGGTCCTGTCTGCATACA
ATAAGCATCGCGACAAACCAATTCGTGAGCAAGCGGAGAATATCATCCAC
CTGTTTACGCTGACCAACCTAGGTGCGCCGGCGGCATTCAAGTATTTCGA
TACGACCATCGACCGCAAGCGCTATACCAGCACCAAAGAGGTCCTGGACG
CGACCCTGATCCACCAGAGCATTACCGGCTTATACGAAACCCGTATTGAT
TTGAGCCAACTGGGTGGCGATGAATTCCCGAAAAAAAAGCGCAAAGTTGG
TGGCGGTGGTAGCCCGAAAAAGAAACGTAAAGTG (SEQ ID NO: 64)
```

Example 2

Editing Efficiency Comparison with Commercial Products

Two commercial GFP-SpCas9 fusion protein products, GenCrispr NLS-Cas9-EGFP Nuclease and ArciTect Cas9-eGFP Nuclease, were purchased from GenScript (Piscataway, N.J.) and Stemcell Technologies (Vancouver, Canada), respectively. Human U2OS cells ($0.2 \times 10^6$) and HEK293 cells ($0.3 \times 10^6$) were transfected with 50 pmol of GenCrispr NLS-Cas9-EGFP Nuclease, or ArciTect Cas9-eGFP Nuclease, or the GFP-SpCas9 protein of the current invention, in combination with 150 pmol each of four chemically synthesized sgRNAs targeting the Human EMX1, HEKSite4, VEGFA3, HPRT loci. The guide sequences are: 5'-GAGUCCGAGCAGAAGAAGAA-3' (EMX1) (SEQ ID NO:51), 5'-GGCACUGCGGCUGGAG-GUGG-3' (HEKSite4) (SEQ ID NO:52), 5'GGUGAGUGAGUGUGUGCGUG-3' (VEGFA3) (SEQ ID NO: 66), and 5'-GGUCACUUUUAACACACCCA-3'

(HPRT) (SEQ ID NO:53). Transfection was carried out using Nucleofection Solution V and an Amaxa instrument. Cells were maintained at 37° C. and 5% $CO_2$ for three days before harvested for gene editing analysis. Genomic DNA was prepared using QuickExtract DNA extraction solution. Each targeted genomic region was PCR amplified using a pair of primers consisting of target-specific sequences and next generation sequencing (NGS) adaptors. The primers are listed in the following table:

| | NGS primer sequences |
|---|---|
| Target | Primer sequence (5'-3') |
| EMX1 | Forward:<br>TCGTCGGCAGCGTCAGATGTGTATAAGAGACAG-<br>NNNNNNCC<br>CCAGTGGCTGCTCT (SEQ ID NO: 54)<br>Reverse:<br>GTCTCGTGGGCTCGGAGATGTGTATAAGAGACAG-<br>NNNNNNC<br>CAGGCCTCCCCAAAGC (SEQ ID NO: 55) |
| HEKSite4 | Forward:<br>TCGTCGGCAGCGTCAGATGTGTATAAGAGACAG-<br>NNNNNNGG<br>AACCCAGGTAGCCAGAGA (SEQ ID NO: 56)<br>Reverse:<br>GTCTCGTGGGCTCGGAGATGTGTATAAGAGACAG-<br>NNNNNNG<br>GGGTGGGGTCAGACGT (SEQ ID NO: 57) |
| VEGFA3 | Forward:<br>TCGTCGGCAGCGTCAGATGTGTATAAGAGACAG-<br>NNNNNNGC<br>CCATTCCCTCTTTAGCCA (SEQ ID NO: 58)<br>Reverse:<br>GTCTCGTGGGCTCGGAGATGTGTATAAGAGACAG-<br>NNNNNNG<br>GAGCAGGAAAGTGAGGTTAC (SEQ ID NO: 59) |
| HPRT | Forward:<br>TCGTCGGCAGCGTCAGATGTGTATAAGAGACAGNNNNNN-<br>NAA<br>TGGACACATGGGTAGTCAGG (SEQ ID NO: 60)<br>Reverse:<br>GTCTCGTGGGCTCGGAGATGTGTATAAGAGACAG-<br>NNNNNNG<br>GCTTATATCCAACACTTCGTGGG (SEQ ID NO: 61) |

Figure 2A:
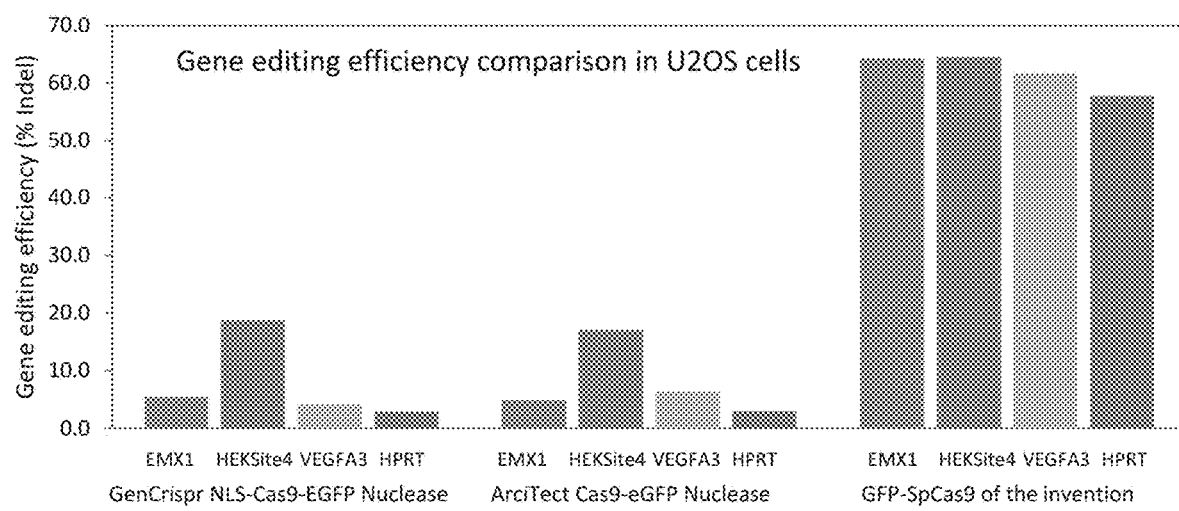
FIG. 2A and FIG. 2B show that the editing efficiencies of the Cas9 fusion proteins disclosed herein were several-fold higher than that of the commercial proteins in all targets.
Figure 2B:
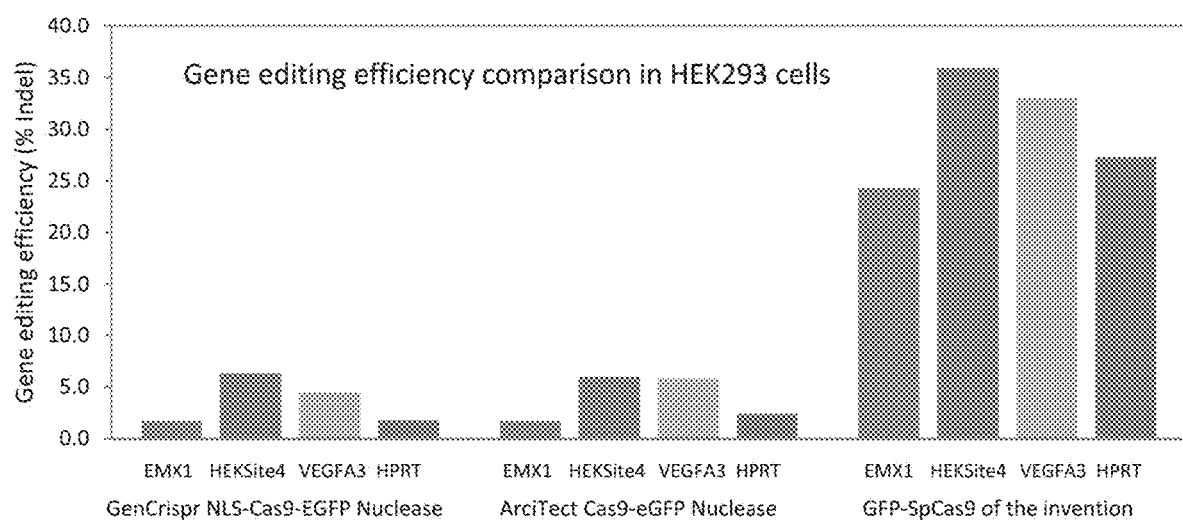

PCR amplicons were analyzed by NGS using the Illumina MiSeq to determine the editing efficiency of each Cas9 protein. The results in FIG. 2A and FIG. 2B show that the editing efficiencies by the GFP-SpCas9 protein of the current invention were several-fold higher than that of the commercial proteins in all targets.

What is claimed is:

1. A fusion protein comprising a *Streptococcus pyogenes* Cas9 protein; a marker protein; at least one first linker between the Cas9 protein and the marker protein, wherein the at least one first linker comprises SEQ ID NO:36; and a first heterologous domain that is a nuclear localization signal; wherein the fusion protein is a nuclease and cleaves both strands of a double-stranded sequence, is a nickase and cleaves one strand of a double-stranded sequence, or has no nuclease or nickase activity.

2. The fusion protein of claim 1, wherein the marker protein is at the C-terminus of the fusion protein.

3. The fusion protein of claim 1, further comprising an optional second linker, wherein the nuclear localization signal, the marker protein, the first linker, the optional second linker (if present), and the Cas9 protein are arranged in the following order (N-terminus to C-terminus):

marker protein-first linker-nuclear localization signal-Cas9 protein;

marker protein-nuclear localization signal-first linker-Cas9 protein;

nuclear localization signal-marker protein-first linker-Cas9 protein;

marker protein-first linker-nuclear localization signal-first linker-Cas9 protein; or nuclear localization signal-second linker-marker protein-first linker-Cas9 protein.

4. The fusion protein of claim 3, wherein the nuclear localization signal, the marker protein, the first linker, and the Cas9 protein are arranged in the following order (N-terminus to C-terminus):

marker protein-first linker-nuclear localization signal-Cas9 protein.

5. The fusion protein of claim 1, further comprising at least one additional heterologous domain other than the first heterologous domain that is a nuclear localization signal, wherein the at least one additional heterologous domain is a cell-penetrating domain, a chromatin modulating motif, an epigenetic modification domain, a transcriptional regulation domain, an RNA aptamer binding domain, or combination thereof.

6. The fusion protein of claim 1, wherein the marker protein has an amino acid sequence comprising SEQ ID NO:19 or 20.

7. The fusion protein of claim 1, wherein the marker protein has an amino acid sequence consisting of SEQ ID NO:19 or 20.

8. The fusion protein of claim 1, wherein the fusion protein has an amino acid sequence having at least 95% sequence identity with SEQ ID NO:49 or 50.

9. The fusion protein of claim 1, wherein the fusion protein has an amino acid sequence having at least 99% sequence identity with SEQ ID NO:49 or 50.

10. The fusion protein of claim 1, wherein the fusion protein has an amino acid sequence of SEQ ID NO:49 or 50.

* * * * *

SEQUENCE LISTING

```
<160> NUMBER OF SEQ ID NOS: 66

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Lys Lys Lys Arg Lys Val
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Lys Lys Lys Arg Arg Val
1               5

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Arg Pro Ala Ala Thr Lys Lys Ala Gly Gln Ala Lys Lys Lys Lys
1               5                   10                  15
```

-continued

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Gly Arg Lys Lys Arg Arg Gln Arg Arg Arg
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Lys Lys Arg Arg Gln Arg Arg Arg
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Ala Ala Lys Arg Val Lys Leu Asp
1               5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Gln Arg Arg Asn Glu Leu Lys Arg Ser Pro
1               5                   10

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Ser Arg Lys Arg Pro Arg Pro
1               5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 9

Pro Pro Lys Lys Ala Arg Glu Asp
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Gln Pro Lys Lys Lys Pro Leu
1               5

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Ala Leu Ile Lys Lys Lys Lys Lys Met Ala Pro
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Lys Gln Lys Lys Arg Lys
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Lys Leu Lys Lys Lys Ile Lys Lys Leu
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Glu Lys Lys Lys Phe Leu Lys Arg Arg
1               5                   10

<210> SEQ ID NO 15
<211> LENGTH: 20
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 15

Lys Arg Lys Gly Asp Glu Val Asp Gly Val Asp Glu Val Ala Lys Lys
1               5                   10                  15

Lys Ser Lys Lys
            20

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Lys Cys Leu Gln Ala Gly Met Asn Leu Glu Ala Arg Lys Thr Lys
1               5                   10                  15

Lys

<210> SEQ ID NO 17
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
            35

<210> SEQ ID NO 18
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
            35                  40

<210> SEQ ID NO 19
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19
```

```
Met Val Ser Lys Gly Glu Glu Leu Phe Thr Gly Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Lys Leu
                195                 200                 205

Ser Lys Asp Pro Asn Glu Lys Arg Asp His Met Val Leu Leu Glu Phe
            210                 215                 220

Val Thr Ala Ala Gly Ile Thr Leu Gly Met Asp Glu Leu Tyr Lys
225                 230                 235

<210> SEQ ID NO 20
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Val Ser Lys Gly Glu Ala Val Ile Lys Glu Phe Met Arg Phe Lys
1               5                   10                  15

Val His Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
            35                  40                  45

Val Thr Lys Gly Gly Pro Leu Pro Phe Ser Trp Asp Ile Leu Ser Pro
50                  55                  60

Gln Phe Met Tyr Gly Ser Arg Ala Phe Thr Lys His Pro Ala Asp Ile
65                  70                  75                  80

Pro Asp Tyr Tyr Lys Gln Ser Phe Pro Glu Gly Phe Lys Trp Glu Arg
                85                  90                  95

Val Met Asn Phe Glu Asp Gly Gly Ala Val Thr Val Thr Gln Asp Thr
                100                 105                 110

Ser Leu Glu Asp Gly Thr Leu Ile Tyr Lys Val Lys Leu Arg Gly Thr
```

```
                115                 120                 125
Asn Phe Pro Pro Asp Gly Pro Val Met Gln Lys Lys Thr Met Gly Trp
    130                 135                 140

Glu Ala Ser Thr Glu Arg Leu Tyr Pro Glu Asp Gly Val Leu Lys Gly
145                 150                 155                 160

Asp Ile Lys Met Ala Leu Arg Leu Lys Asp Gly Gly Arg Tyr Leu Ala
                165                 170                 175

Asp Phe Lys Thr Thr Tyr Lys Ala Lys Lys Pro Val Gln Met Pro Gly
            180                 185                 190

Ala Tyr Asn Val Asp Arg Lys Leu Asp Ile Thr Ser His Asn Glu Asp
        195                 200                 205

Tyr Thr Val Val Glu Gln Tyr Glu Arg Ser Glu Gly Arg His Ser Thr
    210                 215                 220

Gly Gly Met Asp Glu Leu Tyr Lys
225                 230

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Tyr Lys Asp Asp Asp Asp Lys
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 22

His His His His His His
1               5

<210> SEQ ID NO 23
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Arg Lys Lys Arg Arg Gln Arg Arg Arg Pro Pro Gln Pro Lys Lys
1               5                   10                  15

Lys Arg Lys Val
            20

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24
```

```
Pro Leu Ser Ser Ile Phe Ser Arg Ile Gly Asp Pro Lys Lys Lys
1               5                   10                  15

Arg Lys Val

<210> SEQ ID NO 25
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Ala Leu Phe Leu Gly Trp Leu Gly Ala Ala Gly Ser Thr Met Gly
1               5                   10                  15

Ala Pro Lys Lys Lys Arg Lys Val
            20

<210> SEQ ID NO 26
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 27
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Tyr Ala Arg Ala Ala Ala Arg Gln Ala Arg Ala
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 29

Thr His Arg Leu Pro Arg Arg Arg Arg Arg
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Gly Arg Arg Ala Arg Arg Arg Arg Arg
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Arg Gln Arg Arg Thr Ser Lys Leu Met Lys Arg
1               5                   10

<210> SEQ ID NO 32
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 33
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34
```

Arg Gln Ile Lys Ile Trp Phe Gln Asn Arg Arg Met Lys Trp Lys Lys
1               5                   10                  15

<210> SEQ ID NO 35
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Ala Lys Glu Ala
                20                  25                  30

Ala Ala Lys Glu Ala Ala Ala Lys Glu Ala Ala Ala Lys Ala
            35                  40                  45

<210> SEQ ID NO 36
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ser Gly Gly Ser Ser Gly Gly Ser Ser Gly Ser Glu Thr Pro Gly Thr
1               5                   10                  15

Ser Glu Ser Ala Thr Pro Glu Ser Ser Gly Gly Ser Ser Gly Gly Ser
                20                  25                  30

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Glu Gly Gly Gly Ser
1               5

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Gly Ser Gly
1

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Gly Ser Gly Gly Gly Ser Gly
1               5

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 "Gly Gly Gly
      Gly Ser" repeating units

<400> SEQUENCE: 40

Gly Gly Gly Gly Ser Gly Gly Gly Gly Ser Gly Gly Gly Gly Ser Gly
1               5                   10                  15

Gly Gly Gly Ser
            20

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(8)
<223> OTHER INFORMATION: This sequence may encompass 6-8 residues

<400> SEQUENCE: 41

Gly Gly Gly Gly Gly Gly Gly Gly
1               5

<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 "Glu Ala Ala
      Ala Lys" repeating units

<400> SEQUENCE: 42

Glu Ala Ala Ala Lys Glu Ala Ala Ala Lys Glu Ala Ala Ala Lys Glu
1               5                   10                  15

Ala Ala Ala Lys
            20

<210> SEQ ID NO 43
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(26)
<223> OTHER INFORMATION: This region may encompass 2-5 "Glu Ala Ala Ala
      Lys" repeating units

<400> SEQUENCE: 43

Ala Glu Ala Ala Ala Lys Glu Ala Ala Lys Glu Ala Ala Ala Lys
1               5                   10                  15

Glu Ala Ala Ala Lys Glu Ala Ala Ala Lys Ala
            20                  25

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Pro Ala Pro Ala Pro
1               5

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(16)
<223> OTHER INFORMATION: This sequence may encompass 6-8 "Ala Pro"
      repeating units

<400> SEQUENCE: 45

Ala Pro Ala Pro Ala Pro Ala Pro Ala Pro Ala Pro Ala Pro Ala Pro
1               5                   10                  15

<210> SEQ ID NO 46
<211> LENGTH: 60
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(39)
<223> OTHER INFORMATION: a, t, g or c

<400> SEQUENCE: 46
tcgtcggcag cgtcagatgt gtataagaga cagnnnnnna gtcttcccat caggctctca    60

<210> SEQ ID NO 47
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(40)
<223> OTHER INFORMATION: a, t, g or c

<400> SEQUENCE: 47
gtctcgtggg ctcggagatg tgtataagag acagnnnnnn agagtccagc ttgggcc    57

<210> SEQ ID NO 48
<211> LENGTH: 1692

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Val
225                 230                 235                 240

Asp Ala Glu Ala Ala Lys Glu Ala Ala Lys Glu Ala Ala
                245                 250                 255

Lys Glu Ala Ala Ala Lys Ala Leu Glu Ala Glu Ala Ala Lys Glu
                260                 265                 270

Ala Ala Ala Lys Glu Ala Ala Lys Glu Ala Ala Lys Ala Pro
        275                 280                 285

Ala Ala Lys Arg Val Lys Leu Asp Gly Gly Gly Ser Thr Gly Met
            290                 295                 300

Asp Lys Lys Tyr Ser Ile Gly Leu Asp Ile Gly Thr Asn Ser Val Gly
305                 310                 315                 320

Trp Ala Val Ile Thr Asp Glu Tyr Lys Val Pro Ser Lys Lys Phe Lys
                325                 330                 335

Val Leu Gly Asn Thr Asp Arg His Ser Ile Lys Lys Asn Leu Ile Gly
            340                 345                 350

Ala Leu Leu Phe Asp Ser Gly Glu Thr Ala Glu Ala Thr Arg Leu Lys
        355                 360                 365

Arg Thr Ala Arg Arg Arg Tyr Thr Arg Arg Lys Asn Arg Ile Cys Tyr
370                 375                 380
```

```
Leu Gln Glu Ile Phe Ser Asn Glu Met Ala Lys Val Asp Asp Ser Phe
385                 390                 395                 400

Phe His Arg Leu Glu Glu Ser Phe Leu Val Glu Glu Asp Lys Lys His
            405                 410                 415

Glu Arg His Pro Ile Phe Gly Asn Ile Val Asp Glu Val Ala Tyr His
                420                 425                 430

Glu Lys Tyr Pro Thr Ile Tyr His Leu Arg Lys Lys Leu Val Asp Ser
            435                 440                 445

Thr Asp Lys Ala Asp Leu Arg Leu Ile Tyr Leu Ala Leu Ala His Met
    450                 455                 460

Ile Lys Phe Arg Gly His Phe Leu Ile Glu Gly Asp Leu Asn Pro Asp
465                 470                 475                 480

Asn Ser Asp Val Asp Lys Leu Phe Ile Gln Leu Val Gln Thr Tyr Asn
                485                 490                 495

Gln Leu Phe Glu Glu Asn Pro Ile Asn Ala Ser Gly Val Asp Ala Lys
            500                 505                 510

Ala Ile Leu Ser Ala Arg Leu Ser Lys Ser Arg Arg Leu Glu Asn Leu
        515                 520                 525

Ile Ala Gln Leu Pro Gly Glu Lys Lys Asn Gly Leu Phe Gly Asn Leu
530                 535                 540

Ile Ala Leu Ser Leu Gly Leu Thr Pro Asn Phe Lys Ser Asn Phe Asp
545                 550                 555                 560

Leu Ala Glu Asp Ala Lys Leu Gln Leu Ser Lys Asp Thr Tyr Asp Asp
                565                 570                 575

Asp Leu Asp Asn Leu Leu Ala Gln Ile Gly Asp Gln Tyr Ala Asp Leu
            580                 585                 590

Phe Leu Ala Ala Lys Asn Leu Ser Asp Ala Ile Leu Leu Ser Asp Ile
        595                 600                 605

Leu Arg Val Asn Thr Glu Ile Thr Lys Ala Pro Leu Ser Ala Ser Met
    610                 615                 620

Ile Lys Arg Tyr Asp Glu His His Gln Asp Leu Thr Leu Leu Lys Ala
625                 630                 635                 640

Leu Val Arg Gln Gln Leu Pro Glu Lys Tyr Lys Glu Ile Phe Phe Asp
                645                 650                 655

Gln Ser Lys Asn Gly Tyr Ala Gly Tyr Ile Asp Gly Gly Ala Ser Gln
            660                 665                 670

Glu Glu Phe Tyr Lys Phe Ile Lys Pro Ile Leu Glu Lys Met Asp Gly
        675                 680                 685

Thr Glu Glu Leu Leu Val Lys Leu Asn Arg Glu Asp Leu Leu Arg Lys
    690                 695                 700

Gln Arg Thr Phe Asp Asn Gly Ser Ile Pro His Gln Ile His Leu Gly
705                 710                 715                 720

Glu Leu His Ala Ile Leu Arg Arg Gln Glu Asp Phe Tyr Pro Phe Leu
                725                 730                 735

Lys Asp Asn Arg Glu Lys Ile Glu Lys Ile Leu Thr Phe Arg Ile Pro
            740                 745                 750

Tyr Tyr Val Gly Pro Leu Ala Arg Gly Asn Ser Arg Phe Ala Trp Met
        755                 760                 765

Thr Arg Lys Ser Glu Glu Thr Ile Thr Pro Trp Asn Phe Glu Glu Val
    770                 775                 780

Val Asp Lys Gly Ala Ser Ala Gln Ser Phe Ile Glu Arg Met Thr Asn
785                 790                 795                 800
```

-continued

```
Phe Asp Lys Asn Leu Pro Asn Glu Lys Val Leu Pro Lys His Ser Leu
                805                 810                 815
Leu Tyr Glu Tyr Phe Thr Val Tyr Asn Glu Leu Thr Lys Val Lys Tyr
            820                 825                 830
Val Thr Glu Gly Met Arg Lys Pro Ala Phe Leu Ser Gly Glu Gln Lys
            835                 840                 845
Lys Ala Ile Val Asp Leu Leu Phe Lys Thr Asn Arg Lys Val Thr Val
850                 855                 860
Lys Gln Leu Lys Glu Asp Tyr Phe Lys Lys Ile Glu Cys Phe Asp Ser
865                 870                 875                 880
Val Glu Ile Ser Gly Val Glu Asp Arg Phe Asn Ala Ser Leu Gly Thr
                885                 890                 895
Tyr His Asp Leu Leu Lys Ile Ile Lys Asp Lys Asp Phe Leu Asp Asn
                900                 905                 910
Glu Glu Asn Glu Asp Ile Leu Glu Asp Ile Val Leu Thr Leu Thr Leu
            915                 920                 925
Phe Glu Asp Arg Glu Met Ile Glu Glu Arg Leu Lys Thr Tyr Ala His
            930                 935                 940
Leu Phe Asp Asp Lys Val Met Lys Gln Leu Lys Arg Arg Arg Tyr Thr
945                 950                 955                 960
Gly Trp Gly Arg Leu Ser Arg Lys Leu Ile Asn Gly Ile Arg Asp Lys
                965                 970                 975
Gln Ser Gly Lys Thr Ile Leu Asp Phe Leu Lys Ser Asp Gly Phe Ala
                980                 985                 990
Asn Arg Asn Phe Met Gln Leu Ile His Asp Asp Ser Leu Thr Phe Lys
            995                 1000                1005
Glu Asp Ile Gln Lys Ala Gln Val Ser Gly Gln Gly Asp Ser Leu
    1010                1015                1020
His Glu His Ile Ala Asn Leu Ala Gly Ser Pro Ala Ile Lys Lys
    1025                1030                1035
Gly Ile Leu Gln Thr Val Lys Val Val Asp Glu Leu Val Lys Val
    1040                1045                1050
Met Gly Arg His Lys Pro Glu Asn Ile Val Ile Glu Met Ala Arg
    1055                1060                1065
Glu Asn Gln Thr Thr Gln Lys Gly Gln Lys Asn Ser Arg Glu Arg
    1070                1075                1080
Met Lys Arg Ile Glu Glu Gly Ile Lys Glu Leu Gly Ser Gln Ile
    1085                1090                1095
Leu Lys Glu His Pro Val Glu Asn Thr Gln Leu Gln Asn Glu Lys
    1100                1105                1110
Leu Tyr Leu Tyr Tyr Leu Gln Asn Gly Arg Asp Met Tyr Val Asp
    1115                1120                1125
Gln Glu Leu Asp Ile Asn Arg Leu Ser Asp Tyr Asp Val Asp His
    1130                1135                1140
Ile Val Pro Gln Ser Phe Leu Lys Asp Asp Ser Ile Asp Asn Lys
    1145                1150                1155
Val Leu Thr Arg Ser Asp Lys Asn Arg Gly Lys Ser Asp Asn Val
    1160                1165                1170
Pro Ser Glu Glu Val Val Lys Lys Met Lys Asn Tyr Trp Arg Gln
    1175                1180                1185
Leu Leu Asn Ala Lys Leu Ile Thr Gln Arg Lys Phe Asp Asn Leu
    1190                1195                1200
Thr Lys Ala Glu Arg Gly Gly Leu Ser Glu Leu Asp Lys Ala Gly
```

-continued

```
          1205                1210                1215
Phe Ile Lys Arg Gln Leu Val Glu Thr Arg Gln Ile Thr Lys His
          1220                1225                1230
Val Ala Gln Ile Leu Asp Ser Arg Met Asn Thr Lys Tyr Asp Glu
          1235                1240                1245
Asn Asp Lys Leu Ile Arg Glu Val Lys Val Ile Thr Leu Lys Ser
          1250                1255                1260
Lys Leu Val Ser Asp Phe Arg Lys Asp Phe Gln Phe Tyr Lys Val
          1265                1270                1275
Arg Glu Ile Asn Asn Tyr His His Ala His Asp Ala Tyr Leu Asn
          1280                1285                1290
Ala Val Val Gly Thr Ala Leu Ile Lys Lys Tyr Pro Lys Leu Glu
          1295                1300                1305
Ser Glu Phe Val Tyr Gly Asp Tyr Lys Val Tyr Asp Val Arg Lys
          1310                1315                1320
Met Ile Ala Lys Ser Glu Gln Glu Ile Gly Lys Ala Thr Ala Lys
          1325                1330                1335
Tyr Phe Phe Tyr Ser Asn Ile Met Asn Phe Phe Lys Thr Glu Ile
          1340                1345                1350
Thr Leu Ala Asn Gly Glu Ile Arg Lys Arg Pro Leu Ile Glu Thr
          1355                1360                1365
Asn Gly Glu Thr Gly Glu Ile Val Trp Asp Lys Gly Arg Asp Phe
          1370                1375                1380
Ala Thr Val Arg Lys Val Leu Ser Met Pro Gln Val Asn Ile Val
          1385                1390                1395
Lys Lys Thr Glu Val Gln Thr Gly Gly Phe Ser Lys Glu Ser Ile
          1400                1405                1410
Leu Pro Lys Arg Asn Ser Asp Lys Leu Ile Ala Arg Lys Lys Asp
          1415                1420                1425
Trp Asp Pro Lys Lys Tyr Gly Gly Phe Asp Ser Pro Thr Val Ala
          1430                1435                1440
Tyr Ser Val Leu Val Val Ala Lys Val Glu Lys Gly Lys Ser Lys
          1445                1450                1455
Lys Leu Lys Ser Val Lys Glu Leu Leu Gly Ile Thr Ile Met Glu
          1460                1465                1470
Arg Ser Ser Phe Glu Lys Asn Pro Ile Asp Phe Leu Glu Ala Lys
          1475                1480                1485
Gly Tyr Lys Glu Val Lys Lys Asp Leu Ile Ile Lys Leu Pro Lys
          1490                1495                1500
Tyr Ser Leu Phe Glu Leu Glu Asn Gly Arg Lys Arg Met Leu Ala
          1505                1510                1515
Ser Ala Gly Glu Leu Gln Lys Gly Asn Glu Leu Ala Leu Pro Ser
          1520                1525                1530
Lys Tyr Val Asn Phe Leu Tyr Leu Ala Ser His Tyr Glu Lys Leu
          1535                1540                1545
Lys Gly Ser Pro Glu Asp Asn Glu Gln Lys Gln Leu Phe Val Glu
          1550                1555                1560
Gln His Lys His Tyr Leu Asp Glu Ile Ile Glu Gln Ile Ser Glu
          1565                1570                1575
Phe Ser Lys Arg Val Ile Leu Ala Asp Ala Asn Leu Asp Lys Val
          1580                1585                1590
Leu Ser Ala Tyr Asn Lys His Arg Asp Lys Pro Ile Arg Glu Gln
          1595                1600                1605
```

```
Ala Glu Asn Ile Ile His Leu Phe Thr Leu Thr Asn Leu Gly Ala
    1610                1615                1620

Pro Ala Ala Phe Lys Tyr Phe Asp Thr Thr Ile Asp Arg Lys Arg
1625                1630                1635

Tyr Thr Ser Thr Lys Glu Val Leu Asp Ala Thr Leu Ile His Gln
    1640                1645                1650

Ser Ile Thr Gly Leu Tyr Glu Thr Arg Ile Asp Leu Ser Gln Leu
    1655                1660                1665

Gly Gly Asp Glu Phe Pro Lys Lys Lys Arg Lys Val Gly Gly Gly
    1670                1675                1680

Gly Ser Pro Lys Lys Lys Arg Lys Val
    1685                1690

<210> SEQ ID NO 49
<211> LENGTH: 1671
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Met Val Ser Lys Gly Glu Ala Val Ile Lys Glu Phe Met Arg Phe Lys
1               5                   10                  15

Val His Met Glu Gly Ser Met Asn Gly His Glu Phe Glu Ile Glu Gly
            20                  25                  30

Glu Gly Glu Gly Arg Pro Tyr Glu Gly Thr Gln Thr Ala Lys Leu Lys
        35                  40                  45

Val Thr Lys Gly Gly Pro Leu Pro Phe Ser Trp Asp Ile Leu Ser Pro
    50                  55                  60

Gln Phe Met Tyr Gly Ser Arg Ala Phe Thr Lys His Pro Ala Asp Ile
65                  70                  75                  80

Pro Asp Tyr Tyr Lys Gln Ser Phe Pro Glu Gly Phe Lys Trp Glu Arg
                85                  90                  95

Val Met Asn Phe Glu Asp Gly Gly Ala Val Thr Val Thr Gln Asp Thr
            100                 105                 110

Ser Leu Glu Asp Gly Thr Leu Ile Tyr Lys Val Lys Leu Arg Gly Thr
        115                 120                 125

Asn Phe Pro Pro Asp Gly Pro Val Met Gln Lys Lys Thr Met Gly Trp
    130                 135                 140

Glu Ala Ser Thr Glu Arg Leu Tyr Pro Glu Asp Gly Val Leu Lys Gly
145                 150                 155                 160

Asp Ile Lys Met Ala Leu Arg Leu Lys Asp Gly Gly Arg Tyr Leu Ala
                165                 170                 175

Asp Phe Lys Thr Thr Tyr Lys Ala Lys Lys Pro Val Gln Met Pro Gly
            180                 185                 190

Ala Tyr Asn Val Asp Arg Lys Leu Asp Ile Thr Ser His Asn Glu Asp
        195                 200                 205

Tyr Thr Val Val Glu Gln Tyr Glu Arg Ser Glu Gly Arg His Ser Thr
    210                 215                 220

Gly Gly Met Asp Glu Leu Tyr Lys Val Asp Gly Gly Ser Gly Ser Gly
225                 230                 235                 240

Gly Ser Ser Gly Ser Glu Thr Pro Gly Thr Ser Glu Ser Ala Thr Pro
                245                 250                 255

Glu Ser Ser Gly Gly Ser Ser Gly Gly Ser Pro Ala Ala Lys Arg Val
```

```
                260              265                270
Lys Leu Asp Gly Gly Gly Ser Thr Gly Met Asp Lys Lys Tyr Ser
            275                280               285
Ile Gly Leu Asp Ile Gly Thr Asn Ser Val Gly Trp Ala Val Ile Thr
            290                295               300
Asp Glu Tyr Lys Val Pro Ser Lys Lys Phe Lys Val Leu Gly Asn Thr
305                 310               315                320
Asp Arg His Ser Ile Lys Lys Asn Leu Ile Gly Ala Leu Leu Phe Asp
                325                330               335
Ser Gly Glu Thr Ala Glu Ala Thr Arg Leu Lys Arg Thr Ala Arg Arg
                340                345               350
Arg Tyr Thr Arg Arg Lys Asn Arg Ile Cys Tyr Leu Gln Glu Ile Phe
            355                360               365
Ser Asn Glu Met Ala Lys Val Asp Asp Ser Phe Phe His Arg Leu Glu
            370                375               380
Glu Ser Phe Leu Val Glu Glu Asp Lys Lys His Glu Arg His Pro Ile
385                 390               395                400
Phe Gly Asn Ile Val Asp Glu Val Ala Tyr His Glu Lys Tyr Pro Thr
                405                410               415
Ile Tyr His Leu Arg Lys Lys Leu Val Asp Ser Thr Asp Lys Ala Asp
                420                425               430
Leu Arg Leu Ile Tyr Leu Ala Leu Ala His Met Ile Lys Phe Arg Gly
            435                440               445
His Phe Leu Ile Glu Gly Asp Leu Asn Pro Asp Asn Ser Asp Val Asp
            450                455               460
Lys Leu Phe Ile Gln Leu Val Gln Thr Tyr Asn Gln Leu Phe Glu Glu
465                 470               475                480
Asn Pro Ile Asn Ala Ser Gly Val Asp Ala Lys Ala Ile Leu Ser Ala
                485                490               495
Arg Leu Ser Lys Ser Arg Arg Leu Glu Asn Leu Ile Ala Gln Leu Pro
            500                505               510
Gly Glu Lys Lys Asn Gly Leu Phe Gly Asn Leu Ile Ala Leu Ser Leu
            515                520               525
Gly Leu Thr Pro Asn Phe Lys Ser Asn Phe Asp Leu Ala Glu Asp Ala
            530                535               540
Lys Leu Gln Leu Ser Lys Asp Thr Tyr Asp Asp Asp Leu Asp Asn Leu
545                 550               555                560
Leu Ala Gln Ile Gly Asp Gln Tyr Ala Asp Leu Phe Leu Ala Ala Lys
                565                570               575
Asn Leu Ser Asp Ala Ile Leu Leu Ser Asp Ile Leu Arg Val Asn Thr
                580                585               590
Glu Ile Thr Lys Ala Pro Leu Ser Ala Ser Met Ile Lys Arg Tyr Asp
            595                600               605
Glu His His Gln Asp Leu Thr Leu Leu Lys Ala Leu Val Arg Gln Gln
            610                615               620
Leu Pro Glu Lys Tyr Lys Glu Ile Phe Phe Asp Gln Ser Lys Asn Gly
625                 630               635                640
Tyr Ala Gly Tyr Ile Asp Gly Gly Ala Ser Gln Glu Glu Phe Tyr Lys
                645                650               655
Phe Ile Lys Pro Ile Leu Glu Lys Met Asp Gly Thr Glu Glu Leu Leu
                660                665               670
Val Lys Leu Asn Arg Glu Asp Leu Leu Arg Lys Gln Arg Thr Phe Asp
            675                680               685
```

-continued

```
Asn Gly Ser Ile Pro His Gln Ile His Leu Gly Glu Leu His Ala Ile
    690             695                 700
Leu Arg Arg Gln Glu Asp Phe Tyr Pro Phe Leu Lys Asp Asn Arg Glu
705                 710                 715                 720
Lys Ile Glu Lys Ile Leu Thr Phe Arg Ile Pro Tyr Tyr Val Gly Pro
            725                 730                 735
Leu Ala Arg Gly Asn Ser Arg Phe Ala Trp Met Thr Arg Lys Ser Glu
            740                 745                 750
Glu Thr Ile Thr Pro Trp Asn Phe Glu Glu Val Val Asp Lys Gly Ala
        755                 760                 765
Ser Ala Gln Ser Phe Ile Glu Arg Met Thr Asn Phe Asp Lys Asn Leu
770                 775                 780
Pro Asn Glu Lys Val Leu Pro Lys His Ser Leu Leu Tyr Glu Tyr Phe
785                 790                 795                 800
Thr Val Tyr Asn Glu Leu Thr Lys Val Lys Tyr Val Thr Glu Gly Met
            805                 810                 815
Arg Lys Pro Ala Phe Leu Ser Gly Glu Gln Lys Lys Ala Ile Val Asp
            820                 825                 830
Leu Leu Phe Lys Thr Asn Arg Lys Val Thr Val Lys Gln Leu Lys Glu
        835                 840                 845
Asp Tyr Phe Lys Lys Ile Glu Cys Phe Asp Ser Val Glu Ile Ser Gly
850                 855                 860
Val Glu Asp Arg Phe Asn Ala Ser Leu Gly Thr Tyr His Asp Leu Leu
865                 870                 875                 880
Lys Ile Ile Lys Asp Lys Asp Phe Leu Asp Asn Glu Glu Asn Glu Asp
            885                 890                 895
Ile Leu Glu Asp Ile Val Leu Thr Leu Thr Leu Phe Glu Asp Arg Glu
            900                 905                 910
Met Ile Glu Glu Arg Leu Lys Thr Tyr Ala His Leu Phe Asp Asp Lys
        915                 920                 925
Val Met Lys Gln Leu Lys Arg Arg Arg Tyr Thr Gly Trp Gly Arg Leu
930                 935                 940
Ser Arg Lys Leu Ile Asn Gly Ile Arg Asp Lys Gln Ser Gly Lys Thr
945                 950                 955                 960
Ile Leu Asp Phe Leu Lys Ser Asp Gly Phe Ala Asn Arg Asn Phe Met
            965                 970                 975
Gln Leu Ile His Asp Asp Ser Leu Thr Phe Lys Glu Asp Ile Gln Lys
            980                 985                 990
Ala Gln Val Ser Gly Gln Gly Asp Ser Leu His Glu His Ile Ala Asn
        995                 1000                1005
Leu Ala Gly Ser Pro Ala Ile Lys Lys Gly Ile Leu Gln Thr Val
    1010                1015                1020
Lys Val Val Asp Glu Leu Val Lys Val Met Gly Arg His Lys Pro
    1025                1030                1035
Glu Asn Ile Val Ile Glu Met Ala Arg Glu Asn Gln Thr Thr Gln
    1040                1045                1050
Lys Gly Gln Lys Asn Ser Arg Glu Arg Met Lys Arg Ile Glu Glu
    1055                1060                1065
Gly Ile Lys Glu Leu Gly Ser Gln Ile Leu Lys Glu His Pro Val
    1070                1075                1080
Glu Asn Thr Gln Leu Gln Asn Glu Lys Leu Tyr Leu Tyr Tyr Leu
    1085                1090                1095
```

```
Gln Asn Gly Arg Asp Met Tyr Val Asp Gln Glu Leu Asp Ile Asn
1100                1105                1110

Arg Leu Ser Asp Tyr Asp Val Asp His Ile Val Pro Gln Ser Phe
    1115                1120                1125

Leu Lys Asp Asp Ser Ile Asp Asn Lys Val Leu Thr Arg Ser Asp
    1130                1135                1140

Lys Asn Arg Gly Lys Ser Asp Asn Val Pro Ser Glu Glu Val Val
    1145                1150                1155

Lys Lys Met Lys Asn Tyr Trp Arg Gln Leu Leu Asn Ala Lys Leu
    1160                1165                1170

Ile Thr Gln Arg Lys Phe Asp Asn Leu Thr Lys Ala Glu Arg Gly
    1175                1180                1185

Gly Leu Ser Glu Leu Asp Lys Ala Gly Phe Ile Lys Arg Gln Leu
    1190                1195                1200

Val Glu Thr Arg Gln Ile Thr Lys His Val Ala Gln Ile Leu Asp
    1205                1210                1215

Ser Arg Met Asn Thr Lys Tyr Asp Glu Asn Asp Lys Leu Ile Arg
    1220                1225                1230

Glu Val Lys Val Ile Thr Leu Lys Ser Lys Leu Val Ser Asp Phe
    1235                1240                1245

Arg Lys Asp Phe Gln Phe Tyr Lys Val Arg Glu Ile Asn Asn Tyr
    1250                1255                1260

His His Ala His Asp Ala Tyr Leu Asn Ala Val Val Gly Thr Ala
    1265                1270                1275

Leu Ile Lys Lys Tyr Pro Lys Leu Glu Ser Glu Phe Val Tyr Gly
    1280                1285                1290

Asp Tyr Lys Val Tyr Asp Val Arg Lys Met Ile Ala Lys Ser Glu
    1295                1300                1305

Gln Glu Ile Gly Lys Ala Thr Ala Lys Tyr Phe Phe Tyr Ser Asn
    1310                1315                1320

Ile Met Asn Phe Phe Lys Thr Glu Ile Thr Leu Ala Asn Gly Glu
    1325                1330                1335

Ile Arg Lys Arg Pro Leu Ile Glu Thr Asn Gly Glu Thr Gly Glu
    1340                1345                1350

Ile Val Trp Asp Lys Gly Arg Asp Phe Ala Thr Val Arg Lys Val
    1355                1360                1365

Leu Ser Met Pro Gln Val Asn Ile Val Lys Lys Thr Glu Val Gln
    1370                1375                1380

Thr Gly Gly Phe Ser Lys Glu Ser Ile Leu Pro Lys Arg Asn Ser
    1385                1390                1395

Asp Lys Leu Ile Ala Arg Lys Lys Asp Trp Asp Pro Lys Lys Tyr
    1400                1405                1410

Gly Gly Phe Asp Ser Pro Thr Val Ala Tyr Ser Val Leu Val Val
    1415                1420                1425

Ala Lys Val Glu Lys Gly Lys Ser Lys Lys Leu Lys Ser Val Lys
    1430                1435                1440

Glu Leu Leu Gly Ile Thr Ile Met Glu Arg Ser Ser Phe Glu Lys
    1445                1450                1455

Asn Pro Ile Asp Phe Leu Glu Ala Lys Gly Tyr Lys Glu Val Lys
    1460                1465                1470

Lys Asp Leu Ile Ile Lys Leu Pro Lys Tyr Ser Leu Phe Glu Leu
    1475                1480                1485

Glu Asn Gly Arg Lys Arg Met Leu Ala Ser Ala Gly Glu Leu Gln
```

```
                    1490                1495                1500

Lys Gly Asn Glu Leu Ala Leu Pro Ser Lys Tyr Val Asn Phe Leu
    1505                1510                1515

Tyr Leu Ala Ser His Tyr Glu Lys Leu Lys Gly Ser Pro Glu Asp
    1520                1525                1530

Asn Glu Gln Lys Gln Leu Phe Val Glu Gln His Lys His Tyr Leu
    1535                1540                1545

Asp Glu Ile Ile Glu Gln Ile Ser Glu Phe Ser Lys Arg Val Ile
    1550                1555                1560

Leu Ala Asp Ala Asn Leu Asp Lys Val Leu Ser Ala Tyr Asn Lys
    1565                1570                1575

His Arg Asp Lys Pro Ile Arg Glu Gln Ala Glu Asn Ile Ile His
    1580                1585                1590

Leu Phe Thr Leu Thr Asn Leu Gly Ala Pro Ala Ala Phe Lys Tyr
    1595                1600                1605

Phe Asp Thr Thr Ile Asp Arg Lys Arg Tyr Thr Ser Thr Lys Glu
    1610                1615                1620

Val Leu Asp Ala Thr Leu Ile His Gln Ser Ile Thr Gly Leu Tyr
    1625                1630                1635

Glu Thr Arg Ile Asp Leu Ser Gln Leu Gly Gly Asp Glu Phe Pro
    1640                1645                1650

Lys Lys Lys Arg Lys Val Gly Gly Gly Ser Pro Lys Lys Lys
    1655                1660                1665

Arg Lys Val
    1670

<210> SEQ ID NO 50
<211> LENGTH: 1678
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160
```

```
Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Lys Leu
            195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Val
225                 230                 235                 240

Asp Ser Gly Gly Ser Gly Gly Ser Gly Ser Glu Thr Pro Gly
                245                 250                 255

Thr Ser Glu Ser Ala Thr Pro Glu Ser Ser Gly Gly Ser Ser Gly Gly
        260                 265                 270

Ser Pro Ala Ala Lys Arg Val Lys Leu Asp Gly Gly Gly Ser Thr
    275                 280                 285

Gly Met Asp Lys Lys Tyr Ser Ile Gly Leu Asp Ile Gly Thr Asn Ser
    290                 295                 300

Val Gly Trp Ala Val Ile Thr Asp Glu Tyr Lys Val Pro Ser Lys Lys
305                 310                 315                 320

Phe Lys Val Leu Gly Asn Thr Asp Arg His Ser Ile Lys Lys Asn Leu
                325                 330                 335

Ile Gly Ala Leu Leu Phe Asp Ser Gly Glu Thr Ala Glu Ala Thr Arg
                340                 345                 350

Leu Lys Arg Thr Ala Arg Arg Arg Tyr Thr Arg Arg Lys Asn Arg Ile
        355                 360                 365

Cys Tyr Leu Gln Glu Ile Phe Ser Asn Glu Met Ala Lys Val Asp Asp
    370                 375                 380

Ser Phe Phe His Arg Leu Glu Glu Ser Phe Leu Val Glu Glu Asp Lys
385                 390                 395                 400

Lys His Glu Arg His Pro Ile Phe Gly Asn Ile Val Asp Glu Val Ala
                405                 410                 415

Tyr His Glu Lys Tyr Pro Thr Ile Tyr His Leu Arg Lys Lys Leu Val
            420                 425                 430

Asp Ser Thr Asp Lys Ala Asp Leu Arg Leu Ile Tyr Leu Ala Leu Ala
        435                 440                 445

His Met Ile Lys Phe Arg Gly His Phe Leu Ile Glu Gly Asp Leu Asn
    450                 455                 460

Pro Asp Asn Ser Asp Val Asp Lys Leu Phe Ile Gln Leu Val Gln Thr
465                 470                 475                 480

Tyr Asn Gln Leu Phe Glu Glu Asn Pro Ile Asn Ala Ser Gly Val Asp
                485                 490                 495

Ala Lys Ala Ile Leu Ser Ala Arg Leu Ser Lys Ser Arg Arg Leu Glu
            500                 505                 510

Asn Leu Ile Ala Gln Leu Pro Gly Glu Lys Lys Asn Gly Leu Phe Gly
        515                 520                 525

Asn Leu Ile Ala Leu Ser Leu Gly Leu Thr Pro Asn Phe Lys Ser Asn
    530                 535                 540

Phe Asp Leu Ala Glu Asp Ala Lys Leu Gln Leu Ser Lys Asp Thr Tyr
545                 550                 555                 560

Asp Asp Asp Leu Asp Asn Leu Leu Ala Gln Ile Gly Asp Gln Tyr Ala
                565                 570                 575

Asp Leu Phe Leu Ala Ala Lys Asn Leu Ser Asp Ala Ile Leu Leu Ser
```

-continued

```
                580             585             590
Asp Ile Leu Arg Val Asn Thr Glu Ile Thr Lys Ala Pro Leu Ser Ala
            595                 600                 605

Ser Met Ile Lys Arg Tyr Asp Glu His His Gln Asp Leu Thr Leu Leu
        610                 615                 620

Lys Ala Leu Val Arg Gln Gln Leu Pro Glu Lys Tyr Lys Glu Ile Phe
625                 630                 635                 640

Phe Asp Gln Ser Lys Asn Gly Tyr Ala Gly Tyr Ile Asp Gly Gly Ala
                645                 650                 655

Ser Gln Glu Glu Phe Tyr Lys Phe Ile Lys Pro Ile Leu Glu Lys Met
            660                 665                 670

Asp Gly Thr Glu Glu Leu Leu Val Lys Leu Asn Arg Glu Asp Leu Leu
        675                 680                 685

Arg Lys Gln Arg Thr Phe Asp Asn Gly Ser Ile Pro His Gln Ile His
690                 695                 700

Leu Gly Glu Leu His Ala Ile Leu Arg Arg Gln Glu Asp Phe Tyr Pro
705                 710                 715                 720

Phe Leu Lys Asp Asn Arg Glu Lys Ile Glu Lys Ile Leu Thr Phe Arg
                725                 730                 735

Ile Pro Tyr Tyr Val Gly Pro Leu Ala Arg Gly Asn Ser Arg Phe Ala
            740                 745                 750

Trp Met Thr Arg Lys Ser Glu Glu Thr Ile Thr Pro Trp Asn Phe Glu
        755                 760                 765

Glu Val Val Asp Lys Gly Ala Ser Ala Gln Ser Phe Ile Glu Arg Met
770                 775                 780

Thr Asn Phe Asp Lys Asn Leu Pro Asn Glu Lys Val Leu Pro Lys His
785                 790                 795                 800

Ser Leu Leu Tyr Glu Tyr Phe Thr Val Tyr Asn Glu Leu Thr Lys Val
                805                 810                 815

Lys Tyr Val Thr Glu Gly Met Arg Lys Pro Ala Phe Leu Ser Gly Glu
            820                 825                 830

Gln Lys Lys Ala Ile Val Asp Leu Leu Phe Lys Thr Asn Arg Lys Val
        835                 840                 845

Thr Val Lys Gln Leu Lys Glu Asp Tyr Phe Lys Lys Ile Glu Cys Phe
850                 855                 860

Asp Ser Val Glu Ile Ser Gly Val Glu Asp Arg Phe Asn Ala Ser Leu
865                 870                 875                 880

Gly Thr Tyr His Asp Leu Leu Lys Ile Ile Lys Asp Lys Asp Phe Leu
                885                 890                 895

Asp Asn Glu Glu Asn Glu Asp Ile Leu Glu Asp Ile Val Leu Thr Leu
            900                 905                 910

Thr Leu Phe Glu Asp Arg Glu Met Ile Glu Glu Arg Leu Lys Thr Tyr
        915                 920                 925

Ala His Leu Phe Asp Asp Lys Val Met Lys Gln Leu Lys Arg Arg Arg
930                 935                 940

Tyr Thr Gly Trp Gly Arg Leu Ser Arg Lys Leu Ile Asn Gly Ile Arg
945                 950                 955                 960

Asp Lys Gln Ser Gly Lys Thr Ile Leu Asp Phe Leu Lys Ser Asp Gly
                965                 970                 975

Phe Ala Asn Arg Asn Phe Met Gln Leu Ile His Asp Asp Ser Leu Thr
            980                 985                 990

Phe Lys Glu Asp Ile Gln Lys Ala  Gln Val Ser Gly Gln  Gly Asp Ser
        995                 1000                1005
```

-continued

```
Leu His Glu His Ile Ala Asn Leu Ala Gly Ser Pro Ala Ile Lys
    1010            1015                1020

Lys Gly Ile Leu Gln Thr Val Lys Val Val Asp Glu Leu Val Lys
    1025            1030                1035

Val Met Gly Arg His Lys Pro Glu Asn Ile Val Ile Glu Met Ala
    1040            1045                1050

Arg Glu Asn Gln Thr Thr Gln Lys Gly Gln Lys Asn Ser Arg Glu
    1055            1060                1065

Arg Met Lys Arg Ile Glu Glu Gly Ile Lys Glu Leu Gly Ser Gln
    1070            1075                1080

Ile Leu Lys Glu His Pro Val Glu Asn Thr Gln Leu Gln Asn Glu
    1085            1090                1095

Lys Leu Tyr Leu Tyr Tyr Leu Gln Asn Gly Arg Asp Met Tyr Val
    1100            1105                1110

Asp Gln Glu Leu Asp Ile Asn Arg Leu Ser Asp Tyr Asp Val Asp
    1115            1120                1125

His Ile Val Pro Gln Ser Phe Leu Ala Asp Asp Ser Ile Asp Asn
    1130            1135                1140

Lys Val Leu Thr Arg Ser Asp Lys Asn Arg Gly Lys Ser Asp Asn
    1145            1150                1155

Val Pro Ser Glu Glu Val Val Lys Lys Met Lys Asn Tyr Trp Arg
    1160            1165                1170

Gln Leu Leu Asn Ala Lys Leu Ile Thr Gln Arg Lys Phe Asp Asn
    1175            1180                1185

Leu Thr Lys Ala Glu Arg Gly Gly Leu Ser Glu Leu Asp Lys Ala
    1190            1195                1200

Gly Phe Ile Lys Arg Gln Leu Val Glu Thr Arg Gln Ile Thr Lys
    1205            1210                1215

His Val Ala Gln Ile Leu Asp Ser Arg Met Asn Thr Lys Tyr Asp
    1220            1225                1230

Glu Asn Asp Lys Leu Ile Arg Glu Val Lys Val Ile Thr Leu Lys
    1235            1240                1245

Ser Lys Leu Val Ser Asp Phe Arg Lys Asp Phe Gln Phe Tyr Lys
    1250            1255                1260

Val Arg Glu Ile Asn Asn Tyr His His Ala His Asp Ala Tyr Leu
    1265            1270                1275

Asn Ala Val Val Gly Thr Ala Leu Ile Lys Lys Tyr Pro Ala Leu
    1280            1285                1290

Glu Ser Glu Phe Val Tyr Gly Asp Tyr Lys Val Tyr Asp Val Arg
    1295            1300                1305

Lys Met Ile Ala Lys Ser Glu Gln Glu Ile Gly Lys Ala Thr Ala
    1310            1315                1320

Lys Tyr Phe Phe Tyr Ser Asn Ile Met Asn Phe Phe Lys Thr Glu
    1325            1330                1335

Ile Thr Leu Ala Asn Gly Glu Ile Arg Lys Ala Pro Leu Ile Glu
    1340            1345                1350

Thr Asn Gly Glu Thr Gly Glu Ile Val Trp Asp Lys Gly Arg Asp
    1355            1360                1365

Phe Ala Thr Val Arg Lys Val Leu Ser Met Pro Gln Val Asn Ile
    1370            1375                1380

Val Lys Lys Thr Glu Val Gln Thr Gly Gly Phe Ser Lys Glu Ser
    1385            1390                1395
```

```
Ile Leu Pro Lys Arg Asn Ser Asp Lys Leu Ile Ala Arg Lys Lys
1400                1405                1410

Asp Trp Asp Pro Lys Lys Tyr Gly Gly Phe Asp Ser Pro Thr Val
1415                1420                1425

Ala Tyr Ser Val Leu Val Val Ala Lys Val Glu Lys Gly Lys Ser
1430                1435                1440

Lys Lys Leu Lys Ser Val Lys Glu Leu Leu Gly Ile Thr Ile Met
1445                1450                1455

Glu Arg Ser Ser Phe Glu Lys Asn Pro Ile Asp Phe Leu Glu Ala
1460                1465                1470

Lys Gly Tyr Lys Glu Val Lys Lys Asp Leu Ile Ile Lys Leu Pro
1475                1480                1485

Lys Tyr Ser Leu Phe Glu Leu Glu Asn Gly Arg Lys Arg Met Leu
1490                1495                1500

Ala Ser Ala Gly Glu Leu Gln Lys Gly Asn Glu Leu Ala Leu Pro
1505                1510                1515

Ser Lys Tyr Val Asn Phe Leu Tyr Leu Ala Ser His Tyr Glu Lys
1520                1525                1530

Leu Lys Gly Ser Pro Glu Asp Asn Glu Gln Lys Gln Leu Phe Val
1535                1540                1545

Glu Gln His Lys His Tyr Leu Asp Glu Ile Ile Glu Gln Ile Ser
1550                1555                1560

Glu Phe Ser Lys Arg Val Ile Leu Ala Asp Ala Asn Leu Asp Lys
1565                1570                1575

Val Leu Ser Ala Tyr Asn Lys His Arg Asp Lys Pro Ile Arg Glu
1580                1585                1590

Gln Ala Glu Asn Ile Ile His Leu Phe Thr Leu Thr Asn Leu Gly
1595                1600                1605

Ala Pro Ala Ala Phe Lys Tyr Phe Asp Thr Thr Ile Asp Arg Lys
1610                1615                1620

Arg Tyr Thr Ser Thr Lys Glu Val Leu Asp Ala Thr Leu Ile His
1625                1630                1635

Gln Ser Ile Thr Gly Leu Tyr Glu Thr Arg Ile Asp Leu Ser Gln
1640                1645                1650

Leu Gly Gly Asp Glu Phe Pro Lys Lys Arg Lys Val Gly Gly
1655                1660                1665

Gly Gly Ser Pro Lys Lys Lys Arg Lys Val
1670                1675

<210> SEQ ID NO 51
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
gaguccgagc agaagaagaa                                                    20

<210> SEQ ID NO 52
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 52
ggcacugcgg cuggaggugg                                           20

<210> SEQ ID NO 53
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
ggucacuuuu aacacaccca                                           20

<210> SEQ ID NO 54
<211> LENGTH: 55
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(39)
<223> OTHER INFORMATION: a, t, g or c

<400> SEQUENCE: 54
tcgtcggcag cgtcagatgt gtataagaga cagnnnnnnc cccagtggct gctct    55

<210> SEQ ID NO 55
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(40)
<223> OTHER INFORMATION: a, t, g or c

<400> SEQUENCE: 55
gtctcgtggg ctcggagatg tgtataagag acagnnnnnn ccaggcctcc ccaaagc  57

<210> SEQ ID NO 56
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(39)
<223> OTHER INFORMATION: a, t, g or c

<400> SEQUENCE: 56
tcgtcggcag cgtcagatgt gtataagaga cagnnnnnng aacccaggt agccagaga 59

<210> SEQ ID NO 57
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(40)

<223> OTHER INFORMATION: a, t, g or c

<400> SEQUENCE: 57
gtctcgtggg ctcggagatg tgtataagag acagnnnnnn ggggtggggt cagacgt      57

<210> SEQ ID NO 58
<211> LENGTH: 59
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(39)
<223> OTHER INFORMATION: a, t, g or c

<400> SEQUENCE: 58
tcgtcggcag cgtcagatgt gtataagaga cagnnnnnng cccattccct ctttagcca    59

<210> SEQ ID NO 59
<211> LENGTH: 61
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(40)
<223> OTHER INFORMATION: a, t, g or c

<400> SEQUENCE: 59
gtctcgtggg ctcggagatg tgtataagag acagnnnnnn ggagcaggaa agtgaggtta   60
c                                                                   61

<210> SEQ ID NO 60
<211> LENGTH: 61
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (34)..(39)
<223> OTHER INFORMATION: a, t, g or c

<400> SEQUENCE: 60
tcgtcggcag cgtcagatgt gtataagaga cagnnnnnna atggacacat gggtagtcag   60
g                                                                   61

<210> SEQ ID NO 61
<211> LENGTH: 64
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (35)..(40)
<223> OTHER INFORMATION: a, t, g or c

<400> SEQUENCE: 61
gtctcgtggg ctcggagatg tgtataagag acagnnnnnn ggcttatatc caacacttcg   60
tggg                                                                64

<210> SEQ ID NO 62
<211> LENGTH: 5076
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 62

```
atggttagca aaggtgaaga actgtttaca ggtgttgttc cgattctggt tgaactggat      60
ggtgatgtta atggccacaa attttcagtt agcggtgaag cgaaggtga tgcaacctat     120
ggtaaactga ccctgaaatt tatctgtacc accggcaaac tgccggttcc gtggccgaca     180
ctggttacca cactgaccta tggtgttcag tgttttagcc gttatccgga tcacatgaaa     240
cagcacgatt ttttcaaaag cgcaatgccg gaaggttatg ttcaagaacg taccatcttc     300
ttcaaagatg acggcaacta taaaacccgt gccgaagtta aatttgaagg tgataccctg     360
gtgaatcgca ttgaactgaa aggcatcgat tttaaagagg atggtaatat cctgggccac     420
aaactggaat ataattataa tagccacaac gtgtacatca tggccgacaa acagaaaaat     480
ggcatcaaag tgaacttcaa gatccgccat aatattgaag atggttcagt tcagctggcc     540
gatcattatc agcagaatac cccgattggt gatggtccgg ttctgctgcc ggataatcat     600
tatctgagca cccagagcaa actgagcaaa gatccgaatg aaaaacgtga tcacatggtg     660
ctgctggaat tgttaccgc agcaggtatt accttaggta tggatgaact gtataaagtc     720
gacgcagaag cagcagcaaa agaagccgct gccaaagaag cggcagcgaa agaggcagcc     780
gcaaaagcac tggaagccga ggctgcggct aaagaggctg ctgcaaaaga agcagccgct     840
aaagaagctg cggctaaggc accggcagca aaacgtgtta aactggacgg tggtggtggt     900
agcaccggta tggacaagaa atacagcatc ggtttggata ttggcacgaa tagcgtgggt     960
tgggccgtta ttaccgacga gtacaaagtg ccgtccaaga attcaaagt gctgggcaat    1020
accgatcgcc atagcatcaa gaaaaatctg attggcgcac tgctgttcga cagcggtgag    1080
actgccgaag ctacgcgtct gaagcgtacg gcgcgtcgtc gctacacccg ccgtaagaac    1140
cgtatttgct atctgcaaga aatcttcagc aacgaaatgg ccaaagttga tgatagcttt    1200
tttcaccgcc tggaagagag ctttctggtg gaagaggata gaaacacga gcgccatccg    1260
atttttggta acattgtcga tgaagtggca taccatgaga agtacccgac catctaccac    1320
cttcgtaaga aactggtgga cagcaccgat aaagctgatc tgcgtctgat ttacctggcg    1380
ctggcccaca tgattaagtt tcgcggtcat tttctgatcg agggcgatct gaatccggac    1440
aattctgatg ttgacaagct gtttattcaa cttgtacaga cctacaacca gttgttcgaa    1500
gagaacccga tcaatgcgag cggtgttgat gccaaagcaa ttctgagcgc acgcctgagc    1560
aaatctcgcc gtttggagaa cctgattgca cagctgccgg gtgagaagaa aaacggtctg    1620
ttcggcaatc tgattgcact gtccctgggc ttgaccccga ttttaagag caacttcgac    1680
ctggccgaag atgcgaagct ccaattgagc aaagacacct acgacgatga cctggacaat    1740
ctgctggccc agattggcga ccagtacgca gatctgttct ggctgcgaa aaacctgagc    1800
gatgcaattc tgctgtcgga catcctgcgc gtgaatacgg aaatcacgaa agcgcctctg    1860
agcgcgtcta tgatcaagcg ctatgacgag caccaccaag atctgaccct gctgaaagct    1920
ctggtgagac aacaattgcc agagaagtat aaagaaattt tctttgacca gagcaaaaac    1980
ggctatgcgg gttacattga cggtggcgcc agccaagaag agttctacaa attcattaag    2040
```

```
cctatcctgg agaaaatgga tggcaccgaa gaactgctgg taaagctgaa tcgtgaagat    2100
ctgctgcgca aacagcgcac ttttgataac ggtagcattc cgcaccagat ccatctgggt    2160
gagttgcacg cgattttgcg tcgccaggaa gattttttatc cgttcttgaa agacaaccgt    2220
gagaaaatcg agaaaattct gacgttccgt atcccgtatt atgtcggccc gctggcgcgt    2280
ggtaatagcc gcttcgcgtg gatgacccgc aaatcagagg aaacgattac cccgtggaat    2340
tttgaggaag ttgttgataa gggtgcaagc gcgcagtcgt tcattgagcg tatgaccaac    2400
tttgacaaga atttgccgaa tgaaaaagtc ttgccgaagc actctctgct gtacgagtat    2460
tttaccgttt acaacgaatt gaccaaggtt aaatacgtca ccgaaggcat gcgcaaaccg    2520
gccttcctga gcggcgagca gaaaaaagca atcgttgacc tcttgtttaa gaccaaccgc    2580
aaggttacgg tcaaacaact gaaagaggac tatttcaaga aaattgaatg ttttgactcc    2640
gtagagatct ccggtgttga ggaccgtttc aacgcgagcc tgggcaccta ccatgatctg    2700
ctgaaaatta ttaaagacaa agattttctg gacaacgaag agaacgaaga tattctggaa    2760
gatatcgttc tgaccctgac gctgttcgaa gatcgtgaga tgattgagga acgtctgaaa    2820
acctacgcac acttgttcga tgacaaagtt atgaaacagc tgaagcgtcg tcgttacaca    2880
ggttggggcc gtctgagccg taagcttatc aatggtatcc gtgacaaaca gagcggtaag    2940
acgattctgg actttctgaa gtcagatggc ttcgccaatc gcaactttat gcaactgatt    3000
catgacgact ctctgacgtt caaggaagat atccaaaagg cacaggtgag cggtcagggt    3060
gatagcctgc atgagcatat cgcgaacctg gcgggtagcc cggctatcaa aaagggtatc    3120
ttacagactg tgaaagttgt ggatgaattg gttaaggtta tgggtcgtca caaccggaa    3180 aatattgtga tcgagatggc acgtgaaaat cagacgacgc aaaagggtca aaaaaattct    3240
cgtgagcgca tgaaacgtat tgaagagggt atcaaagaat tgggcagcca aattctgaaa    3300
gaacacccgg tcgagaacac ccagctgcaa aacgaaaaac tgtatttata ctatctgcag    3360
aacggtcgtg acatgtacgt ggatcaagaa ctggacatca atcgtttgag cgattacgat    3420
gttgatcata ttgtgcctca gagctttctg aaagacgatt cgatcgacaa caaagtgctg    3480
acccgtagcg acaagaatcg tggtaagagc gataacgtgc cgagcgaaga agtcgttaag    3540
aaaatgaaaa actactggcg tcagctgctg aacgccaagc tgattaccca gcgtaagttc    3600
gataacctga cgaaagccga gcgtggaggc ctgagcgagc tggacaaggc cggctttatc    3660
aagcgtcaac tggtggaaac ccgtcagatc actaaacatg tggcacagat cctggactcc    3720
cgcatgaata cgaaatatga cgagaatgac aagttgatcc gtgaagtcaa agttattacg    3780
ctgaaaagca aactggtgtc cgatttccgt aaagacttcc agttctataa agtccgtgaa    3840
atcaacaact atcatcacgc ccacgatgcg tacttgaacg ctgttgtggg caccgcactg    3900
atcaagaaat accctaagct cgaaagcgag tttgtctatg gtgactataa agtttacgac    3960
gtgcgtaaga tgatcgccaa gagcgagcaa gaaattggta aggctaccgc aaagtacttt    4020
ttctacagca acatcatgaa cttcttcaaa accgagatta ccctggcgaa cggtgagatc    4080
cgtaaacggc cgctgattga gactaatggc gaaacgggcg agattgtgtg gacaagggt    4140 cgcgatttcg ctacggttcg taaggtcctg agcatgccgc aagttaacat tgtcaagaaa    4200
actgaagtgc agacgggtgg ctttagcaaa gaatccatcc tgccgaagcg taatagcgat    4260
aaacttatcg cgcgtaaaaa agactggac ccaaagaaat atggcggctt tgatagcccg    4320
accgtcgcgt atagcgtgtt agtggtcgcg aaagttgaaa agggcaagag caagaaactg    4380
```

| | |
|---|---|
| aagtccgtca aagaacttct gggtatcacc atcatggaac gtagctcctt tgagaagaac | 4440 |
| ccgattgact tcttagaggc gaagggttat aaagaagtca aaaaagacct gattatcaag | 4500 |
| ctgccgaagt acagcctgtt tgagttggag aatggtcgta agcgcatgct ggcgagcgcg | 4560 |
| ggtgagctgc aaaagggcaa cgaactggcg ctgccgtcga aatacgtcaa ttttctgtac | 4620 |
| ctggccagcc actacgaaaa gctgaagggt tctccggaag ataacgaaca aaagcaactg | 4680 |
| ttcgttgagc aacataaaca ctacttggac gaaatcatcg agcaaattag cgaatttagc | 4740 |
| aaacgtgtca tcctggcgga cgcgaatctg gacaaggtcc tgtctgcata caataagcat | 4800 |
| cgcgacaaac caattcgtga gcaagcgag aatatcatcc acctgtttac gctgaccaac | 4860 |
| ctaggtgcgc cggcggcatt caagtatttc gatacgacca tcgaccgcaa gcgctatacc | 4920 |
| agcaccaaag aggtcctgga cgcgaccctg atccaccaga gcattaccgg cttatacgaa | 4980 |
| acccgtattg atttgagcca actgggtggc gatgaattcc cgaaaaaaaa gcgcaaagtt | 5040 |
| ggtggcggtg gtagcccgaa aaagaaacgt aaagtg | 5076 |

<210> SEQ ID NO 63
<211> LENGTH: 5013
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63

| | |
|---|---|
| atggttagca aaggtgaagc cgtgattaaa gaatttatgc gctttaaggt tcacatggaa | 60 |
| ggtagcatga atggccatga atttgaaatt gaaggtgaag gcgaaggtcg tccgtatgaa | 120 |
| ggcacccaga ccgcaaaact gaaagttacc aaaggtggtc cgctgccgtt tagctgggat | 180 |
| attctgagtc cgcagtttat gtatggtagc cgtgcatttacc caaacatcc ggcagatatt | 240 |
| ccggattatt acaaacagag ctttccggaa ggttttaaat gggaacgtgt gatgaatttt | 300 |
| gaagatggtg gtgcagttac cgttacacag gataccagcc tggaagatgg caccctgatc | 360 |
| tataaagtta aactgcgtgg caccaatttt ccgcctgatg gtccggttat gcagaaaaaa | 420 |
| acaatgggtt gggaagcaag caccgaacgt ctgtatcctg aagatggcgt tctgaaaggt | 480 |
| gatatcaaaa tggcactgcg tctgaaagat ggcggtcgtt atctggcaga tttcaaaacc | 540 |
| acctataaag ccaaaaaacc tgttcagatg cctggtgcct ataatgttga tcgtaaactg | 600 |
| gatattacca gccacaacga agattatacc gttgtggaac agtatgaacg tagcgaaggc | 660 |
| cgtcatagca caggtggtat ggatgaactg tataaagtcg acagcggtgg tagcagcggt | 720 |
| ggttcaagcg gtagcgaaac accgggtaca agcgaaagcg caacaccgga aagcagtggt | 780 |
| ggtagttcag gtggtagtcc ggcagcaaaa cgtgtgaaac tggatggcgg tggcggtagc | 840 |
| accggtatgg acaagaaata cagcatcggt ttggatattg cacgaatag cgtgggttgg | 900 |
| gccgttatta ccgacgagta caagtgccg tccaagaaat tcaaagtgct gggcaatacc | 960 |
| gatcgccata gcatcaagaa aaatctgatt ggcgcactgc tgttcgacag cggtgagact | 1020 |
| gccgaagcta cgcgtctgaa gcgtacggcg cgtcgtcgct acacccgccg taagaaccgt | 1080 |
| atttgctatc tgcaagaaat cttcagcaac gaaatggcca agttgatga tagctttttt | 1140 |
| caccgcctgg aagagagctt tctggtggaa gaggataaga acacgagcg ccatccgatt | 1200 |
| tttggtaaca ttgtcgatga agtggcatac catgagaagt acccgaccat ctaccacctt | 1260 |
| cgtaagaaac tggtggacag caccgataaa gctgatctgc gtctgattta cctggcgctg | 1320 |

```
gcccacatga ttaagtttcg cggtcatttt ctgatcgagg gcgatctgaa tccggacaat    1380
tctgatgttg acaagctgtt tattcaactt gtacagacct acaaccagtt gttcgaagag    1440
aacccgatca atgcgagcgg tgttgatgcc aaagcaattc tgagcgcacg cctgagcaaa    1500
tctcgccgtt tggagaacct gattgcacag ctgccgggtg agaagaaaaa cggtctgttc    1560
ggcaatctga ttgcactgtc cctgggcttg accccgaatt ttaagagcaa cttcgacctg    1620
gccgaagatg cgaagctcca attgagcaaa gacacctacg acgatgacct ggacaatctg    1680
ctggcccaga ttggcgacca gtacgcagat ctgttcttgg ctgcgaaaaa cctgagcgat    1740
gcaattctgc tgtcggacat cctgcgcgtg aatacggaaa tcacgaaagc gcctctgagc    1800
gcgtctatga tcaagcgcta tgacgagcac caccaagatc tgaccctgct gaaagctctg    1860
gtgagacaac aattgccaga gaagtataaa gaattttctt tgaccagag caaaaacggc    1920 tatgcgggtt acattgacgg tggcgccagc caagaagagt tctacaaatt cattaagcct    1980
atcctggaga aaatggatgg caccgaagaa ctgctggtaa agctgaatcg tgaagatctg    2040
ctgcgcaaac agcgcacttt tgataacggt agcattccgc accagatcca tctgggtgag    2100
ttgcacgcga ttttgcgtcg ccaggaagat ttttatccgt tcttgaaaga caaccgtgag    2160
aaaatcgaga aaattctgac gttccgtatc ccgtattatg tcggcccgct ggcgcgtggt    2220
aatagccgct tcgcgtggat gacccgcaaa tcagaggaaa cgattacccc gtggaatttt    2280
gaggaagttg ttgataaggg tgcaagcgcg cagtcgttca ttgagcgtat gaccaacttt    2340
gacaagaatt tgccgaatga aaaagtcttg ccgaagcact ctctgctgta cgagtatttt    2400
accgtttaca cgaattgac caaggttaaa tacgtcaccg aaggcatgcg caaaccggcc    2460
ttcctgagcg gcgagcagaa aaaagcaatc gttgacctct tgtttaagac caaccgcaag    2520
gttacggtca acaactgaa agaggactat ttcaagaaaa ttgaatgttt tgactccgta    2580
gagatctccg gtgttgagga ccgtttcaac gcgagcctgg gcacctacca tgatctgctg    2640
aaaattatta agacaaaga ttttctggac aacgaagaga cgaagatat tctggaagat    2700 atcgttctga ccctgacgct gttcgaagat cgtgagatga ttgaggaacg tctgaaaacc    2760
tacgcacact tgttcgatga caaagttatg aaacagctga gcgtcgtcg ttacacaggt    2820 tggggccgtc tgagccgtaa gcttatcaat ggtatccgtg acaaacagag cggtaagacg    2880
attctggact ttctgaagtc agatggcttc gccaatcgca actttatgca actgattcat    2940
gacgactctc tgacgttcaa ggaagatatc caaaaggcac aggtgagcgg tcagggtgat    3000
agcctgcatg agcatatcgc gaacctggcg ggtagcccgg ctatcaaaaa gggtatctta    3060
cagactgtga agttgtgga tgaattggtt aaggttatgg gtcgtcacaa accggaaaat    3120
attgtgatcg agatggcacg tgaaaatcag acgacgcaaa agggtcaaaa aaattctcgt    3180
gagcgcatga acgtattga agagggtatc aaagaattgg gcagccaaat tctgaaagaa    3240
cacccggtcg agaacaccca gctgcaaaac gaaaaactgt atttatacta tctgcagaac    3300
ggtcgtgaca tgtacgtgga tcaagaactg acatcaatc gtttgagcga ttacgatgtt    3360
gatcatattg tgcctcagag ctttctgaaa gacgattcga tcgacaacaa agtgctgacc    3420
cgtagcgaca gaatcgtgg taagagcgat aacgtgccga gcgaagaagt cgttaagaaa    3480
atgaaaaact actggcgtca gctgctgaac gccaagctga ttacccagcg taagttcgat    3540
aacctgacga aagccgagcg tggaggcctg agcgagctgg acaaggccgg ctttatcaag    3600
cgtcaactgg tggaaacccg tcagatcact aaacatgtgg cacagatcct ggactcccgc    3660
atgaatacga aatatgacga gaatgacaag ttgatccgtg aagtcaaagt tattacgctg    3720
```

```
aaaagcaaac tggtgtccga tttccgtaaa gacttccagt tctataaagt ccgtgaaatc    3780
aacaactatc atcacgccca cgatgcgtac ttgaacgctg ttgtgggcac cgcactgatc    3840
aagaaatacc ctaagctcga aagcgagttt gtctatggtg actataaagt ttacgacgtg    3900
cgtaagatga tcgccaagag cgagcaagaa attggtaagg ctaccgcaaa gtactttttc    3960
tacagcaaca tcatgaactt cttcaaaacc gagattaccc tggcgaacgg tgagatccgt    4020
aaacggccgc tgattgagac taatggcgaa acgggcgaga ttgtgtggga caagggtcgc    4080
gatttcgcta cggttcgtaa ggtcctgagc atgccgcaag ttaacattgt caagaaaact    4140
gaagtgcaga cgggtggctt tagcaaagaa tccatcctgc cgaagcgtaa tagcgataaa    4200
cttatcgcgc gtaaaaaaga ctgggaccca agaaatatg gcggctttga tagcccgacc    4260
gtcgcgtata gcgtgttagt ggtcgcgaaa gttgaaaagg gcaagagcaa gaaactgaag    4320
tccgtcaaag aacttctggg tatcaccatc atggaacgta gctcctttga agaacccg     4380 attgacttct tagaggcgaa gggttataaa gaagtcaaaa aagacctgat tatcaagctg    4440
ccgaagtaca gcctgtttga gttggagaat ggtcgtaagc gcatgctggc gagcgcgggt    4500
gagctgcaaa agggcaacga actggcgctg ccgtcgaaat acgtcaattt tctgtacctg    4560
gccagccact acgaaaagct gaagggttct ccggaagata cgaacaaaa gcaactgttc    4620 gttgagcaac ataaacacta cttggacgaa atcatcgagc aaattagcga atttagcaaa    4680
cgtgtcatcc tggcggacgc gaatctggac aaggtcctgt ctgcatacaa taagcatcgc    4740
gacaaaccaa ttcgtgagca agcggagaat atcatccacc tgtttacgct gaccaaccta    4800
ggtgcgccgg cggcattcaa gtatttcgat acgaccatcg accgcaagcg ctataccagc    4860
accaaagagg tcctggacgc gaccctgatc caccagagca ttaccggctt atacgaaacc    4920
cgtattgatt tgagccaact gggtggcgat gaattcccga aaaaaaagcg caaagttggt    4980
ggcggtggta gcccgaaaaa gaaacgtaaa gtg                                 5013
```

<210> SEQ ID NO 64
<211> LENGTH: 5034
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 64

```
atggttagca aaggtgaaga actgtttaca ggtgttgttc cgattctggt tgaactggat      60
ggtgatgtta atggccacaa attttcagtt agcggtgaag cgaaggtga tgcaacctat     120 ggtaaactga ccctgaaatt tatctgtacc accggcaaac tgccggttcc gtggccgaca    180
ctggttacca cactgaccta tggtgttcag tgttttagcc gttatccgga tcacatgaaa    240
cagcacgatt ttttcaaaag cgcaatgccg gaaggttatg ttcaagaacg taccatcttc    300
ttcaaagatg acggcaacta taaacccgt gccgaagtta aatttgaagg tgataccctg    360
gtgaatcgca ttgaactgaa aggcatcgat tttaagagg atggtaatat cctgggccac    420
aaactggaat ataattataa tagccacaac gtgtacatca tggccgacaa acagaaaaat    480
ggcatcaaag tgaacttcaa gatccgccat aatattgaag atggttcagt tcagctggcc    540
gatcattatc agcagaatac cccgattggt gatggtccgg ttctgctgcc ggataatcat    600
tatctgagca cccagagcaa actgagcaaa gatccgaatg aaaaacgtga tcacatggtg    660
ctgctggaat ttgttaccgc agcaggtatt accttaggta tggatgaact gtataaagtc    720
```

```
gacagcggtg gtagcagcgg tggttcaagc ggtagcgaaa caccgggtac aagcgaaagc      780
gcaacaccgg aaagcagtgg tggtagctca ggtggtagtc cggcagcaaa acgtgttaaa      840
ctggacggtg gtggtggtag caccggtatg gacaagaaat acagcatcgg tttggatatt      900
ggcacgaata gcgtgggttg ggccgttatt accgacgagt acaaagtgcc gtccaagaaa      960
ttcaaagtgc tgggcaatac cgatcgccat agcatcaaga aaaatctgat tggcgcactg     1020
ctgttcgaca gcgtgagac tgccgaagct acgcgtctga agcgtacggc gcgtcgtcgc      1080
tacacccgcc gtaagaaccg tatttgctat ctgcaagaaa tcttcagcaa cgaaatggcc     1140
aaagttgatg atagcttttt tcaccgcctg gaagagagct ttctggtgga agaggataag     1200
aaacacgagc gccatccgat ttttggtaac attgtcgatg aagtggcata ccatgagaag     1260
tacccgacca tctaccacct tcgtaagaaa ctggtggaca gcaccgataa agctgatctg     1320
cgtctgattt acctggcgct ggcccacatg attaagtttc gcggtcattt tctgatcgag     1380
ggcgatctga atccggacaa ttctgatgtt gacaagctgt ttattcaact tgtacagacc     1440
tacaaccagt tgttcgaaga gaacccgatc aatgcgagcg tgttgatgc caaagcaatt      1500
ctgagcgcac gcctgagcaa atctcgccgt ttggagaacc tgattgcaca gctgccgggt     1560
gagaagaaaa acggtctgtt cggcaatctg attgcactgt ccctgggctt gaccccgaat     1620
tttaagagca cttcgacct ggccgaagat gcgaagctcc aattgagcaa agacacctac       1680
gacgatgacc tggacaatct gctggcccag attggcgacc agtacgcaga tctgttcttg     1740
gctgcgaaaa acctgagcga tgcaattctg ctgtcggaca tcctgcgcgt gaatacggaa     1800
atcacgaaag cgcctctgag cgcgtctatg atcaagcgct atgacgagca ccaccaagat     1860
ctgaccctgc tgaaagctct ggtgagacaa caattgccag agaagtataa agaaattttc     1920
tttgaccaga gcaaaaacgg ctatgcgggt tacattgacg gtggcgccag ccaagaagag     1980
ttctacaaat tcattaagcc tatcctggag aaaatggatg caccgaaga actgctggta      2040
aagctgaatc gtgaagatct gctgcgcaaa cagcgcactt ttgataacgg tagcattccg     2100
caccagatcc atctgggtga gttgcacgcg attttgcgtc gccaggaaga tttttatccg     2160
ttcttgaaag acaaccgtga gaaaatcgag aaaattctga cgttccgtat cccgtattat     2220
gtcggcccgc tggcgcgtgg taatagccgc ttcgcgtgga tgacccgcaa atcagaggaa     2280
acgattaccc cgtggaattt tgaggaagtt gttgataagg gtgcaagcgc gcagtcgttc     2340
attgagcgta tgaccaactt tgacaagaat ttgccgaatg aaaaagtctt gccgaagcac     2400
tctctgctgt acgagtattt taccgtttac aacgaattga ccaaggttaa atacgtcacc     2460
gaaggcatgc gcaaaccggc cttcctgagc ggcgagcaga aaaaagcaat cgttgacctc     2520
ttgtttaaga ccaaccgcaa ggttacggtc aaacaactga agaggacta tttcaagaaa      2580
attgaatgtt ttgactccgt agagatctcc ggtgttgagg accgtttcaa cgcgagcctg     2640
ggcacctacc atgatctgct gaaaattatt aagacaaag attttctgga caacgaagag      2700
aacgaagata ttctggaaga tatcgttctg accctgacgc tgttcgaaga tcgtgagatg     2760
attgaggaac gtctgaaaac ctacgcacac ttgttcgatg acaaagttat gaaacagctg     2820
aagcgtcgtc gttacacagg ttggggccgt ctgagccgta agcttatcaa tggtatccgt     2880
gacaaacaga gcgtaagac gattctggac tttctgaagt cagatggctt cgccaatcgc     2940
aactttatgc aactgattca tgacgactct ctgacgttca aggaagatat ccaaaaggca     3000
caggtgagcg gtcagggtga tagcctgcat gagcatatcg cgaacctggc gggtagcccg     3060
```

```
gctatcaaaa agggtatctt acagactgtg aaagttgtgg atgaattggt taaggttatg    3120
ggtcgtcaca aaccggaaaa tattgtgatc gagatggcac gtgaaaatca gacgacgcaa    3180
aagggtcaaa aaaattctcg tgagcgcatg aaacgtattg aagagggtat caaagaattg    3240
ggcagccaaa ttctgaaaga acacccggtc gagaacaccc agctgcaaaa cgaaaaactg    3300
tatttatact atctgcagaa cggtcgtgac atgtacgtgg atcaagaact ggacatcaat    3360
cgtttgagcg attacgatgt tgatcatatt gtgcctcaga gctttctggc ggacgattcg    3420
atcgacaaca aagtgctgac ccgtagcgac aagaatcgtg gtaagagcga taacgtgccg    3480
agcgaagaag tcgttaagaa aatgaaaaac tactggcgtc agctgctgaa cgccaagctg    3540
attacccagc gtaagttcga taacctgacg aaagccgagc gtggaggcct gagcgagctg    3600
gacaaggccg gctttatcaa gcgtcaactg gtggaaaccc gtcagatcac taaacatgtg    3660
gcacagatcc tggactcccg catgaatacg aaatatgacg agaatgacaa gttgatccgt    3720
gaagtcaaag ttattacgct gaaaagcaaa ctggtgtccg atttccgtaa agacttccag    3780
ttctataaag tccgtgaaat caacaactat catcacgccc acgatgcgta cttgaacgct    3840
gttgtgggca ccgcactgat caagaaatac cctgcactcg aaagcgagtt tgtctatggt    3900
gactataaag tttacgacgt gcgtaagatg atcgccaaga gcgagcaaga aattggtaag    3960
gctaccgcaa agtactttt ctacagcaac atcatgaact tcttcaaaac cgagattacc    4020
ctggcgaacg tgagatccg taaagcgccg ctgattgaga ctaatggcga aacgggcgag    4080
attgtgtggg acaagggtcg cgatttcgct acggttcgta aggtcctgag catgccgcaa    4140
gttaacattg tcaagaaaac tgaagtgcag acgggtggct ttagcaaaga atccatcctg    4200
ccgaagcgta atagcgataa acttatcgcg cgtaaaaaag actgggaccc aaagaaatat    4260
ggcggctttg atagcccgac cgtcgcgtat agcgtgttag tggtcgcgaa agttgaaaag    4320
ggcaagagca agaaactgaa gtccgtcaaa gaacttctgg gtatcaccat catggaacgt    4380
agctcctttg agaagaaccc gattgacttc ttagaggcga agggttataa agaagtcaaa    4440
aaagacctga ttatcaagct gccgaagtac agcctgtttg agttggagaa tggtcgtaag    4500
cgcatgctgg cgagcgcggg tgagctgcaa aagggcaacg aactggcgct gccgtcgaaa    4560
tacgtcaatt ttctgtacct ggccagccac tacgaaaagc tgaagggttc tccggaagat    4620
aacgaacaaa agcaactgtt cgttgagcaa cataaacact acttggacga aatcatcgag    4680
caaattagcg aatttagcaa acgtgtcatc ctggcggacg cgaatctgga caaggtcctg    4740
tctgcataca ataagcatcg cgacaaacca attcgtgagc aagcggagaa tatcatccac    4800
ctgtttacgc tgaccaacct aggtgcgccg gcggcattca agtatttcga tacgaccatc    4860
gaccgcaagc gctataccag caccaaagag gtcctggacg cgaccctgat ccaccagagc    4920
attaccggct tatacgaaac ccgtattgat ttgagccaac tgggtggcga tgaattcccg    4980
aaaaaaaagc gcaaagttgg tggcggtggt agcccgaaaa agaaacgtaa agtg          5034
```

<210> SEQ ID NO 65
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 65

```
gcucccauca caucaaccgg                                                 20
```

```
<210> SEQ ID NO 66
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
ggugagugag ugugugcgug                                                     20
```